US011851664B2

(12) United States Patent
Song et al.

(10) Patent No.: US 11,851,664 B2
(45) Date of Patent: Dec. 26, 2023

(54) **METHODS FOR PRODUCING BIOCHEMICALS USING ENZYME GENES DERIVED FROM A STRAIN OF *BREVUNDIMONAS*, AND COMPOSITIONS MADE THEREBY**

(71) Applicant: Oakbio, Inc., Sunnyvale, CA (US)

(72) Inventors: Chia-Han Song, Palo Alto, CA (US); William J. Coleman, Redwood City, CA (US); Brian Sefton, Sunnyvale, CA (US)

(73) Assignee: OAKBIO, INC., Sunnyvale, CA (US)

( * ) Notice: Subject to any disclaimer, the term of this patent is extended or adjusted under 35 U.S.C. 154(b) by 169 days.

(21) Appl. No.: 17/395,421

(22) Filed: Aug. 5, 2021

(65) Prior Publication Data

US 2022/0204979 A1 Jun. 30, 2022

Related U.S. Application Data

(60) Provisional application No. 63/130,569, filed on Dec. 24, 2020.

(51) Int. Cl.
*C12N 15/74* (2006.01)
*C12N 9/02* (2006.01)

(52) U.S. Cl.
CPC .......... *C12N 15/74* (2013.01); *C12N 9/0083* (2013.01); *C12N 2800/101* (2013.01)

(58) Field of Classification Search
None
See application file for complete search history.

(56) References Cited

U.S. PATENT DOCUMENTS

| | | | |
|---|---|---|---|
| 5,705,361 | A | 1/1998 | Walker et al. |
| 5,811,273 | A | 9/1998 | Misawa et al. |
| 5,910,433 | A | 6/1999 | Kajiwara et al. |
| 7,252,985 | B2 | 8/2007 | Cheng et al. |
| 2004/0078846 | A1 | 4/2004 | Desouza et al. |
| 2006/0141558 | A1 | 6/2006 | Tang et al. |
| 2012/0142082 | A1 | 6/2012 | Sharpe et al. |
| 2017/0173086 | A1 | 6/2017 | Boyle et al. |
| 2020/0181660 | A1 | 6/2020 | Peters-Wendisch et al. |

FOREIGN PATENT DOCUMENTS

| | | | |
|---|---|---|---|
| EP | 1694854 | B1 | 9/2011 |
| KR | 20090093679 | A | 9/2009 |
| WO | 2005/118812 | A1 | 12/2005 |

OTHER PUBLICATIONS

JP2021-033930 Argument and Amendment filed Nov. 4, 2022.
JP2021-033930 Decision of Refusal dated Feb. 21, 2023.
Ambati, Ranga Rao, et al. "Astaxanthin: Sources, extraction, stability, biological activities and its commercial applications—A review." Marine drugs 12.1 (2014): 128-152.
Bampidis et al., EFSA Panel on Additives and Products or Substances used in Animal Feed (EFSA FEEDAP Panel), "Guidance on the assessment of the safety of feed additives for the environment" EFSA Journal 17.4 (2019): e05648.
Barredo, José-Luis. "Microbial carotenoids from bacteria and microalgae." Methods and Protocols; Humana Press New York, NY, USA (2012): 5.
Barreiro, Carlos, and José-Luis Barredo. Microbial carotenoids. New York, NY, USA:: Springer, 2018.
Brotosudarmo, Tatas Hardo Panintingjati, Leenawaty Limantara, and Edi Setiyono. "Structures of astaxanthin and their consequences for therapeutic application." International Journal of Food Science 2020 (2020).
Cho, Kyoung Sang, et al. "Recent advances in studies on the therapeutic potential of dietary carotenoids in neurodegenerative diseases." Oxidative medicine and cellular longevity 2018 (2018).
Sanzo, Giuseppe Di, et al. "Supercritical carbon dioxide extraction of astaxanthin, lutein, and fatty acids from Haematococcus pluvialis microalgae." Marine drugs 16.9 (2018): 334.
Ernst, Hansgeorg. "Recent advances in industrial carotenoid synthesis." Pure and applied chemistry 74.11 (2002): 2213-2226.
Gharibzahedi, Seyed Mohammad Taghi, Seyed Hadi Razavi, and Seyed Mohammad Mousavi. "Microbial canthaxanthin: perspectives on biochemistry and biotechnological production." Engineering in Life Sciences 13.4 (2013): 408-417.
Gregorio, Nicole E., Max Z. Levine, and Javin P. Oza. "A user's guide to cell-free protein synthesis." Methods and protocols 2.1 (2019): 24.
Gruber, Steffen, Helmut Schwab, and Petra Koefinger. "Versatile plasmid-based expression systems for Gram-negative bacteria—General essentials exemplified with the bacterium Ralstonia eutropha H16." New biotechnology 32.6 (2015): 552-558.
Hayes, Finbarr. "Transposon-based strategies for microbial functional genomics and proteomics." Annual review of genetics 37 (2003): 3.
"Belcher/Knight: Electrocompetent Cells." found at https://openwetware.org/wiki/Belcher/Knight:_Electrocompetent_Cells, last accessed Nov. 21, 2022, 2 pages.
Johnson, Abayomi Oluwanbe, et al. "An engineered constitutive promoter set with broad activity range for Cupriavidus necator H16." ACS Synthetic Biology 7.8 (2018): 1918-1928.
Kosuri, Sriram, and George M. Church. "Large-scale de novo DNA synthesis: technologies and applications." Nature methods 11.5 (2014): 499-507.
Kovach, M. E., et al. "pBBR1MCS: a broad-host-range cloning vector." Biotechniques 16.5 (1994): 800-802.

(Continued)

*Primary Examiner* — Suzanne M Noakes
*Assistant Examiner* — Jae W Lee
(74) *Attorney, Agent, or Firm* — Rimon Law, P.C.

(57) ABSTRACT

A crtW gene from a strain of *Brevundimonas* is disclosed that encodes a novel ketolase for carotenoid synthesis. An exemplary synthetic operon containing additional relevant carotenoid gene sequences is also provided, where the expression of the synthetic operon is used to produce ketocarotenoids. Suitable DNA expression constructs derived from these sequences are inserted into an expression host for expression. The expression product is a ketolase enzyme that is operable for transforming beta-carotene into canthaxanthin and astaxanthin.

9 Claims, 10 Drawing Sheets

Specification includes a Sequence Listing.

(56) References Cited

OTHER PUBLICATIONS

Lenz, Oliver, Lars Lauterbach, and Stefan Frielingsdorf. "O2-tolerant [NiFe]-hydrogenases of Ralstonia eutropha H16: Physiology, molecular biology, purification, and biochemical analysis." Methods in enzymology. vol. 613. Academic Press, 2018. 117-151.
Makino, Tomohiro, Georgios Skretas, and George Georgiou. "Strain engineering for improved expression of recombinant proteins in bacteria" Microbial cell factories 10.1 (2011): 1-10.
Misawa, Norihiko, et al. "Structure and functional analysis of a marine bacterial carotenoid biosynthesis gene cluster and astaxanthin biosynthetic pathway proposed at the gene level." Journal of bacteriology 177.22 (1995): 6575-6584.
Misawa, Norihiko. "Carotenoid β-ring hydroxylase and ketolase from marine bacteria—promiscuous enzymes for synthesizing functional xanthophylls." Marine drugs 9.5 (2011): 757-771.
Sankari, Mohan, et al. "Prospects and progress in the production of valuable carotenoids: Insights from metabolic engineering, synthetic biology, and computational approaches." Journal of Biotechnology 266 (2018): 89-101.
Khambhati, Khushal, et al. "Exploring the potential of cell-free protein synthesis for extending the abilities of biological systems." Frontiers in bioengineering and biotechnology 7 (2019): 248.
Nishida, Yasuhiro, et al. "Elucidation of a carotenoid biosynthesis gene cluster encoding a novel enzyme, 2, 2'-β-hydroxylase, from *Brevundimonas* sp. strain SD212 and combinatorial biosynthesis of new or rare xanthophylls." Applied and environmental microbiology 71.8 (2005): 4286-4296.
Niu, Fu-Xing, et al. "Metabolic engineering for the microbial production of isoprenoids: carotenoids and isoprenoid-based biofuels" Synthetic and Systems Biotechnology 2.3 (2017): 167-175.
Petersen, Leander AH, et al. "Mixing and mass transfer in a pilot scale U-loop bioreactor." Biotechnology and Bioengineering 114.2 (2017): 344-354.
Petersen, Leander AH, et al. "Modeling and system identification of an unconventional bioreactor used for single cell protein production." Chemical Engineering Journal 390 (2020): 124438.
Phomphisutthimas, Somkiat, Arinthip Thamchaipenet, and Bhinyo Panijpan. "Conjugation in *Escherichia coli*: A laboratory exercise" Biochemistry and molecular biology education 35.6 (2007): 440-445.
Raberg, Matthias, et al. "Ralstonia eutropha H16 in progress: applications beside PHAs and establishment as production platform by advanced genetic tools." Critical reviews in biotechnology 38.4 (2018): 494-510.
Reznikoff, William S. "The TN5 transposon." Annual review of microbiology 47.1 (1993): 945-963.
Schneider, Birgit, et al. "Membrane protein expression in cell-free systems." Heterologous Expression of Membrane Proteins. Humana Press, 2010. 165-186.
Tao, L., and Q. Cheng. "Novel β-carotene ketolases from non-photosynthetic bacteria for canthaxanthin synthesis." Molecular Genetics and Genomics 272.5 (2004): 530-537.
Tao, Luan, Pierre E. Rouvière, and Qiong Cheng. "A carotenoid synthesis gene cluster from a non-marine Brevundimonas that synthesizes hydroxylated astaxanthin." Gene 379 (2006): 101-108.
Tizei, Pedro AG, et al. "Selection platforms for directed evolution in synthetic biology." Biochemical Society Transactions 44.4 (2016): 1165-1175.
Ukibe, Ken, et al. "Efficient screening for astaxanthin-overproducing mutants of the yeast *Xanthophyllomyces dendrorhous* by flow cytometry." FEMS microbiology letters 286.2 (2008): 241-248.
Ye, Rick W., et al. "Mutational and functional analysis of the β-carotene ketolase involved in the production of canthaxanthin and astaxanthin." Applied and Environmental Microbiology 72.9 (2006): 5829-5837.
Ye, Lijun, et al. "Optimizing the localization of astaxanthin enzymes for improved productivity." Biotechnology for biofuels 11.1 (2018): 1-9.
Zhang, Congqiang. "Biosynthesis of carotenoids and apocarotenoids by microorganisms and their industrial potential." Progress in carotenoid research 85 (2018).
Córdova, Pamela, et al. "Microbiological synthesis of carotenoids: pathways and regulation." Progress in carotenoid research. IntechOpen, 2018.
International Search Report and Written Opinion issued in related PCT Application No. PCT/US2021/064762 dated May 9, 2022, 27 pages.
Choi, S.K. et al., "Characterization of b-Carotene Ketolases, CrtW, from Marine Bacteria by Complementation Analysis in *Escherichia coli*." Marine Biotechnology. Epub Jul. 5, 2005, vol. 7, No. 5; pp. 515-517.
Nogueira, M et al., "Construction of a fusion enzyme for astaxanthin formation and its characterisation in microbial and plant hosts: A new tool for engineering ketocarotenoids." Metabolic Engineering. Mar. 2019, Epub Dec. 20, 2018, vol. 52; pp. 243-246.
Miyazaki, R et al., "Cloning vector pRMTn-Tc DNA, complete sequence." Genbank entry (online). National Institute of Biotechnology Information. Jun. 26, 2013 (Retrieved on Mar. 24, 2020). Retrieved from the Internet: [URL: https://www.ncbi.nlm.nih.gov/nucleotide/AB777650.1?report=genbank&log$=nucltop & blast_rank=7&RID=3M39JHKD013); pp. 1-4.
Wu, Y et al., "Combinatorial expression of different beta-carotene hydroxylases and ketolases in *Escherichia coli* for increased astaxanthin production." Journal of Industrial Microbiology and Biotechnology. Nov. 2019, Epub Jul. 11, 2019. vol. 46, No. 11; pp. 1505-1516; entire document; DOI: 10.1007/s10295-019-02214-1.
Menin, Barbara, et al. "Non-endogenous ketocarotenoid accumulation in engineered *Synechocystis* sp. PCC 6803." Physiologia plantarum 166.1 (2019): 403-412.
Office Action issued in related Japanese Patent Application No. 2021-033930, dated May 24, 2022, 5 pages (with translation.).
Database Uniprot KB, accession No. A0A0B4C6Q3, entry version 15 [May 13, 2022], Apr. 22, 2020, http://www.uniprot.org/uniprot/A0A0B4C6Q3.txt?version=15, 2 pages.
Database Uniprot KB, accession No. A0A0H3L7T7, entry version 21 [online], Dec. 2, 2020, [May 13, https://www.uniprot.org/uniprot/A0A0H3L7T7.txt?version=21, 2 pages.
Hmelo, Laura R., et al. "Precision-engineering the Pseudomonas aeruginosa genome with two-step allelic exchange." Nature protocols 10.11 (2015): 1820-1841.
Valderrama, Jose O., Michel Perrut, and Wieslaw Majewski. "Extraction of astaxantine and phycocyanine from microalgae with supercritical carbon dioxide." Journal of Chemical & Engineering Data 48.4 (2003): 827-830.

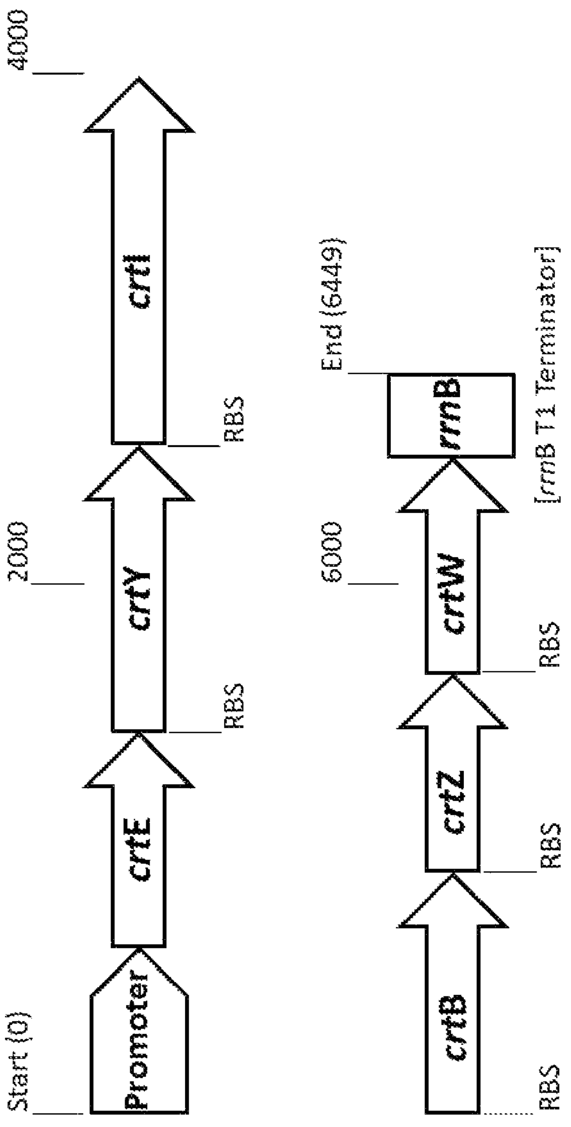
FIGURE 2. System 1 astaxanthin operon.

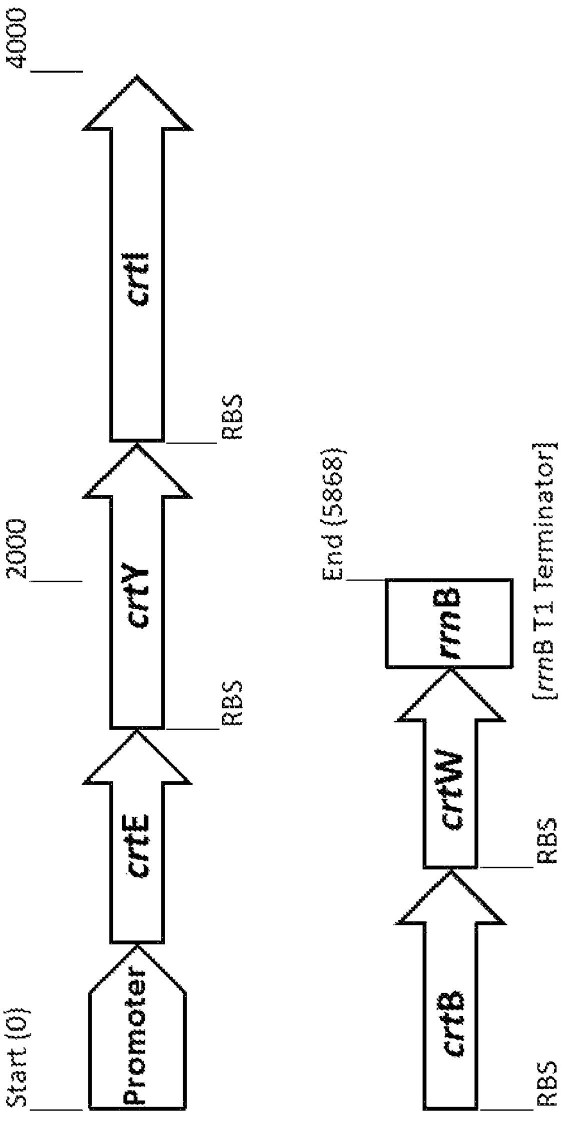
FIGURE 3. System 2 canthaxanthin operon.

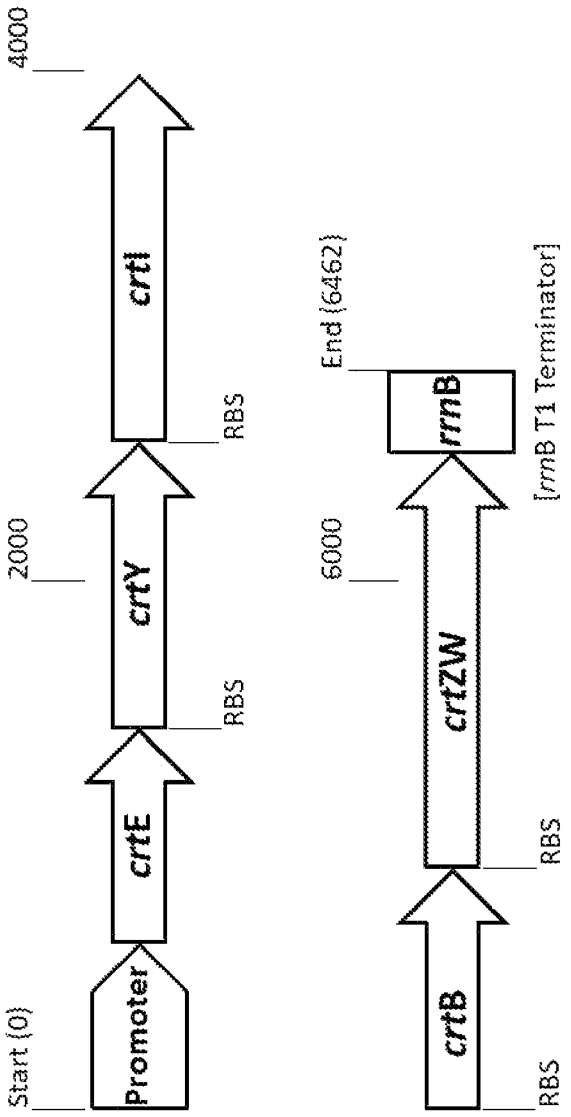
FIGURE 4. **System 3 astaxanthin operon with *crtZW* fusion gene.**

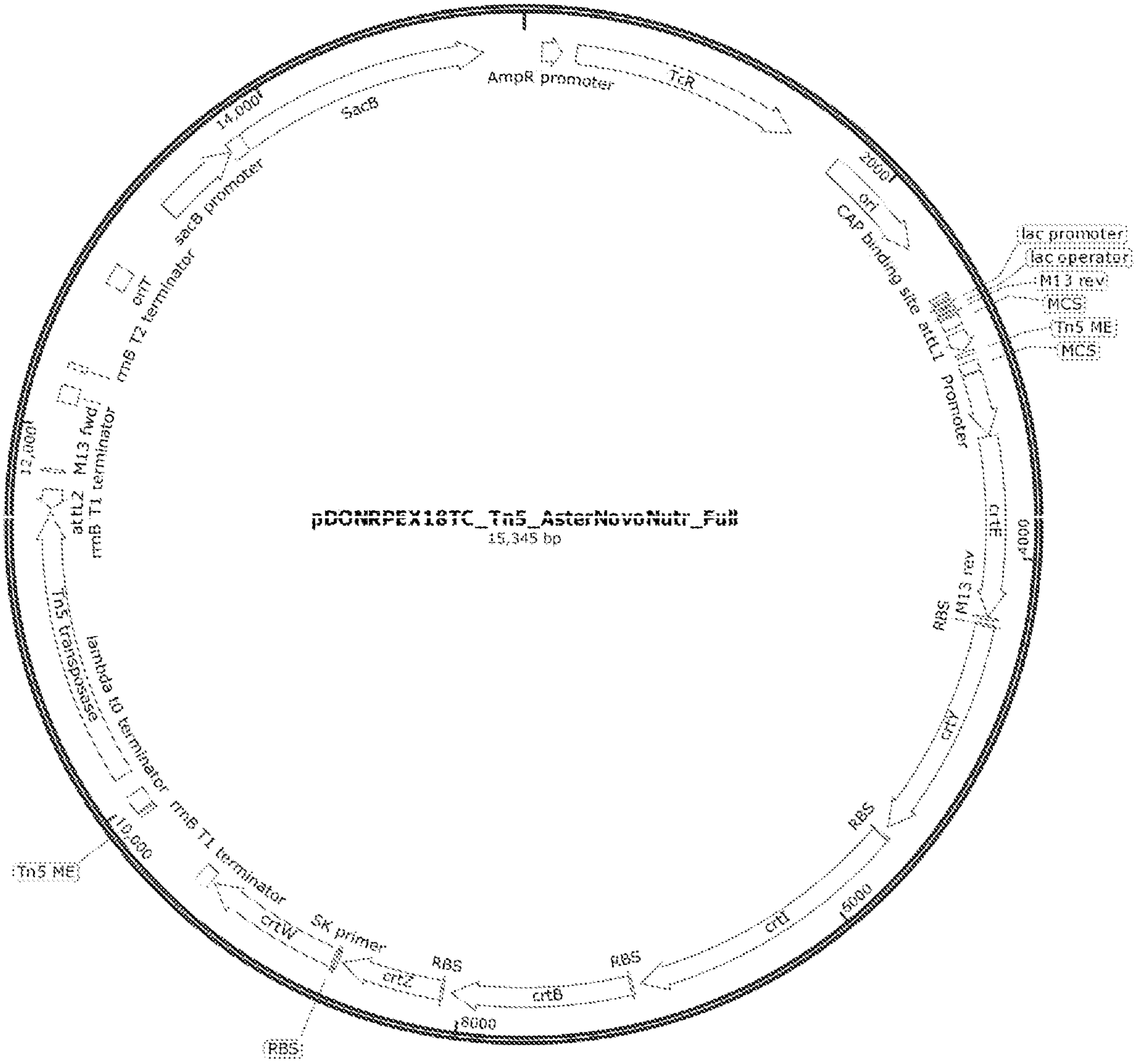
FIGURE 5. Map of complete Tn5 transposon-suicide vector construct for astaxanthin production.

ME = Mosaic Ends (inverted repeat sequences)
Pro = Promoter
Ori = Origin of replication or transfer
Term = Transcriptional terminator
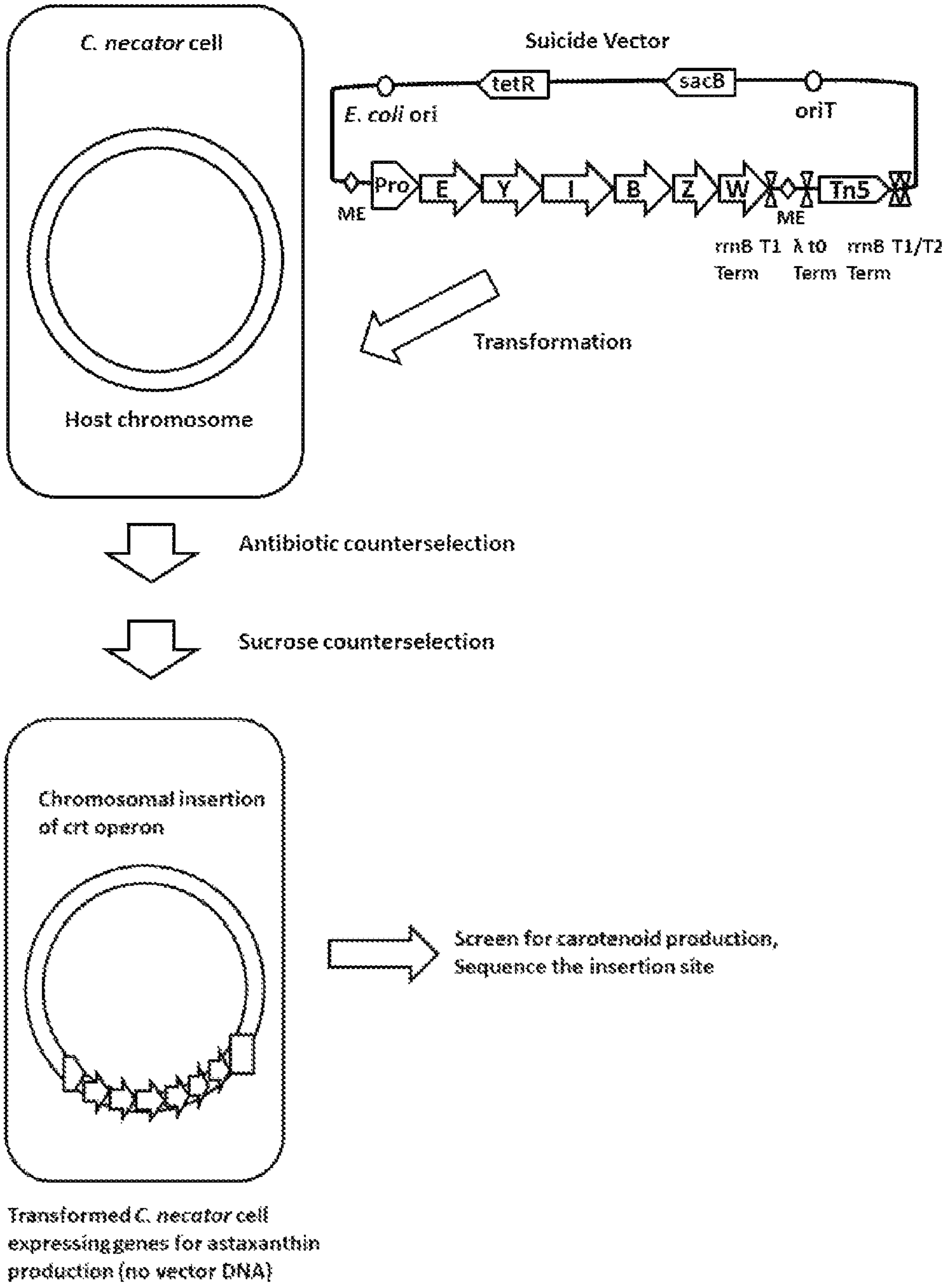
FIGURE 6. Transformation and chromosomal insertion of the operon into the host cell using transposon mutagenesis.

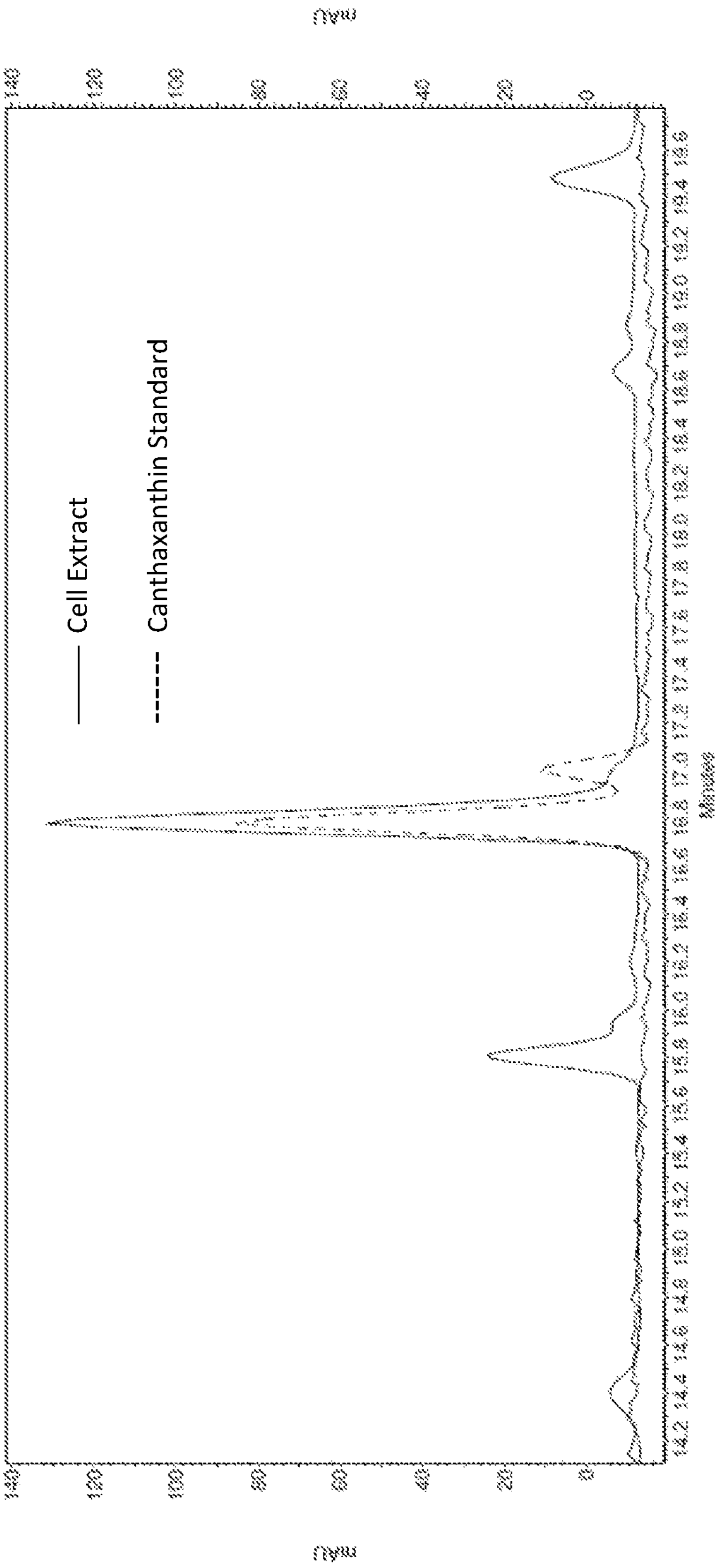
FIGURE 7. HPLC chromatogram for the products of the canthaxanthin-producing DNA insert.

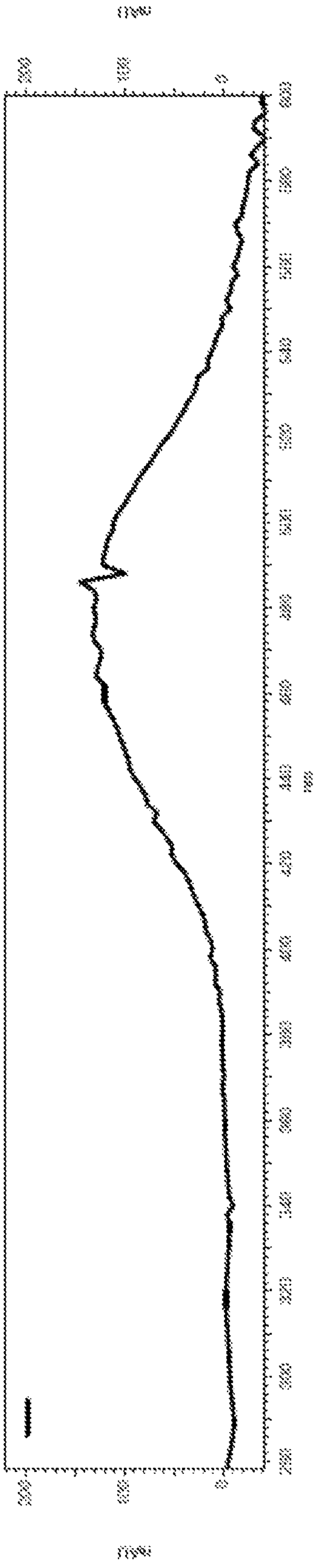
FIGURE 8. UV-Vis spectrum of the canthaxanthin product peak.

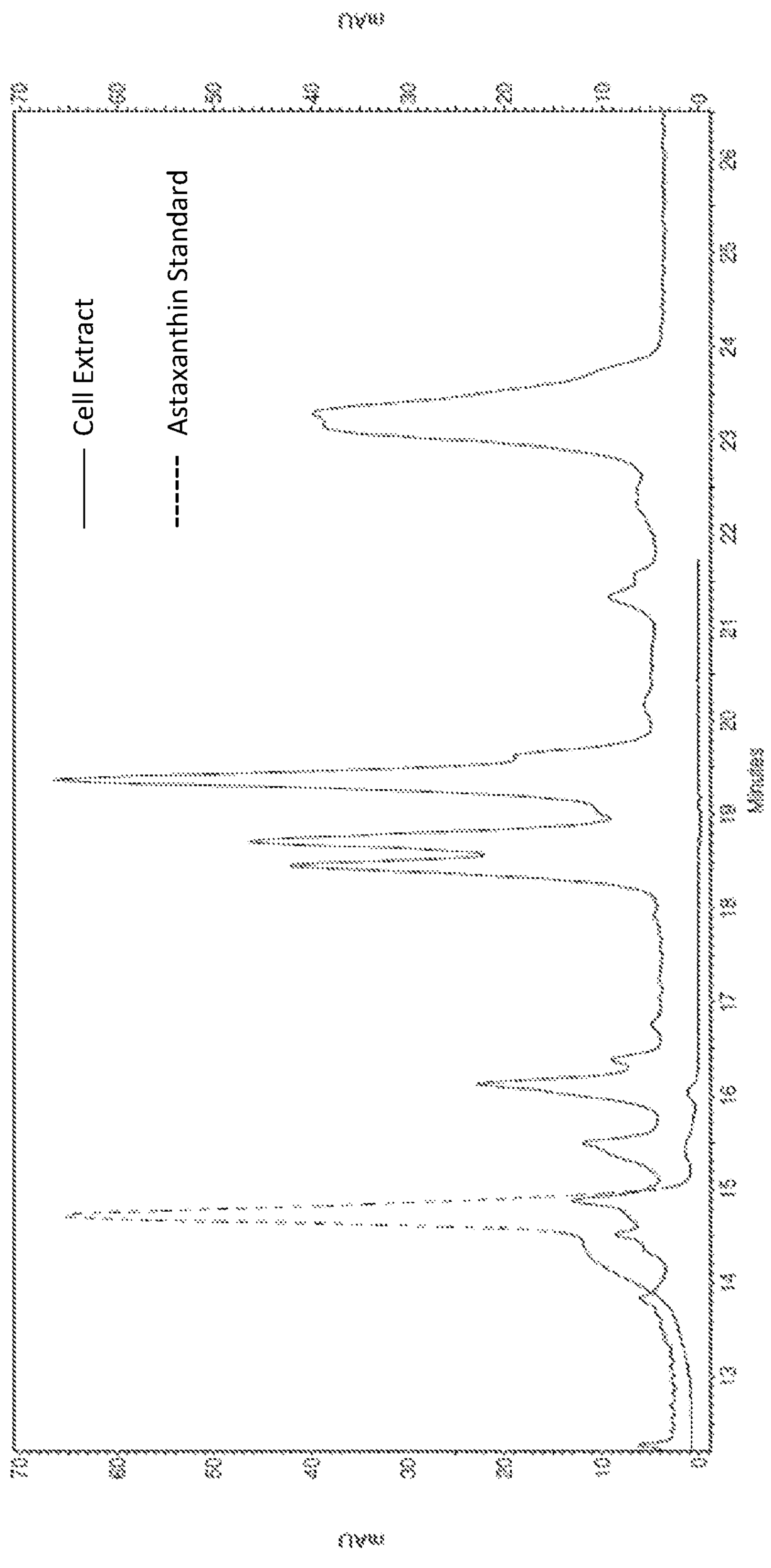
FIGURE 9. HPLC chromatogram for the products of the astaxanthin-producing DNA insert.

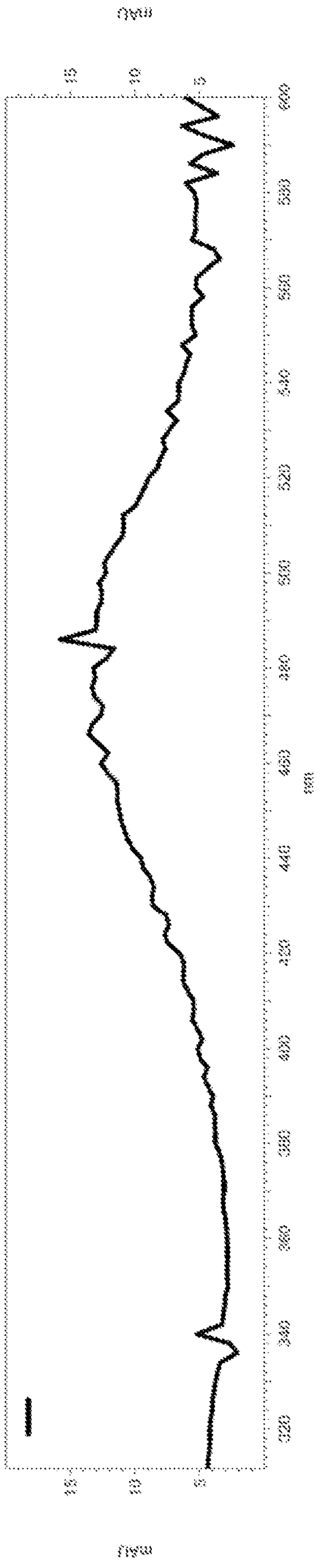
FIGURE 10. UV-Vis spectrum of the astaxanthin product peak.

SEQUENCE LISTING

<160> NUMBER OF SEQ ID NOS: 8

<210> SEQ ID NO 1
<211> LENGTH: 726
<212> TYPE: DNA
<213> ORGANISM: Unknown
<220> FEATURE:
<223> OTHER INFORMATION: Bacterium of the genus Brevundimonas
<220> FEATURE:
<221> NAME/KEY: Gene (crtW)
<222> LOCATION: (1)..(1)
<223> OTHER INFORMATION: Derived from Brevundimonas strain OB307

<400> SEQUENCE: 1
atgtccgccg tcacgccaat gtcacgggtc gtcccgaacc aggccctgat cggtctgacg 60
ctggctggcc tgatcgcgac ggcctggctg agcctgcata tctacggcgt ctattttcat 120
cgctggacga tgtggagcat cctgaccgtt ccgctaatcg tcgctttcca gacctggctg 180

-continued tccgtcggcc tgttcatcgt cgcccacgac gccatgcacg gctctctggc tccgggacgc 240
cctcggctga acacggcgat cggcagcctg gcgctgggcc tctacgccgg ttttcgtttt 300
gcgccgttga agacggcgca ccacgctcat catgccgcgc ccggcacggc ggacgacccc 360
gactttcacg ccgacgcccc gcgcgccttc ctgccctggt tctacggctt tttccgtacc 420
tatttcggtt ggcgcgagtt ggccgttctg acggtgctcg tggccgtcgc agtgctgatc 480
cttggcgccc gcatgcccaa tcttctggtc ttctgggccg cgcccgccct gctctcggcg 540
ctacagcttt tcacattcgg cacctggctg cctcacaggc ataccgacga cgccttcccc 600
gaccaccaca acgcccgcac cagccccttc ggcccgatcc tgtcgttgct gacctgcttc 660
cacttcggcc gccaccacga acaccacctg accccctgga agccctggtg gcgtcttttc 720
agctag 726

<210> SEQ ID NO 2
<211> LENGTH: 241
<212> TYPE: PRT
<213> ORGANISM: Unknown
<220> FEATURE:
<223> OTHER INFORMATION: Amino Acid Sequence
<220> FEATURE:
<221> NAME/KEY: misc_feature
<223> OTHER INFORMATION: Derived from Brevundimonas strain OB307 crtW
<220> FEATURE:
<221> NAME/KEY: misc_feature
<223> OTHER INFORMATION: Bacterium of the genus Brevundimonas

<400> SEQUENCE: 2

Met Ser Ala Val Thr Pro Met Ser Arg Val Val Pro Asn Gln Ala Leu
1 5 10 15

Ile Gly Leu Thr Leu Ala Gly Leu Ile Ala Thr Ala Trp Leu Ser Leu
20 25 30

His Ile Tyr Gly Val Tyr Phe His Arg Trp Thr Met Trp Ser Ile Leu
35 40 45

Thr Val Pro Leu Ile Val Ala Phe Gln Thr Trp Leu Ser Val Gly Leu
50 55 60

Phe Ile Val Ala His Asp Ala Met His Gly Ser Leu Ala Pro Gly Arg
65 70 75 80

Pro Arg Leu Asn Thr Ala Ile Gly Ser Leu Ala Leu Gly Leu Tyr Ala
85 90 95

Gly Phe Arg Phe Ala Pro Leu Lys Thr Ala His His Ala His His Ala
100 105 110

Ala Pro Gly Thr Ala Asp Asp Pro Asp Phe His Ala Asp Ala Pro Arg
115 120 125

Ala Phe Leu Pro Trp Phe Tyr Gly Phe Phe Arg Thr Tyr Phe Gly Trp
130 135 140

Arg Glu Leu Ala Val Leu Thr Val Leu Val Ala Val Ala Val Leu Ile
145 150 155 160

Leu Gly Ala Arg Met Pro Asn Leu Leu Val Phe Trp Ala Ala Pro Ala
165 170 175

Leu Leu Ser Ala Leu Gln Leu Phe Thr Phe Gly Thr Trp Leu Pro His
180 185 190

Arg His Thr Asp Asp Ala Phe Pro Asp His His Asn Ala Arg Thr Ser
195 200 205

Pro Phe Gly Pro Ile Leu Ser Leu Leu Thr Cys Phe His Phe Gly Arg
210 215 220

```
His His Glu His His Leu Thr Pro Trp Lys Pro Trp Trp Arg Leu Phe
225                 230                 235                 240

Ser


<210> SEQ ID NO 3
<211> LENGTH: 425
<212> TYPE: PRT
<213> ORGANISM: Unknown
<220> FEATURE:
<223> OTHER INFORMATION: Amino Acid Sequence
<220> FEATURE:
<221> NAME/KEY: misc_feature
<223> OTHER INFORMATION: Bacterium of the genus Brevundimonas

<400> SEQUENCE: 3

Met Leu Trp Ile Trp Asn Ala Leu Ile Val Phe Val Thr Val Ile Gly
1               5                   10                  15

Met Glu Val Val Ala Ala Leu Ala His Lys Tyr Ile Met His Gly Trp
            20                  25                  30

Gly Trp Gly Trp His Leu Ser His His Glu Pro Arg Lys Gly Ala Phe
        35                  40                  45

Glu Val Asn Asp Leu Tyr Ala Val Val Phe Ala Ala Leu Ser Ile Leu
    50                  55                  60

Leu Ile Tyr Leu Gly Ser Thr Gly Met Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His His Ala Val Arg Gly
        115                 120                 125

Lys Glu Gly Cys Val Ser Phe Gly Phe Leu Tyr Ala Pro Pro Leu Ser
    130                 135                 140

Lys Leu Gln Ala Thr Leu Arg Glu Arg His Gly Ala Arg Ala Gly Ala
145                 150                 155                 160

Ala Arg Asp Ala Gln Gly Gly Glu Asp Glu Pro Ala Ser Gly Lys Gly
                165                 170                 175

Gly Gly Gly Ser Gly Gly Pro Gly Ser Ser Ala Val Thr Pro Met Ser
            180                 185                 190

Arg Val Val Pro Asn Gln Ala Leu Ile Gly Leu Thr Leu Ala Gly Leu
        195                 200                 205

Ile Ala Thr Ala Trp Leu Ser Leu His Ile Tyr Gly Val Tyr Phe His
    210                 215                 220

Arg Trp Thr Met Trp Ser Ile Leu Thr Val Pro Leu Ile Val Ala Phe
225                 230                 235                 240

Gln Thr Trp Leu Ser Val Gly Leu Phe Ile Val Ala His Asp Ala Met
                245                 250                 255

His Gly Ser Leu Ala Pro Gly Arg Pro Arg Leu Asn Thr Ala Ile Gly
            260                 265                 270

Ser Leu Ala Leu Gly Leu Tyr Ala Gly Phe Arg Phe Ala Pro Leu Lys
        275                 280                 285

Thr Ala His His Ala His His Ala Ala Pro Gly Thr Ala Asp Asp Pro
    290                 295                 300

Asp Phe His Ala Asp Ala Pro Arg Ala Phe Leu Pro Trp Phe Tyr Gly
305                 310                 315                 320

Phe Phe Arg Thr Tyr Phe Gly Trp Arg Glu Leu Ala Val Leu Thr Val
```

```
            325                 330                 335

Leu Val Ala Val Ala Val Leu Ile Leu Gly Ala Arg Met Pro Asn Leu
            340                 345                 350

Leu Val Phe Trp Ala Ala Pro Ala Leu Leu Ser Ala Leu Gln Leu Phe
        355                 360                 365

Thr Phe Gly Thr Trp Leu Pro His Arg His Thr Asp Asp Ala Phe Pro
    370                 375                 380

Asp His His Asn Ala Arg Thr Ser Pro Phe Gly Pro Ile Leu Ser Leu
385                 390                 395                 400

Leu Thr Cys Phe His Phe Gly Arg His His Glu His His Leu Thr Pro
                405                 410                 415

Trp Lys Pro Trp Trp Arg Leu Phe Ser
            420                 425


<210> SEQ ID NO 4
<211> LENGTH: 1278
<212> TYPE: DNA
<213> ORGANISM: Unknown
<220> FEATURE:
<223> OTHER INFORMATION: Nucleic Acid Sequence
<220> FEATURE:
<221> NAME/KEY: misc_feature
<223> OTHER INFORMATION: Bacterium of the genus Brevundimonas

<400> SEQUENCE: 4

atgctgtgga tctggaacgc cctgatcgtt ttcgtgaccg tgatcggcat ggaagtggtg     60

gccgccctgg cccataagta catcatgcac ggctggggct ggggctggca cctgtcgcac    120

cacgaaccac gcaaaggcgc atttgaggtg aatgacctgt atgccgtggt gttcgccgcc    180

ctgtcgattc tgctgatcta tctgggctcg actggcatgt ggccgctgca gtggattggc    240

gccggcatga ccgcatacgg cctgctgtac tttatggttc atgacggcct ggtgcaccag    300

cgctggccgt tccgctacat cccgcgcaaa ggctatctga aacgcctgta catggcccac    360

cgcatgcacc atgcagtgcg cggcaaggag ggctgtgtgt cattcggctt tctgtacgcc    420

ccgccgctgt cgaagctgca ggccactctg cgcgagagac atggcgcccg cgccggcgca    480

gcccgcgatg cccaaggcgg cgaggacgag ccggcatcgg gcaaaggcgg gggcgggtcc    540

ggcggcccgg ggtcgtcggc cgtgaccccg atgtcgagag tggtgccaaa ccaggcccta    600

atcggcctga ctttagcggg gctgatagcc acggcgtggc tgagtctgca tatttacggg    660

gtgtacttcc atcgttggac aatgtggtcg atcctgacgg tgccgctgat cgtggccttc    720

cagacgtggc tgtcggtagg cctgttcatc gttgcccacg acgcaatgca cggctcccta    780

gccccgggga ggccccgcct gaacaccgcc atcgggtccc tggccctagg cctgtacgct    840

ggcttcaggt tcgcccctct gaagaccgcc caccatgccc accatgccgc accgggcaca    900

gccgacgacc cggattttca cgcggacgcc ccccgtgcgt tcctgccgtg gttctacggc    960

tttttccgta cctacttcgg ctggagggag ctggccgtgc tgaccgtgtt ggtggccgtg   1020

gctgttttaa tcctgggcgc ccgaatgccg aacttacttg tgttctgggc cgccccggct   1080

ctattatcgg ccttgcagct tttcaccttc ggcacatggc tgccgcaccg acacaccgac   1140

gacgccttcc cggaccacca caacgctcgc acttcaccct ttggccccat cctgtctctg   1200

ctgacctgct tccacttcgg ccggcaccat gagcaccacc tgactccgtg gaaaccgtgg   1260

tggaggctgt tctcgtag                                                  1278


<210> SEQ ID NO 5
```

<211> LENGTH: 6449
<212> TYPE: DNA
<213> ORGANISM: Unknown
<220> FEATURE:
<223> OTHER INFORMATION: Nucleic Acid Sequence
<220> FEATURE:
<221> NAME/KEY: misc_feature
<223> OTHER INFORMATION: Synthesized

<400> SEQUENCE: 5
agtccattgt tgccttgcaa cgcacgcgct gtcaatgcgg gaatccgcct cggcactgca 60
cgcttcccga cctaccggac ggtatgcagc gctcgcatct gccgaggccc cagagcatag 120
gcgagaagga tgaatttttg atgtacatcg tggccattgc tgcagagcgg atataaaaac 180
cgttattgac acaggtggaa atttaaaata tactgttagt aaacctaatg gatcgacctt 240
gaattcaaaa gatctgggag accacaacgg tttccctcta gaaataattt tggaattcaa 300
aagatctttt aagaaggaga tatacatatg gtgtcgggct cgaaggccgg cgtgtcgccg 360
caccgcgaga tcgaggtgat gcgccagtcg atcgacgacc acctggccgg cctgctgccg 420
gagaccgact cgcaggacat cgtgtcgctg gccatgcgcg agggcgtgat ggccccgggc 480
aagcgcatcc gcccgctgct gatgctgctg gccgcccgcg acctgcgcta ccagggctcg 540
atgccgaccc tgctggacct ggcctgcgcc gtggagctga cccacaccgc ctcgctgatg 600
ctggacgaca tgccgtgcat ggacaacgcc gagctgcgcc gcggccagcc gaccacccac 660
aagaagttcg gcgagtcggt ggccatcctg gcctcggtgg gcctgctgtc gaaggccttc 720
ggcctgatcg ccgccaccgg cgacctgccg ggcgagcgcc gcgcccaggc cgtgaacgag 780
ctgtcgaccg ccgtgggcgt gcagggcctg gtgctgggcc agttccgcga cctgaacgac 840
gccgccctgg accgcacccc ggacgccatc ctgtcgacca accacctgaa gaccggcatc 900
ctgttctcgg ccatgctgca gatcgtggcc atcgcctcgg cctcgtcgcc gtcgacccgc 960
gagaccctgc acgccttcgc cctggacttc ggccaggcct tccagctcct ggacgacctg 1020
cgcgacgacc acccggagac cggcaaggac cgcaacaagg acgccggcaa gtcgaccctg 1080
gtgaaccgcc tgggcgccga cgccgcccgc cagaagctgc gcgagcacat cgactcggcc 1140
gacaagcacc tgaccttcgc ctgcccgcag ggcggcgcca tccgccagtt catgcacctg 1200
tggttcggcc accacctggc cgactggtcg ccggtgatga agatcgcctg agtcatagct 1260
gtttcctgcc cagtcacgac gttgtaaaac gcaaaggaga tataggtgcg cgacctgatc 1320
ctggtgggcg gcggcctggc caacggcctg atcgcctggc gcctgcgcca gcgctacccg 1380
cagctcaacc tgctgctgat cgaggccggc gagcagccgg gcggcaacca cacctggtcg 1440
ttccacgagg acgacctgac ccgggccag cacgcctggc tggccccgct ggtggcccac 1500
gcctggccgg gctacgaggt gcagttcccg gacctgcgcc gccgcctggc ccgcggctac 1560
tactcgatca cctcggagcg cttcgccgag gccctgcacc aggccctggg cgagaacatc 1620
tggctgaact gctcggtgtc ggaggtgctg ccgaactcgg tgcgcctggc caacggcgag 1680
gccctgctgg ccggcgccgt gatcgacggc cgcggcgtga ccgcctcgtc ggccatgcag 1740
accggctacc agctcttcct gggccagcag tggcgcctga cccagccgca cggcctgacc 1800
gtgccgatcc tgatggacgc caccgtggcc cagcagcagg gctaccgctt cgtgtacacc 1860
ctgccgctgt cggccgacac cctgctgatc gaggacaccc gctacgccaa cgtgccgcag 1920
cgcgacgaca acgccctgcg ccagaccgtg accgactacg cccactcgaa gggctggcag 1980
ctcgcccagc tcgaacgcga ggagaccggc tgcctgccga tcaccctggc cggcgacatc 2040

-continued

```
caggccctgt gggccgacgc cccgggcgtg ccgcgctcgg gcatgcgcgc cggcctgttc   2100
cacccgacca ccggctactc gctgccgctg gccgtggccc tggccgacgc catcgccgac   2160
tcgccgcgcc tgggctcggt gccgctgtac cagctcaccc gccagttcgc cgagcgccac   2220
tggcgccgcc agggcttctt ccgcctgctg aaccgcatgc tgttcctggc cggccgcgag   2280
gagaaccgct ggcgcgtgat gcagcgcttc tacggcctgc cggagccgac cgtggagcgc   2340
ttctacgccg gccgcctgtc gctgttcgac aaggcccgca tcctgaccgg caagccgccg   2400
gtgccgctgg gcgaggcctg ccgcgccgcc ctgaaccact tcccggaccg ccgcgacaag   2460
ggctgacctg tgtgaaattg ttatccgctt acccatacga cgtcccagac aaaggagata   2520
tagatgaaga agaccgtggt gatcggcgcc ggcttcggcg gcctggccct ggccatccgc   2580
ctgcaggccg ccggcatccc gaccgtgctg ctggagcagc gcgacaagcc gggcggccgc   2640
gcctacgtgt ggcacgacca gggcttcacc ttcgacgccg gcccgaccgt gatcaccgac   2700
ccgaccgccc tggaggccct gttcaccctg gccggccgcc gcatggagga ctacgtgcgc   2760
ctgctgccgg tgaagccgtt ctaccgcctg tgctgggagt cgggcaagac cctggactac   2820
gccaacgact cggccgagct ggaggcccag atcacccagt tcaacccgcg cgacgtggag   2880
ggctaccgcc gcttcctggc ctactcgcag gccgtgttcc aggagggcta cctgcgcctg   2940
ggctcggtgc cgttcctgtc gttccgcgac atgctgcgcg ccggcccgca gctcctgaag   3000
ctgcaggcct ggcagtcggt gtaccagtcg gtgtcgcgct tcatcgagga cgagcacctg   3060
cgccaggcct tctcgttcca ctcgctgctg gtgggcggca acccgttcac cacctcgtcg   3120
atctacaccc tgatccacgc cctggagcgc gagtggggcg tgtggttccc ggagggcggc   3180
accggcgccc tggtgaacgg catggtgaag ctgttcaccg acctgggcgg cgagatcgag   3240
ctgaacgccc gcgtggagga gctggtggtg gccgacaacc gcgtgtcgca ggtgcgcctg   3300
gccgacggcc gcatcttcga caccgacgcc gtggcctcga acgccgacgt ggtgaacacc   3360
tacaagaagc tgctgggcca ccacccggtg ggccagaagc gcgccgccgc cctggagcgc   3420
aagtcgatgt cgaactcgct gttcgtgctg tacttcggcc tgaaccagcc gcactcgcag   3480
ctcgcccacc acaccatctg cttcggcccg cgctaccgcg agctgatcga cgagatcttc   3540
accggctcgg ccctggccga cgacttctcg ctgtacctgc actcgccgtg cgtgaccgac   3600
ccgtcgctgg ccccgccggg ctgcgcctcg ttctacgtgc tggccccggt gccgcacctg   3660
ggcaacgccc cgctggactg ggcccaggag ggcccgaagc tgcgcgaccg catcttcgac   3720
tacctggagg agcgctacat gccgggcctg cgctcgcagc tcgtgaccca gcgcatcttc   3780
accccggccg acttccacga caccctggac gcccacctgg gctcggcctt ctcgatcgag   3840
ccgctgctga cccagtcggc ctggttccgc ccgcacaacc gcgactcgga catcgccaac   3900
ctgtacctgg tgggcgccgg cacccacccg ggcgccggca tcccgggcgt ggtggcctcg   3960
gccaaggcca ccgcctcgct gatgatcgag gacctgcagt gatctgggac gtcgtatggg   4020
taagctggac atcacctccc acaacgcaaa ggagatatag atgtcgcagc cgccgctgct   4080
ggaccacgcc acccagacca tggccaacgg ctcgaagtcg ttcgccaccg ccgccaagct   4140
gttcgacccg gccacccgcc gctcggtgct gatgctgtac acctggtgcc gccactgcga   4200
cgacgtgatc gacgaccaga cccacggctt cgcctcggag gccgccgccg aggaggaggc   4260
cacccagcgc ctggcccgcc tgcgcaccct gaccctggcc gccttcgagg gcgccgagat   4320
gcaggacccg gccttcgccg ccttccagga ggtggccctg acccacggca tcaccccgcg   4380
catggccctg gaccacctgg acggcttcgc catggacgtg gcccagaccc gctacgtgac   4440
```

-continued cttcgaggac accctgcgct actgctacca cgtggccggc gtggtgggcc tgatgatggc 4500
ccgcgtgatg ggcgtgcgcg acgagcgcgt gctggaccgc gcctgcgacc tgggcctggc 4560
cttccagctc accaacatcg cccgcgacat catcgacgac gccgccatcg accgctgcta 4620
cctgccggcc gagtggctgc aggacgccgg cctgaccccg gagaactacg ccgcccgcga 4680
gaaccgcgcc gccctggccc gcgtggccga gcgcctgatc gacgccgccg agccgtacta 4740
catctcgtcg caggccggcc tgcacgacct gccgccgcgc tgcgcctggg ccatcgccac 4800
cgcccgctcg gtgtaccgcg agatcggcat caaggtgaag gccgccggcg gctcggcctg 4860
ggaccgccgc cagcacacct cgaagggcga gaagatcgcc atgctgatgg ccgccccggg 4920
ccaggtgatc cgcgccaaga ccacccgcgt gaccccgcgc ccggccggcc tgtggcagcg 4980
cccggtgtga ctgtcccccc agttccagta cctggtcatc atcctgcctt tcaaaggaga 5040
tatagatgct gtggatctgg aacgccctga tcgtgttcgt gaccgtgatc ggcatggagg 5100
tggtggccgc cctggcccac aagtacatca tgcacggctg ggctggggc tggcacctgt 5160 cgcaccacga gccgcgcaag ggcgccttcg aggtgaacga cctgtacgcc gtggtgttcg 5220
ccgccctgtc gatcctgctg atctacctgg gctcgaccgg catgtggccg ctgcagtgga 5280
tcggcgccgg catgaccgcc tacggcctgc tgtacttcat ggtgcacgac ggcctggtgc 5340
accagcgctg gccgttccgc tacatcccgc gcaagggcta cctgaagcgc ctgtacatgg 5400
cccaccgcat gcaccacgcc gtgcgcggca aggagggctg cgtgtcgttc ggcttcctgt 5460
acgccccgcc gctgtcgaag ctgcaggcca ccctgcgcga gcgccacggc gcccgcgccg 5520
gcgccgcccg cgacgcccag ggcggcgagg acgagccggc ctcgggcaag tgagttatat 5580
ggagggggca aacgctctag aactagtgga tccaaaggag atatagatgt cggccgtgac 5640
cccgatgtcg agagtggtgc caaaccaggc cctaatcggc ctgactttag cggggctgat 5700
agccacggcg tggctgagtc tgcatattta cggggtgtac ttccatcgtt ggacaatgtg 5760
gtcgatcctg acggtgccgc tgatcgtggc cttccagacg tggctgtcgg taggcctgtt 5820
catcgttgcc cacgacgcaa tgcacggctc cctagccccg gggaggcccc gcctgaacac 5880
cgccatcggg tccctggccc taggcctgta cgctggcttc aggttcgccc ctctgaagac 5940
cgcccaccat gcccaccatg ccgcaccggg cacagccgac gacccggatt ttcacgcgga 6000
cgccccccgt gcgttcctgc cgtggttcta cggctttttc cgtacctact tcggctggag 6060
ggagctggcc gtgctgaccg tgttggtggc cgtggctgtt ttaatcctgg gcgcccgaat 6120
gccgaactta cttgtgttct gggccgcccc ggctctatta tcggccttgc agcttttcac 6180
cttcggcaca tggctgccgc accgacacac cgacgacgcc ttcccggacc accacaacgc 6240
tcgcacttca ccctttggcc ccatcctgtc tctgctgacc tgcttccact tcggccggca 6300
ccatgagcac cacctgactc cgtggaaacc gtggtggagg ctgttctcgt agcgataccg 6360
tcgacttcga gcaaataaaa cgaaaggctc agtcgaaaga ctgggccttt cgttttatct 6420
gttgtttgtc ggtgaacgct ctcattaat 6449

<210> SEQ ID NO 6
<211> LENGTH: 5867
<212> TYPE: DNA
<213> ORGANISM: Unknown
<220> FEATURE:
<223> OTHER INFORMATION: Nucleic Acid Sequence
<220> FEATURE:
<221> NAME/KEY: misc_feature
<223> OTHER INFORMATION: Synthesized -continued

<400> SEQUENCE: 6
agtccattgt tgccttgcaa cgcacgcgct gtcaatgcgg gaatccgcct cggcactgca 60
cgcttcccga cctaccggac ggtatgcagc gctcgcatct gccgaggccc cagagcatag 120
gcgagaagga tgaatttttg atgtacatcg tggccattgc tgcagagcgg atataaaaac 180
cgttattgac acaggtggaa atttaaaata tactgttagt aaacctaatg gatcgacctt 240
gaattcaaaa gatctgggag accacaacgg tttccctcta gaaataattt tggaattcaa 300
aagatctttt aagaaggaga tatacatatg gtgtcgggct cgaaggccgg cgtgtcgccg 360
caccgcgaga tcgaggtgat gcgccagtcg atcgacgacc acctggccgg cctgctgccg 420
gagaccgact cgcaggacat cgtgtcgctg gccatgcgcg agggcgtgat ggcccccggc 480
aagcgcatcc gcccgctgct gatgctgctg gccgcccgcg acctgcgcta ccagggctcg 540
atgccgaccc tgctggacct ggcctgcgcc gtggagctga cccacaccgc ctcgctgatg 600
ctggacgaca tgccgtgcat ggacaacgcc gagctgcgcc gcggccagcc gaccacccac 660
aagaagttcg gcgagtcggt ggccatcctg gcctcggtgg gcctgctgtc gaaggccttc 720
ggcctgatcg ccgccaccgg cgacctgccg ggcgagcgcc gcgcccaggc cgtgaacgag 780
ctgtcgaccg ccgtgggcgt gcagggcctg gtgctgggcc agttccgcga cctgaacgac 840
gccgccctgg accgcacccc ggacgccatc ctgtcgacca accacctgaa gaccggcatc 900
ctgttctcgg ccatgctgca gatcgtggcc atcgcctcgg cctcgtcgcc gtcgacccgc 960
gagaccctgc acgccttcgc cctggacttc ggccaggcct tccagctcct ggacgacctg 1020
cgcgacgacc acccggagac cggcaaggac cgcaacaagg acgccggcaa gtcgaccctg 1080
gtgaaccgcc tgggcgccga cgccgcccgc cagaagctgc gcgagcacat cgactcggcc 1140
gacaagcacc tgaccttcgc ctgcccgcag ggcggcgcca tccgccagtt catgcacctg 1200
tggttcggcc accacctggc cgactggtcg ccggtgatga agatcgcctg agtcatagct 1260
gtttcctgcc cagtcacgac gttgtaaaac gcaaaggaga tataggtgcg cgacctgatc 1320
ctggtgggcg gcggcctggc caacggcctg atcgcctggc gcctgcgcca gcgctacccg 1380
cagctcaacc tgctgctgat cgaggccggc gagcagccgg gcggcaacca cacctggtcg 1440
ttccacgagg acgacctgac ccgggccag cacgcctggc tggccccgct ggtggcccac 1500
gcctggccgg gctacgaggt gcagttcccg gacctgcgcc gccgcctggc ccgcggctac 1560
tactcgatca cctcggagcg cttcgccgag gccctgcacc aggccctggg cgagaacatc 1620
tggctgaact gctcggtgtc ggaggtgctg ccgaactcgg tgcgcctggc caacggcgag 1680
gccctgctgg ccggcgccgt gatcgacggc cgcggcgtga ccgcctcgtc ggccatgcag 1740
accggctacc agctcttcct gggccagcag tggcgcctga cccagccgca cggcctgacc 1800
gtgccgatcc tgatggacgc caccgtggcc cagcagcagg gctaccgctt cgtgtacacc 1860
ctgccgctgt cggccgacac cctgctgatc gaggacaccc gctacgccaa cgtgccgcag 1920
cgcgacgaca acgccctgcg ccagaccgtg accgactacg cccactcgaa gggctggcag 1980
ctcgcccagc tcgaacgcga ggagaccggc tgcctgccga tcaccctggc cggcgacatc 2040
caggccctgt gggccgacgc cccgggcgtg ccgcgctcgg gcatgcgcgc cggcctgttc 2100
cacccgacca ccggctactc gctgccgctg gccgtggccc tggccgacgc catcgccgac 2160
tcgccgcgcc tgggctcggt gccgctgtac cagctcaccc gccagttcgc cgagcgccac 2220
tggcgccgcc agggcttctt ccgcctgctg aaccgcatgc tgttcctggc cggccgcgag 2280

-continued

```
gagaaccgct ggcgcgtgat gcagcgcttc tacggcctgc cggagccgac cgtggagcgc   2340
ttctacgccg gccgcctgtc gctgttcgac aaggcccgca tcctgaccgg caagccgccg   2400
gtgccgctgg gcgaggcctg ccgcgccgcc ctgaaccact tcccggaccg ccgcgacaag   2460
ggctgacctg tgtgaaattg ttatccgctt acccatacga cgtcccagac aaaggagata   2520
tagatgaaga agaccgtggt gatcggcgcc ggcttcggcg gcctggccct ggccatccgc   2580
ctgcaggccg ccggcatccc gaccgtgctg ctggagcagc gcgacaagcc gggcggccgc   2640
gcctacgtgt ggcacgacca gggcttcacc ttcgacgccg gcccgaccgt gatcaccgac   2700
ccgaccgccc tggaggccct gttcaccctg gccggccgcc gcatggagga ctacgtgcgc   2760
ctgctgccgg tgaagccgtt ctaccgcctg tgctgggagt cgggcaagac cctggactac   2820
gccaacgact cggccgagct ggaggcccag atcacccagt tcaacccgcg cgacgtggag   2880
ggctaccgcc gcttcctggc ctactcgcag gccgtgttcc aggagggcta cctgcgcctg   2940
ggctcggtgc cgttcctgtc gttccgcgac atgctgcgcg ccggcccgca gctcctgaag   3000
ctgcaggcct ggcagtcggt gtaccagtcg gtgtcgcgct tcatcgagga cgagcacctg   3060
cgccaggcct tctcgttcca ctcgctgctg gtgggcggca acccgttcac cacctcgtcg   3120
atctacaccc tgatccacgc cctggagcgc gagtggggcg tgtggttccc ggagggcggc   3180
accggcgccc tggtgaacgg catggtgaag ctgttcaccg acctgggcgg cgagatcgag   3240
ctgaacgccc gcgtggagga gctggtggtg gccgacaacc gcgtgtcgca ggtgcgcctg   3300
gccgacggcc gcatcttcga caccgacgcc gtggcctcga acgccgacgt ggtgaacacc   3360
tacaagaagc tgctgggcca ccacccggtg ggccagaagc gcgccgccgc cctggagcgc   3420
aagtcgatgt cgaactcgct gttcgtgctg tacttcggcc tgaaccagcc gcactcgcag   3480
ctcgcccacc acaccatctg cttcggcccg cgctaccgcg agctgatcga cgagatcttc   3540
accggctcgg ccctggccga cgacttctcg ctgtacctgc actcgccgtg cgtgaccgac   3600
ccgtcgctgg ccccgccggg ctgcgcctcg ttctacgtgc tggccccggt gccgcacctg   3660
ggcaacgccc cgctggactg ggcccaggag ggcccgaagc tgcgcgaccg catcttcgac   3720
tacctggagg agcgctacat gccgggcctg cgctcgcagc tcgtgaccca gcgcatcttc   3780
accccggccg acttccacga caccctggac gcccacctgg gctcggcctt ctcgatcgag   3840
ccgctgctga cccagtcggc ctggttccgc ccgcacaacc gcgactcgga catcgccaac   3900
ctgtacctgg tgggcgccgg cacccacccg ggcgccggca tcccgggcgt ggtggcctcg   3960
gccaaggcca ccgcctcgct gatgatcgag gacctgcagt gatctgggac gtcgtatggg   4020
taagctggac atcacctccc acaacgcaaa ggagatatag atgtcgcagc cgccgctgct   4080
ggaccacgcc acccagacca tggccaacgg ctcgaagtcg ttcgccaccg ccgccaagct   4140
gttcgacccg gccacccgcc gctcggtgct gatgctgtac acctggtgcc gccactgcga   4200
cgacgtgatc gacgaccaga cccacggctt cgcctcggag gccgccgccg aggaggaggc   4260
cacccagcgc ctggcccgcc tgcgcaccct gaccctggcc gccttcgagg gcgccgagat   4320
gcaggacccg gccttcgccg ccttccagga ggtggccctg acccacggca tcaccccgcg   4380
catggccctg gaccacctgg acggcttcgc catggacgtg gcccagaccc gctacgtgac   4440
cttcgaggac accctgcgct actgctacca cgtggccggc gtggtgggcc tgatgatggc   4500
ccgcgtgatg ggcgtgcgcg acgagcgcgt gctggaccgc gcctgcgacc tgggcctggc   4560
cttccagctc accaacatcg cccgcgacat catcgacgac gccgccatcg accgctgcta   4620
cctgccggcc gagtggctgc aggacgccgg cctgaccccg gagaactacg ccgcccgcga   4680
```

gaaccgcgcc gccctggccc gcgtggccga gcgcctgatc gacgccgccg agccgtacta 4740
catctcgtcg caggccggcc tgcacgacct gccgccgcgc tgcgcctggg ccatcgccac 4800
cgcccgctcg gtgtaccgcg agatcggcat caaggtgaag gccgccggcg gctcggcctg 4860
ggaccgccgc cagcacacct cgaagggcga gaagatcgcc atgctgatgg ccgccccggg 4920
ccaggtgatc cgcgccaaga ccacccgcgt gaccccgcgc ccggccggcc tgtggcagcg 4980
cccggtgtga ctgtccccgt tatatggagg gggcaaacgc tctagaacta gtggatccaa 5040
aggagatata gatgtcggcc gtgaccccga tgtcgagagt ggtgccaaac caggccctaa 5100
tcggcctgac tttagcgggg ctgatagcca cggcgtggct gagtctgcat atttacgggg 5160
tgtacttcca tcgttggaca atgtggtcga tcctgacggt gccgctgatc gtggccttcc 5220
agacgtggct gtcggtaggc ctgttcatcg ttgcccacga cgcaatgcac ggctccctag 5280
ccccggggag gccccgcctg aacaccgcca tcgggtccct ggccctaggc ctgtacgctg 5340
gcttcaggtt cgcccctctg aagaccgccc accatgccca ccatgccgca ccgggcacag 5400
ccgacgaccc ggattttcac gcggacgccc cccgtgcgtt cctgccgtgg ttctacggct 5460
ttttccgtac ctacttcggc tggagggagc tggccgtgct gaccgtgttg gtggccgtgg 5520
ctgttttaat cctgggcgcc cgaatgccga acttacttgt gttctgggcc gccccggctc 5580
tattatcggc cttgcagctt ttcaccttcg gcacatggct gccgcaccga cacaccgacg 5640
acgccttccc ggaccaccac aacgctcgca cttcaccctt tggccccatc ctgtctctgc 5700
tgacctgctt ccacttcggc cggcaccatg agcaccacct gactccgtgg aaaccgtggt 5760
ggaggctgtt ctcgtagcga taccgtcgac ttcgagcaaa taaaacgaaa ggctcagtcg 5820
aaagactggg cctttcgttt tatctgttgt ttgtcggtga acgctct 5867

<210> SEQ ID NO 7
<211> LENGTH: 6462
<212> TYPE: DNA
<213> ORGANISM: Unknown
<220> FEATURE:
<223> OTHER INFORMATION: Nucleic Acid Sequence
<220> FEATURE:
<221> NAME/KEY: misc_feature
<223> OTHER INFORMATION: Synthesized

<400> SEQUENCE: 7
agtccattgt tgccttgcaa cgcacgcgct gtcaatgcgg gaatccgcct cggcactgca 60
cgcttcccga cctaccggac ggtatgcagc gctcgcatct gccgaggccc cagagcatag 120
gcgagaagga tgaatttttg atgtacatcg tggccattgc tgcagagcgg atataaaaac 180
cgttattgac acaggtggaa atttaaaata tactgttagt aaacctaatg gatcgacctt 240
gaattcaaaa gatctgggag accacaacgg tttccctcta gaaataattt tggaattcaa 300
aagatctttt aagaaggaga tatacatatg gtgtcgggct cgaaggccgg cgtgtcgccg 360
caccgcgaga tcgaggtgat gcgccagtcg atcgacgacc acctggccgg cctgctgccg 420
gagaccgact cgcaggacat cgtgtcgctg gccatgcgcg agggcgtgat ggccccgggc 480
aagcgcatcc gcccgctgct gatgctgctg gccgcccgcg acctgcgcta ccagggctcg 540
atgccgaccc tgctggacct ggcctgcgcc gtggagctga cccacaccgc ctcgctgatg 600
ctggacgaca tgccgtgcat ggacaacgcc gagctgcgcc gcggccagcc gaccacccac 660
aagaagttcg gcgagtcggt ggccatcctg gcctcggtgg gcctgctgtc gaaggccttc 720
ggcctgatcg ccgccaccgg cgacctgccg ggcgagcgcc gcgcccaggc cgtgaacgag 780

-continued

```
ctgtcgaccg ccgtgggcgt gcagggcctg gtgctgggcc agttccgcga cctgaacgac    840
gccgccctgg accgcacccc ggacgccatc ctgtcgacca accacctgaa gaccggcatc    900
ctgttctcgg ccatgctgca gatcgtggcc atcgcctcgg cctcgtcgcc gtcgacccgc    960
gagaccctgc acgccttcgc cctggacttc ggccaggcct tccagctcct ggacgacctg   1020
cgcgacgacc acccggagac cggcaaggac cgcaacaagg acgccggcaa gtcgaccctg   1080
gtgaaccgcc tgggcgccga cgccgcccgc cagaagctgc gcgagcacat cgactcggcc   1140
gacaagcacc tgaccttcgc ctgcccgcag ggcggcgcca tccgccagtt catgcacctg   1200
tggttcggcc accacctggc cgactggtcg ccggtgatga agatcgcctg agtcatagct   1260
gtttcctgcc cagtcacgac gttgtaaaac gcaaaggaga tataggtgcg cgacctgatc   1320
ctggtgggcg gcggcctggc caacggcctg atcgcctggc gcctgcgcca gcgctacccg   1380
cagctcaacc tgctgctgat cgaggccggc gagcagccgg gcggcaacca cacctggtcg   1440
ttccacgagg acgacctgac ccgggccag cacgcctggc tggccccgct ggtggcccac    1500
gcctggccgg gctacgaggt gcagttcccg gacctgcgcc gccgcctggc ccgcggctac   1560
tactcgatca cctcggagcg cttcgccgag gccctgcacc aggccctggg cgagaacatc   1620
tggctgaact gctcggtgtc ggaggtgctg ccgaactcgg tgcgcctggc caacggcgag   1680
gccctgctgg ccggcgccgt gatcgacggc cgcggcgtga ccgcctcgtc ggccatgcag   1740
accggctacc agctcttcct gggccagcag tggcgcctga cccagccgca cggcctgacc   1800
gtgccgatcc tgatggacgc caccgtggcc cagcagcagg gctaccgctt cgtgtacacc   1860
ctgccgctgt cggccgacac cctgctgatc gaggacaccc gctacgccaa cgtgccgcag   1920
cgcgacgaca acgccctgcg ccagaccgtg accgactacg cccactcgaa gggctggcag   1980
ctcgcccagc tcgaacgcga ggagaccggc tgcctgccga tcaccctggc cggcgacatc   2040
caggccctgt gggccgacgc cccgggcgtg ccgcgctcgg gcatgcgcgc cggcctgttc   2100
cacccgacca ccggctactc gctgccgctg gccgtggccc tggccgacgc catcgccgac   2160
tcgccgcgcc tgggctcggt gccgctgtac cagctcaccc gccagttcgc cgagcgccac   2220
tggcgccgcc agggcttctt ccgcctgctg aaccgcatgc tgttcctggc cggccgcgag   2280
gagaaccgct ggcgcgtgat gcagcgcttc tacggcctgc cggagccgac cgtggagcgc   2340
ttctacgccg gccgcctgtc gctgttcgac aaggcccgca tcctgaccgg caagccgccg   2400
gtgccgctgg gcgaggcctg ccgcgccgcc ctgaaccact tcccggaccg ccgcgacaag   2460
ggctgacctg tgtgaaattg ttatccgctt acccatacga cgtcccagac aaaggagata   2520
tagatgaaga agaccgtggt gatcggcgcc ggcttcggcg gcctggccct ggccatccgc   2580
ctgcaggccg ccggcatccc gaccgtgctg ctggagcagc gcgacaagcc gggcggccgc   2640
gcctacgtgt ggcacgacca gggcttcacc ttcgacgccg gcccgaccgt gatcaccgac   2700
ccgaccgccc tggaggccct gttcaccctg gccggccgcc gcatggagga ctacgtgcgc   2760
ctgctgccgg tgaagccgtt ctaccgcctg tgctgggagt cgggcaagac cctggactac   2820
gccaacgact cggccgagct ggaggcccag atcacccagt tcaacccgcg cgacgtggag   2880
ggctaccgcc gcttcctggc ctactcgcag gccgtgttcc aggagggcta cctgcgcctg   2940
ggctcggtgc cgttcctgtc gttccgcgac atgctgcgcg ccggcccgca gctcctgaag   3000
ctgcaggcct ggcagtcggt gtaccagtcg gtgtcgcgct tcatcgagga cgagcacctg   3060
cgccaggcct tctcgttcca ctcgctgctg gtgggcggca acccgttcac cacctcgtcg   3120
```

-continued

```
atctacaccc tgatccacgc cctggagcgc gagtggggcg tgtggttccc ggagggcggc   3180
accggcgccc tggtgaacgg catggtgaag ctgttcaccg acctgggcgg cgagatcgag   3240
ctgaacgccc gcgtggagga gctggtggtg gccgacaacc gcgtgtcgca ggtgcgcctg   3300
gccgacggcc gcatcttcga caccgacgcc gtggcctcga acgccgacgt ggtgaacacc   3360
tacaagaagc tgctgggcca ccacccggtg ggccagaagc gcgccgccgc cctggagcgc   3420
aagtcgatgt cgaactcgct gttcgtgctg tacttcggcc tgaaccagcc gcactcgcag   3480
ctcgcccacc acaccatctg cttcggcccg cgctaccgcg agctgatcga cgagatcttc   3540
accggctcgg ccctggccga cgacttctcg ctgtacctgc actcgccgtg cgtgaccgac   3600
ccgtcgctgg ccccgccggg ctgcgcctcg ttctacgtgc tggccccggt gccgcacctg   3660
ggcaacgccc cgctggactg ggcccaggag ggcccgaagc tgcgcgaccg catcttcgac   3720
tacctggagg agcgctacat gccgggcctg cgctcgcagc tcgtgaccca gcgcatcttc   3780
accccggccg acttccacga caccctggac gcccacctgg gctcggcctt ctcgatcgag   3840
ccgctgctga cccagtcggc ctggttccgc ccgcacaacc gcgactcgga catcgccaac   3900
ctgtacctgg tgggcgccgg cacccacccg ggcgccggca tcccgggcgt ggtggcctcg   3960
gccaaggcca ccgcctcgct gatgatcgag gacctgcagt gatctgggac gtcgtatggg   4020
taagctggac atcacctccc acaacgcaaa ggagatatag atgtcgcagc cgccgctgct   4080
ggaccacgcc acccagacca tggccaacgg ctcgaagtcg ttcgccaccg ccgccaagct   4140
gttcgacccg gccacccgcc gctcggtgct gatgctgtac acctggtgcc gccactgcga   4200
cgacgtgatc gacgaccaga cccacggctt cgcctcggag gccgccgccg aggaggaggc   4260
cacccagcgc ctggcccgcc tgcgcaccct gaccctggcc gccttcgagg gcgccgagat   4320
gcaggacccg gccttcgccg ccttccagga ggtggccctg acccacggca tcaccccgcg   4380
catggccctg gaccacctgg acggcttcgc catggacgtg gcccagaccc gctacgtgac   4440
cttcgaggac accctgcgct actgctacca cgtggccggc gtggtgggcc tgatgatggc   4500
ccgcgtgatg ggcgtgcgcg acgagcgcgt gctggaccgc gcctgcgacc tgggcctggc   4560
cttccagctc accaacatcg cccgcgacat catcgacgac gccgccatcg accgctgcta   4620
cctgccggcc gagtggctgc aggacgccgg cctgaccccg gagaactacg ccgcccgcga   4680
gaaccgcgcc gccctggccc gcgtggccga gcgcctgatc gacgccgccg agccgtacta   4740
catctcgtcg caggccggcc tgcacgacct gccgccgcgc tgcgcctggg ccatcgccac   4800
cgcccgctcg gtgtaccgcg agatcggcat caaggtgaag gccgccggcg gctcggcctg   4860
ggaccgccgc cagcacacct cgaagggcga gaagatcgcc atgctgatgg ccgccccggg   4920
ccaggtgatc cgcgccaaga ccacccgcgt gaccccgcgc ccggccggcc tgtggcagcg   4980
cccggtgtga ctgtccccgt tatatggagg gggcaaacgc tctagaacta gtggatccct   5040
gtcccccag ttccagtacc tggtcatcat cctgcctttc aaaggagata tagatgctgt   5100
ggatctggaa cgccctgatc gttttcgtga ccgtgatcgg catggaagtg gtggccgccc   5160
tggcccataa gtacatcatg cacggctggg gctggggctg gcacctgtcg caccacgaac   5220
cacgcaaagg cgcatttgag gtgaatgacc tgtatgccgt ggtgttcgcc gccctgtcga   5280
ttctgctgat ctatctgggc tcgactggca tgtggccgct gcagtggatt ggcgccggca   5340
tgaccgcata cggcctgctg tactttatgg ttcatgacgg cctggtgcac cagcgctggc   5400
cgttccgcta catcccgcgc aaaggctatc tgaaacgcct gtacatggcc caccgcatgc   5460
accatgcagt gcgcggcaag gagggctgtg tgtcattcgg ctttctgtac gccccgccgc   5520
```

```
tgtcgaagct gcaggccact ctgcgcgaga gacatggcgc ccgcgccggc gcagcccgcg   5580
atgcccaagg cggcgaggac gagccggcat cgggcaaagg cgggggcggg tccggcggcc   5640
cggggtcgtc ggccgtgacc ccgatgtcga gagtggtgcc aaaccaggcc ctaatcggcc   5700
tgactttagc ggggctgata gccacggcgt ggctgagtct gcatatttac ggggtgtact   5760
tccatcgttg gacaatgtgg tcgatcctga cggtgccgct gatcgtggcc ttccagacgt   5820
ggctgtcggt aggcctgttc atcgttgccc acgacgcaat gcacggctcc ctagccccgg   5880
ggaggccccg cctgaacacc gccatcgggt ccctggccct aggcctgtac gctggcttca   5940
ggttcgcccc tctgaagacc gcccaccatg cccaccatgc cgcaccgggc acagccgacg   6000
acccggattt tcacgcggac gccccccgtg cgttcctgcc gtggttctac ggctttttcc   6060
gtacctactt cggctggagg gagctggccg tgctgaccgt gttggtggcc gtggctgttt   6120
taatcctggg cgcccgaatg ccgaacttac ttgtgttctg ggccgccccg gctctattat   6180
cggccttgca gcttttcacc ttcggcacat ggctgccgca ccgacacacc gacgacgcct   6240
tcccggacca ccacaacgct cgcacttcac cctttggccc catcctgtct ctgctgacct   6300
gcttccactt cggccggcac catgagcacc acctgactcc gtggaaaccg tggtggaggc   6360
tgttctcgta gcgataccgt cgacttcgag caaataaaac gaaaggctca gtcgaaagac   6420
tgggcctttc gttttatctg ttgtttgtcg gtgaacgctc tc                       6462
```

<210> SEQ ID NO 8
<211> LENGTH: 8861
<212> TYPE: DNA
<213> ORGANISM: Unknown
<220> FEATURE:
<223> OTHER INFORMATION: Nucleic Acid Sequence
<220> FEATURE:
<221> NAME/KEY: misc_feature
<223> OTHER INFORMATION: Synthesized

<400> SEQUENCE: 8

```
caaataatga ttttattttg actgatagtg acctgttcgt tgcaacamat tgatgagcaa     60
tgctttttta taatgccaac tttgtacaaa aaagcaggct tcaggccgag gcctgtctct    120
tatacacatc tttgtgtctc aggccgccta ggccgcggcc gcgcgaattc gagctcggta    180
cccggggatc ctctagagtc gacctgcagg catgcaagct taccggttta ttattaagtc    240
cattgttgcc ttgcaacgca cgcgctgtca atgcgggaat ccgcctcggc actgcacgct    300
tcccgaccta ccggacggta tgcagcgctc gcatctgccg aggccccaga gcataggcga    360
gaaggatgaa tttttgatgt acatcgtggc cattgctgca gagcggatat aaaaaccgtt    420
attgacacag gtggaaattt aaaatatact gttagtaaac ctaatggatc gaccttgaat    480
tcaaaagatc tgggagacca caacggtttc cctctagaaa taattttgga attcaaaaga    540
tcttttaaga aggagatata catatggtgt cgggctcgaa ggccggcgtg tcgccgcacc    600
gcgagatcga ggtgatgcgc cagtcgatcg acgaccacct ggccggcctg ctgccggaga    660
ccgactcgca ggacatcgtg tcgctggcca tgcgcgaggg cgtgatggcc ccgggcaagc    720
gcatccgccc gctgctgatg ctgctggccg cccgcgacct gcgctaccag ggctcgatgc    780
cgaccctgct ggacctggcc tgcgccgtgg agctgaccca caccgcctcg ctgatgctgg    840
acgacatgcc gtgcatggac aacgccgagc tgcgccgcgg ccagccgacc acccacaaga    900
agttcggcga gtcggtggcc atcctggcct cggtgggcct gctgtcgaag gccttcggcc    960
tgatcgccgc caccggcgac ctgccgggcg agcgccgcgc ccaggccgtg aacgagctgt   1020
```

-continued

```
cgaccgccgt gggcgtgcag ggcctggtgc tgggccagtt ccgcgacctg aacgacgccg   1080
ccctggaccg caccccggac gccatcctgt cgaccaacca cctgaagacc ggcatcctgt   1140
tctcggccat gctgcagatc gtggccatcg cctcggcctc gtcgccgtcg acccgcgaga   1200
ccctgcacgc cttcgccctg gacttcggcc aggccttcca gctcctggac gacctgcgcg   1260
acgaccaccc ggagaccggc aaggaccgca acaaggacgc cggcaagtcg accctggtga   1320
accgcctggg cgccgacgcc gcccgccaga agctgcgcga gcacatcgac tcggccgaca   1380
agcacctgac cttcgcctgc ccgcagggcg gcgccatccg ccagttcatg cacctgtggt   1440
tcggccacca cctggccgac tggtcgccgg tgatgaagat cgcctgagtc atagctgttt   1500
cctgcccagt cacgacgttg taaaacgcaa aggagatata ggtgcgcgac ctgatcctgg   1560
tgggcggcgg cctggccaac ggcctgatcg cctggcgcct gcgccagcgc tacccgcagc   1620
tcaacctgct gctgatcgag gccggcgagc agccgggcgg caaccacacc tggtcgttcc   1680
acgaggacga cctgaccccg ggccagcacg cctggctggc ccgctggtg gcccacgcct   1740
ggccgggcta cgaggtgcag ttcccggacc tgcgccgccg cctggcccgc ggctactact   1800
cgatcacctc ggagcgcttc gccgaggccc tgcaccaggc cctgggcgag aacatctggc   1860
tgaactgctc ggtgtcggag gtgctgccga actcggtgcg cctggccaac ggcgaggccc   1920
tgctggccgg cgccgtgatc gacggccgcg gcgtgaccgc ctcgtcggcc atgcagaccg   1980
gctaccagct cttcctgggc cagcagtggc gcctgaccca gccgcacggc ctgaccgtgc   2040
cgatcctgat ggacgccacc gtggcccagc agcagggcta ccgcttcgtg tacaccctgc   2100
cgctgtcggc cgacaccctg ctgatcgagg acacccgcta cgccaacgtg ccgcagcgcg   2160
acgacaacgc cctgcgccag accgtgaccg actacgccca ctcgaagggc tggcagctcg   2220
cccagctcga acgcgaggag accggctgcc tgccgatcac cctggccggc gacatccagg   2280
ccctgtgggc cgacgccccg ggcgtgccgc gctcgggcat gcgcgccggc ctgttccacc   2340
cgaccaccgg ctactcgctg ccgctggccg tggccctggc cgacgccatc gccgactcgc   2400
cgcgcctggg ctcggtgccg ctgtaccagc tcacccgcca gttcgccgag cgccactggc   2460
gccgccaggg cttcttccgc ctgctgaacc gcatgctgtt cctggccggc cgcgaggaga   2520
accgctggcg cgtgatgcag cgcttctacg gcctgccgga gccgaccgtg gagcgcttct   2580
acgccggccg cctgtcgctg ttcgacaagg cccgcatcct gaccggcaag ccgccggtgc   2640
cgctgggcga ggcctgccgc gccgccctga accacttccc ggaccgccgc gacaagggct   2700
gacctgtgtg aaattgttat ccgcttaccc atacgacgtc ccagacaaag gagatataga   2760
tgaagaagac cgtggtgatc ggcgccggct tcggcggcct ggccctggcc atccgcctgc   2820
aggccgccgg catcccgacc gtgctgctgg agcagcgcga caagccgggc ggccgcgcct   2880
acgtgtggca cgaccagggc ttcaccttcg acgccggccc gaccgtgatc accgacccga   2940
ccgccctgga ggccctgttc accctggccg gccgccgcat ggaggactac gtgcgcctgc   3000
tgccggtgaa gccgttctac cgcctgtgct gggagtcggg caagaccctg gactacgcca   3060
acgactcggc cgagctggag gcccagatca cccagttcaa cccgcgcgac gtggagggct   3120
accgccgctt cctggcctac tcgcaggccg tgttccagga gggctacctg cgcctgggct   3180
cggtgccgtt cctgtcgttc cgcgacatgc tgcgcgccgg cccgcagctc ctgaagctgc   3240
aggcctggca gtcggtgtac cagtcggtgt cgcgcttcat cgaggacgag cacctgcgcc   3300
aggccttctc gttccactcg ctgctggtgg gcggcaaccc gttcaccacc tcgtcgatct   3360
```

-continued

```
acaccctgat ccacgccctg gagcgcgagt ggggcgtgtg gttcccggag ggcggcaccg   3420
gcgccctggt gaacggcatg gtgaagctgt tcaccgacct gggcggcgag atcgagctga   3480
acgcccgcgt ggaggagctg gtggtggccg acaaccgcgt gtcgcaggtg cgcctggccg   3540
acggccgcat cttcgacacc gacgccgtgg cctcgaacgc cgacgtggtg aacacctaca   3600
agaagctgct gggccaccac ccggtgggcc agaagcgcgc cgccgccctg gagcgcaagt   3660
cgatgtcgaa ctcgctgttc gtgctgtact tcggcctgaa ccagccgcac tcgcagctcg   3720
cccaccacac catctgcttc ggcccgcgct accgcgagct gatcgacgag atcttcaccg   3780
gctcggccct ggccgacgac ttctcgctgt acctgcactc gccgtgcgtg accgacccgt   3840
cgctggcccc gccgggctgc gcctcgttct acgtgctggc cccggtgccg cacctgggca   3900
acgccccgct ggactgggcc caggagggcc cgaagctgcg cgaccgcatc ttcgactacc   3960
tggaggagcg ctacatgccg ggcctgcgct cgcagctcgt gacccagcgc atcttcaccc   4020
cggccgactt ccacgacacc ctggacgccc acctgggctc ggccttctcg atcgagccgc   4080
tgctgaccca gtcggcctgg ttccgcccgc acaaccgcga ctcggacatc gccaacctgt   4140
acctggtggg cgccggcacc cacccgggcg ccggcatccc gggcgtggtg gcctcggcca   4200
aggccaccgc ctcgctgatg atcgaggacc tgcagtgatc tgggacgtcg tatgggtaag   4260
ctggacatca cctcccacaa cgcaaaggag atatagatgt cgcagccgcc gctgctggac   4320
cacgccaccc agaccatggc caacggctcg aagtcgttcg ccaccgccgc caagctgttc   4380
gacccggcca cccgccgctc ggtgctgatg ctgtacacct ggtgccgcca ctgcgacgac   4440
gtgatcgacg accagaccca cggcttcgcc tcggaggccg ccgccgagga ggaggccacc   4500
cagcgcctgg cccgcctgcg caccctgacc ctggccgcct tcgagggcgc cgagatgcag   4560
gacccggcct tcgccgcctt ccaggaggtg gccctgaccc acggcatcac cccgcgcatg   4620
gccctggacc acctggacgg cttcgccatg gacgtggccc agacccgcta cgtgaccttc   4680
gaggacaccc tgcgctactg ctaccacgtg gccggcgtgg tgggcctgat gatggcccgc   4740
gtgatgggcg tgcgcgacga gcgcgtgctg gaccgcgcct gcgacctggg cctggccttc   4800
cagctcacca acatcgcccg cgacatcatc gacgacgccg ccatcgaccg ctgctacctg   4860
ccggccgagt ggctgcagga cgccggcctg accccggaga actacgccgc ccgcgagaac   4920
cgcgccgccc tggcccgcgt ggccgagcgc ctgatcgacg ccgccgagcc gtactacatc   4980
tcgtcgcagg ccggcctgca cgacctgccg ccgcgctgcg cctgggccat cgccaccgcc   5040
cgctcggtgt accgcgagat cggcatcaag gtgaaggccg ccggcggctc ggcctgggac   5100
cgccgccagc acacctcgaa gggcgagaag atcgccatgc tgatggccgc cccgggccag   5160
gtgatccgcg ccaagaccac ccgcgtgacc ccgcgcccgg ccggcctgtg gcagcgcccg   5220
gtgtgactgt ccccccagtt ccagtacctg gtcatcatcc tgcctttcaa aggagatata   5280
gatgctgtgg atctggaacg ccctgatcgt gttcgtgacc gtgatcggca tggaggtggt   5340
ggccgccctg gcccacaagt acatcatgca cggctggggc tggggctggc acctgtcgca   5400
ccacgagccg cgcaagggcg ccttcgaggt gaacgacctg tacgccgtgg tgttcgccgc   5460
cctgtcgatc ctgctgatct acctgggctc gaccggcatg tggccgctgc agtggatcgg   5520
cgccggcatg accgcctacg gcctgctgta cttcatggtg cacgacggcc tggtgcacca   5580
gcgctggccg ttccgctaca tcccgcgcaa gggctacctg aagcgcctgt acatggccca   5640
ccgcatgcac cacgccgtgc gcggcaagga gggctgcgtg tcgttcggct tcctgtacgc   5700
cccgccgctg tcgaagctgc aggccaccct gcgcgagcgc cacggcgccc gcgccggcgc   5760
```

-continued

```
cgcccgcgac gcccagggcg gcgaggacga gccggcctcg ggcaagtgag ttatatggag   5820
ggggcaaacg ctctagaact agtggatcca aaggagatat agatgtcggc cgtgaccccg   5880
atgtcgagag tggtgccaaa ccaggcccta atcggcctga ctttagcggg gctgatagcc   5940
acggcgtggc tgagtctgca tatttacggg gtgtacttcc atcgttggac aatgtggtcg   6000
atcctgacgg tgccgctgat cgtggccttc cagacgtggc tgtcggtagg cctgttcatc   6060
gttgcccacg acgcaatgca cggctcccta gccccgggga ggccccgcct gaacaccgcc   6120
atcgggtccc tggccctagg cctgtacgct ggcttcaggt tcgcccctct gaagaccgcc   6180
caccatgccc accatgccgc accgggcaca gccgacgacc cggattttca cgcggacgcc   6240
ccccgtgcgt tcctgccgtg gttctacggc tttttccgta cctacttcgg ctggagggag   6300
ctggccgtgc tgaccgtgtt ggtggccgtg gctgttttaa tcctgggcgc ccgaatgccg   6360
aacttacttg tgttctgggc cgccccggct ctattatcgg ccttgcagct tttcaccttc   6420
ggcacatggc tgccgcaccg acacaccgac gacgccttcc cggaccacca caacgctcgc   6480
acttcaccct ttggccccat cctgtctctg ctgacctgct tccacttcgg ccggcaccat   6540
gagcaccacc tgactccgtg gaaaccgtgg tggaggctgt tctcgtagcg ataccgtcga   6600
cttcgagcaa ataaaacgaa aggctcagtc gaaagactgg gcctttcgtt ttatctgttg   6660
tttgtcggtg aacgctctca ttaatgaatc ggccaacgcg cggggagagg cggtttgcgt   6720
attgggcgca tgcataaact gctgccgttt agcccggata gcgtggtgac ccacggcgat   6780
tttagcctgg ataacctgat tttcgatgaa ggcaaactga ttggctgcat tgatgtgggc   6840
cgtgtgggca ttgcggatcg ttatcaggat ctggccattc tgtggaactg cctgggcgaa   6900
tttagcccga gcctgcaaaa acgtctgttt cagaaatatg gcattgataa tccggatatg   6960
aacaaactgc aatttcatct gatgctggat gaattttttct aagacccttg tctaatcaat   7020
gcggacccta gaggtcccct tttttatttt aaaaattttt tcacaaaacg gtttacaagc   7080
ataaaatctc tgaagatgtg tataagagac agactagtct tggactcctg ttgatagatc   7140
cagtaatgac ctcagaactc catctggatt tgttcagaac gctcggttgc cgccgggcgt   7200
tttttattgg tgagaatcca ggggtcccct ggtttaaact acacaagtag cgtcctgaac   7260
ggaacctttc ccgttttcca gaatctgatg ttccatgtga cctcctaaca tggtaacgtt   7320
catgattacc agtgcactgc atcgtgcggc ggattgggcg aaaagcgtgt tttctagtgc   7380
tgcgctgggt gatccgcgtc gtaccgcgcg tctggtgaat gttgcggcgc aactggccaa   7440
atatagcggc aaaagcatta ccattagcag cgaaggcagc aaagccatgc aggaaggcgc   7500
gtatcgtttt attcgtaatc cgaacgtgag cgcggaagcg attcgtaaag cgggtgccat   7560
gcagaccgtg aaactggccc aggaatttcc ggaactgctg gcaattgaag ataccacctc   7620
tctgagctat cgtcatcagg tggcggaaga actgggcaaa ctgggtagca ttcaggataa   7680
aagccgtggt tggtgggtgc atagcgtgct gctgctggaa gcgaccacct ttcgtaccgt   7740
gggcctgctg catcaagaat ggtggatgcg tccggatgat ccggcggatg cggatgaaaa   7800
agaaagcggc aaatggctgg ccgctgctgc aacttcgcgt ctgagaatgg gcagcatgat   7860
gagcaacgtg attgcggtgt gcgatcgtga agcggatatt catgcgtatc tgcaagataa   7920
actggcccat aacgaacgtt ttgtggtgcg tagcaaacat ccgcgtaaag atgtggaaag   7980
cggcctgtat ctgtatgatc acctgaaaaa ccagccggaa ctgggcggct atcagattag   8040
cattccgcag aaaggcgtgg tggataaacg tggcaaacgt aaaaaccgtc cggcgcgtaa   8100
```

-continued

```
agcgagcctg agcctgcgta gcggccgtat taccctgaaa cagggcaaca ttaccctgaa   8160

cgcggtgctg gccgaagaaa tcaatccgcc gaaaggcgaa accccgctga aatggctgct   8220

gctgaccagc gagccggtgg aaagtctggc ccaagcgctg cgtgtgattg atatttatac   8280

ccatcgttgg cgcattgaag aatttcacaa agcgtggaaa acgggtgcgg gtgcggaacg   8340

tcagcgtatg gaagaaccgg ataacctgga acgtatggtg agcattctga gctttgtggc   8400

ggtgcgtctg ctgcaactgc gtgaatcttt tactccgccg caagcactgc gtgcgcaggg   8460

cctgctgaaa gaagcggaac acgttgaaag ccagagcgcg gaaaccgtgc tgaccccgga   8520

tgaatgccaa ctgctgggct atctggataa aggcaaacgc aaacgcaaag aaaaagcggg   8580

cagcctgcaa tgggcgtata tggcgattgc gcgtctgggc ggctttatgg atagcaaacg   8640

taccggcatt gcgagctggg gtgcgctgtg ggaaggttgg gaagcgctgc aaagcaaact   8700

ggatggcttt ctggccgcga aagacctgat ggcgcagggc attaaaatct aatggaatcg   8760

aacccagctt tcttgtacaa agttggcatt ataagaaagc attgcttatc aatttgttgc   8820

aacgaacagg tcactatcag tcaaaataaa atcattattt g                        8861
```

METHODS FOR PRODUCING BIOCHEMICALS USING ENZYME GENES DERIVED FROM A STRAIN OF *BREVUNDIMONAS*, AND COMPOSITIONS MADE THEREBY

CROSS-REFERENCE TO RELATED APPLICATIONS

This application claims the benefit of Japanese patent application No. 2021-033930 filed on Mar. 3, 2021, and also claims priority to U.S. provisional application 63/130,569 filed on Dec. 24, 2020, both applications are incorporated herein by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 5627_12_ST25.txt. The text file is 46 KB, was created on Jul. 13, 2023, and is being submitted electronically via EFS-Web.

BACKGROUND

The present disclosure is generally related to the field of molecular biology and more particularly to genetically-engineering the metabolic pathways of microorganisms to utilize various feedstocks, including gaseous feedstocks, for the biological production of biochemicals.

SUMMARY

In certain embodiments, a nucleic acid sequence is provided for expressing carotenoid products comprising any one or more of SEQ ID NOS: 1, 4, 5, 6 or 7. In certain frequent embodiments, a vector is provided comprising the nucleic acid of SEQ ID NO: 1 and a heterologous nucleic acid sequence.

In certain frequent embodiments, a nucleic acid sequence is provided that encodes an enzyme comprising an amino acid sequence that is at least 96% identical or homologous to SEQ ID NO: 2, and the expressed enzyme is capable of converting β-carotene to canthaxanthin. In certain related embodiments, the amino acid sequence is at least 97% identical or homologous to SEQ ID NO: 2, and the expressed enzyme is capable of converting β-carotene to canthaxanthin. In certain related embodiments, the amino acid sequence is at least 98% identical or homologous to SEQ ID NO: 2, and the expressed enzyme is capable of converting β-carotene to canthaxanthin. In certain related embodiments, the amino acid sequence is at least 99% identical or homologous to SEQ ID NO: 2, and the expressed enzyme is capable of converting β-carotene to canthaxanthin.

In frequently included embodiments, a vector is provided comprising one or more nucleic acid sequence(s) that encode(s) an enzyme comprising an amino acid sequence that is at least 96% identical to SEQ ID NO: 2, wherein when expressed the enzyme is capable of converting β-carotene to canthaxanthin. In certain related embodiments, the amino acid sequence is at least 97% identical or homologous to SEQ ID NO: 2, and the expressed enzyme is capable of converting β-carotene to canthaxanthin. In certain related embodiments, the amino acid sequence is at least 98% identical or homologous to SEQ ID NO: 2, and the expressed enzyme is capable of converting β-carotene to canthaxanthin. In certain related embodiments, the amino acid sequence is at least 99% identical or homologous to SEQ ID NO: 2, and the expressed enzyme is capable of converting β-carotene to canthaxanthin.

In frequently included embodiments, a synthetic nucleic acid construct is provided comprising a promoter, a ribosome binding site, and one of more nucleic acid sequence that encode(s) an enzyme comprising an amino acid sequence that is at least 96% identical to SEQ ID NO: 2, wherein when expressed the enzyme is capable of converting β-carotene to canthaxanthin. In certain related embodiments, the amino acid sequence is at least 97% identical or homologous to SEQ ID NO: 2, and the expressed enzyme is capable of converting β-carotene to canthaxanthin. In certain related embodiments, the amino acid sequence is at least 98% identical or homologous to SEQ ID NO: 2, and the expressed enzyme is capable of converting β-carotene to canthaxanthin. In certain related embodiments, the amino acid sequence is at least 99% identical or homologous to SEQ ID NO: 2, and the expressed enzyme is capable of converting β-carotene to canthaxanthin. Often the synthetic nucleic acid construct is a vector comprising a plasmid.

In frequent embodiments a transformed expression host organism is provided comprising the synthetic nucleic acid construct noted above and herein, and the transformed host organism is capable of heterologous expression of the synthetic nucleic acid construct. Often the expression host organism is a transformed bacteria adapted to grow in a chemoautotrophic metabolic mode. In certain embodiments the expression host organism is *Cupriavidus necator.*

In certain embodiments a nucleic acid sequence is provided corresponding to a crtW carotenoid ketolase gene from *Brevundimonas* strain OB307 that encodes the amino acid sequence of SEQ ID NO: 2, wherein the nucleic acid sequence is comprised in an expression construct adapted to produce carotenoids in a biological host cell. In certain frequent embodiments, the biological host cell is capable of using $CO_2$ and $H_2$ to satisfy as least part of the carbon and energy requirements of the host cell.

In certain embodiments, a nucleic acid sequence is provided corresponding to a crtZ-crtW carotenoid hydroxylase-ketolase gene fusion, wherein the crtW portion of the fusion is a ketolase gene from *Brevundimonas* strain OB307 that encodes the amino acid SEQ ID NO: 2.

In certain embodiments, a nucleic acid sequence is provided encoding a crtZ-crtW carotenoid hydroxylase-ketolase fusion protein of SEQ ID NO: 3, wherein (a) the crtW portion of the fusion is a ketolase gene from *Brevundimonas* strain OB307 that encodes the amino acid sequence of SEQ ID NO: 2, and (b) the nucleic acid sequence is part of an expression construct adapted to produce carotenoids when functionally integrated in a biological host cell.

In certain embodiments, a nucleic acid sequence is provided encoding a crtZ-crtW carotenoid hydroxylase-ketolase fusion protein of SEQ ID NO: 3, wherein (a) the crtW portion of the fusion is a ketolase gene from *Brevundimonas* strain OB307 that encodes the amino acid sequence of SEQ ID NO: 2, and (b) the nucleic acid sequence is part of an expression construct adapted to produce carotenoids when functionally integrated in a biological host cell, and (c) the biological host cell is capable of using $CO_2$ and $H_2$ to satisfy as least part of its carbon and energy requirements.

In certain embodiments, a suicide vector construct is provided adapted for inserting a DNA sequence into a genome of a bacterium using a transposon, the suicide vector construct comprising (a) the DNA sequence; (b) an insert-flanking DNA comprising the nucleic acid sequence of SEQ ID NO: 3 that contains the transposon; and (c) a suicide plasmid backbone. In some embodiments the suicide vector construct is adapted for inserting a DNA sequence into a microbial genome of a bacterium using a transposon. The microbial genome can include organisms such as archaea, bacteria, and yeast.

In certain embodiments, a transformed host cell is provided comprising a nucleic acid sequence that encodes the amino acid SEQ ID NO: 2, wherein the nucleic acid sequence is part of an expression construct adapted to produce carotenoids in the host cell.

In certain embodiments, a method of forming a transformed host cell contemplated herein is provided, comprising inserting the expression construct into the genome of the host cell using a transposon. Often such insertion utilizing a is a transposon is a random insertion.

In certain embodiments, a nucleic acid sequence is provided corresponding to a crtW carotenoid ketolase gene from *Brevundimonas* strain OB307 that encodes the amino acid sequence of SEQ ID NO: 2, wherein the nucleic acid sequence is part of an expression construct adapted to produce carotenoids in a cell-free expression system.

In certain embodiments, a method of producing ketocarotenoids in a biological host cell is provided by heterologous expression of OB307-crtW in the host cell. Often the biological host cell comprises a hydrogen-oxidizing bacterium. Also often the hydrogen-oxidizing bacterium comprises a strain selected from *Cupriavidus, Rhodobacter, Rhodococcus, Rhodopseudomonas, Rhodospirillum, Paracoccus* or *Hydrogenophaga*. In certain embodiments, the strain of hydrogen-oxidizing bacterium is *Cupriavidus necator*. In certain often included embodiments the biological host cell is cultivated as part of a consortium of different species of host cells.

In certain embodiments, a method of producing ketocarotenoids in a biological host cell is provided including transforming the biological host cell with a vector comprising a crtZ-OB307-crtW fusion, and heterologously expressing the crtZ-OB307-crtW fusion in the biological host cell to synthesize the ketocarotenoids; or heterologously expressing a crtZ-OB307-crtW fusion in the biological host cell to synthesize the ketocarotenoids. Often the biological host cell comprises a hydrogen-oxidizing bacterium. Also often the hydrogen-oxidizing bacterium comprises a strain selected from *Cupriavidus, Rhodobacter, Rhodococcus, Rhodopseudomonas, Rhodospirillum, Paracoccus* or *Hydrogenophaga*. In certain embodiments, the strain of hydrogen-oxidizing bacterium is *Cupriavidus necator*. In certain often included embodiments the biological host cell is cultivated as part of a consortium of different species of host cells.

In certain embodiments, a method of producing canthaxanthin from β-carotene in vitro is provided, comprising contacting a protein expression product of a nucleic acid sequence at least 96% identical to the nucleic acid sequence of any of SEQ ID NOS: 1, 4, 5, 6 or 7 in a solution that comprises β-carotene, wherein the protein expression product catalyzes a conversion of at least some of the β-carotene to canthaxanthin. Often the nucleic acid sequence is at least 90% identical to the nucleic acid sequence of any of SEQ ID NOS: 1, 4, 5, 6 or 7. Often the nucleic acid sequence is at least 91% identical to the nucleic acid sequence of any of SEQ ID NOS: 1, 4, 5, 6 or 7. Often the nucleic acid sequence is at least 92% identical to the nucleic acid sequence of any of SEQ ID NOS: 1, 4, 5, 6 or 7. Often the nucleic acid sequence is at least 93% identical to the nucleic acid sequence of any of SEQ ID NOS: 1, 4, 5, 6 or 7. Often the nucleic acid sequence is at least 94% identical to the nucleic acid sequence of any of SEQ ID NOS: 1, 4, 5, 6 or 7. Often the nucleic acid sequence is at least 95% identical to the nucleic acid sequence of any of SEQ ID NOS: 1, 4, 5, 6 or 7. Often the nucleic acid sequence is at least 97% identical to the nucleic acid sequence of any of SEQ ID NOS: 1, 4, 5, 6 or 7. Often the nucleic acid sequence is at least 98% identical to the nucleic acid sequence of any of SEQ ID NOS: 1, 4, 5, 6 or 7. Often the nucleic acid sequence is at least 99% identical to the nucleic acid sequence of any of SEQ ID NOS: 1, 4, 5, 6 or 7. In certain frequent embodiments the host organism is one that naturally produces β-carotene.

BRIEF DESCRIPTION OF THE DRAWINGS

FIG. 2 depicts the components of the System 1 astaxanthin operon with crtZ and OB307 crtW.

FIG. 3 depicts the components of the System 2 canthaxanthin operon, which has no crtZ.

FIG. 4 depicts the components of the System 3 astaxanthin operon with the crtZW fusion gene.

FIG. 5 depicts a detailed map of the synthetic carotenoid operon for making astaxanthin (containing the OB307-crtW gene) along with a Tn5 transposase gene inserted into a suicide vector, with tetracycline as the antibiotic resistance marker. The transposon is added in order to randomly insert the operon into the genome of the host cell.

FIG. 6 depicts the process of transformation and chromosomal insertion of the operon into the host cell using transposon mutagenesis. System 1 is used here as an example. (ME=Mosaic Ends (inverted repeat sequences); Pro=Promoter; ori=Origin of replication or transfer; term=Transcriptional terminator).

FIG. 7 is the HPLC chromatogram showing the canthaxanthin produced by *C. necator* cells that heterologously express the canthaxanthin biosynthesis pathway. Solid line: Cell extract. Dashed line: canthaxanthin standard.

FIG. 8 is the corresponding UV-Vis spectrum of the canthaxanthin peak shown in FIG. 7.

FIG. 9 is the HPLC chromatogram showing the carotenoid products from *C. necator* cells that heterologously express the astaxanthin biosynthesis pathway. Solid line: Cell extract. Dashed line: Astaxanthin standard.

FIG. 10 is the corresponding UV-Vis spectrum of the astaxanthin peak shown in FIG. 9.

DETAILED DESCRIPTION

Figure 1:
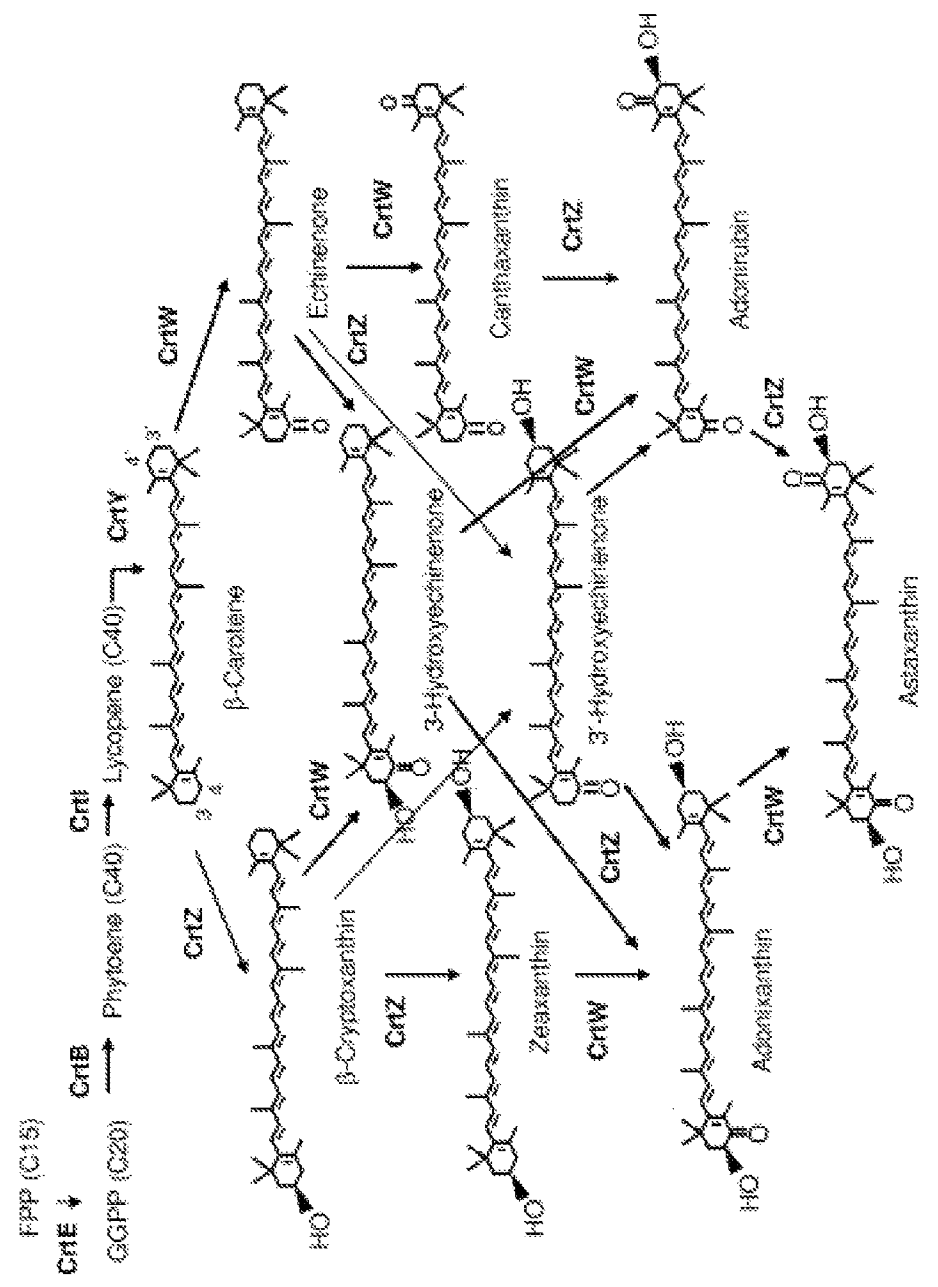
FIG. 1 depicts a schematic of the individual enzymes and products in the biosynthetic pathway between farnesyl diphosphate (FPP) and astaxanthin. A typical carotenoid metabolic pathway includes genes crtE, B, I Y, Z and W.

Carotenoids are long-chain isoprenoid molecules that have nutritional advantages as colorants and additives in fish feed, animal feed and nutraceuticals because they provide protection against cellular oxidative damage, in particular against free radicals and reactive oxygen species. Carotenoids can be expressed in plants, algae, archaea, fungi and bacteria, both naturally and through the expression of one or more carotenoid genes that encode the biosynthetic enzymes. Traditional production of forty-carbon (C40) tetraterpene carotenoids, including carotenes and xanthophylls, has involved extraction of native molecules from various microbes or plants. However, some naturally-occurring producers of astaxanthin, such as the yeast *Xanthophyllomyces* produce a less valuable enantiomer of astaxanthin and the process of growing highly productive, naturally producing microalgae, such as *Haematococcus pluvialis*, is difficult, time-consuming, resource-intensive and expensive.

Non-biological production of molecules such as astaxanthin and canthaxanthin, via chemical synthesis from petroleum feedstocks, has been achieved (Ernst, 2002). However, these latter methods produce a mixture of astaxanthin enantiomers that are also less valuable because they are less efficient radical quenchers and therapeutics and these synthetic products have faced significant regulatory issues with regard to human and animal consumption in the EU. More recently, genetically-engineered organisms have been used for the production of high-value canthaxanthin, astaxanthin and other C40 carotenoids and xanthophylls. FIG. 1 shows the carotenoid biosynthesis pathway from farnesyl diphosphate (FPP) to astaxanthin.

In addition to astaxanthin, canthaxanthin is a valuable carotenoid product that can be synthesized by ketolase enzymes, such as the bacterial crtW ketolase gene acting on beta-carotene as its substrate. Carotenoids such as canthaxanthin and astaxanthin can be produced by ketolases encoded by crtW genes from various *Brevundimonas* species, which are considered to be the most active and effective carotenoid ketolases.

There is also a need for an expression system that can cheaply and efficiently produce carotenoids using this CrtW enzyme, since the yield of carotenoid per gram dry weight of biomass and rate of production is not high in natural or genetically modified organisms.

Hydrogen-oxidizing bacteria are attractive hosts for carotenoid expression because some species naturally produce larger amounts of internal membranes than many other bacteria, and these membranes are required for accumulating the highly lipophilic C40 carotenoids.

Extensive membrane capacity is also advantageous because both the CrtZ hydroxylase and the CrtW ketolase enzymes are likely integral membrane proteins that contain transmembrane (TM) helices capable of spanning cell membranes.

Furthermore, because certain hydrogen-oxidizing bacteria such as *Cupriavidus necator* do not naturally make carotenoids, there is less of a chance of regulatory interference (e.g., feedback inhibition) or undesirable enzymatic modification of the product (as in, for example, *Brevundimonas vesicularis* strain DC263, which naturally hydroxylates the astaxanthin product to dihydroxy-astaxanthin because it contains the crtG gene).

The carotenoids so produced are provided as part of the bacterial biomass or extracted from it to create a substantially pure carotenoid product, or through other extraction methods such as super critical $CO_2$ or solvent based extraction to form a concentrate. Further, carotenoids such as canthaxanthin can be mixed with other ingredients, such as sugars, corn starch, lignosulphonate, binders, oils or others to produce a product (e.g., DSM Carophyll Red 10%).

The bacterial CrtW enzymes employ 6-8 of the following amino acid residues to bind the di-iron cofactors that catalyze the oxygenation reactions: His69, His73, His107, His110, His111, His225, His228 and His229, as determined by the presence of the His-rich motifs HX(3 or 4)H, HX(2 or 3)HH, and HX(2 or 3)HH. Asp118 may also be required, based on mutagenesis studies. Thus, although not intending to be bound by any particular theory of operation, it is believed that natural or engineered versions of this enzyme should or must include these ligands in order to have catalytic activity. Likewise, such enzymes may require functional transmembrane sequences since there are putative TM helices that appear to organize the iron binding sites on the inside of the membrane.

Expressing such codon-optimized gene pathways in bacteria that have high G+C content has previously proved to be challenging, for example, because the GC content makes it difficult to de novo synthesize genes and operons for synthetic biology.

The present disclosure describes a newly discovered crtW gene from a new strain of *Brevundimonas*, designated herein as OB307, which encodes a novel ketolase for carotenoid synthesis. The present disclosure also provides an exemplary synthetic operon containing additional relevant carotenoid gene sequences, the expression of which is used to produce ketocarotenoids. Suitable DNA expression constructs derived from these sequences are inserted into an expression host for expression. The expression product being a ketolase enzyme that is operable for transforming beta-carotene into canthaxanthin and astaxanthin. The carotenoid products of this synthetic operon have been expressed in *Escherichia coli, Bacillus subtilis* B-14200, *Bacillus* B-356, *Rhodopseudomonas palustris, Rhodobacter sphaeroides* and *Cuprividus necator. R. palustris* and *R. sphaeroides* are commonly known as purple non-sulfur (PNS) bacteria. *Rhodobacter capsulatus* is another PNS bacterium that can be used as a host for these DNA expression constructs.

As disclosed herein, the presently disclosed CrtW ketolase enzyme is often utilized for production of ketocarotenoids such as astaxanthin and canthaxanthin via cloning of the disclosed DNA sequences (including similar sequences having attributes noted herein), arranging the DNA into a construct that includes a ribosome binding site, a promoter, and a terminator, as well as other structural gene elements. Other enzyme genes according to the present embodiments, such as crtZ, crtY, crtI, crtB, crtE, as well as additional structural and control elements are also optionally incorporated into the construct to form an operon for carotenoid production. This construct is then introduced into a host organism such as a host cell, using methods known to the art, either as one or more small, circularized DNA vectors, such as a plasmid, or via incorporation into the genome of the organism. For organisms that already produce beta-carotene, the gene encoding this single enzyme is introduced to cause the production of this CrtW ketolase enzyme and the transformation of some of the beta-carotene into canthaxanthin. If a crtZ gene is also introduced, the gene product (i.e., a hydroxylase) may also be expressed, and it will transform at least some of the canthaxanthin to astaxanthin.

The product of this crtW gene is used, for example, in a cell free expression system in which beta-carotene is enzymatically converted into canthaxanthin. If the crtZ and crtW genes are expressed in combination, either simultaneously or sequentially, at least a portion of the beta-carotene substrate will be transformed into canthaxanthin and a portion is transformed into astaxanthin by the action of the enzyme products of the two genes. The novel crtW and crtZ genes may be provided on two different segments of DNA, or as a single piece of DNA comprising a gene for a fusion protein, which encodes both the CrtW ketolase and CrtZ hydroxylase functions.

Many different organisms are potential heterologous expression hosts for this novel crtW gene. Hosts that care able to utilize $H_2$ and $CO_2$ as energy and carbon sources and those that are unable to utilize $H_2$ and $CO_2$ as energy and carbon sources are contemplated as suitable heterologous expression hosts. For example, these include bacteria, plants, algae, archaea, and fungi. Bacteria such as *Escherichia coli* and *Bacillus subtilis*, fungi such *Saccharomyces cerevisiae* and *Aspergillus oryzae*, plants such as *Oryza glaberrima*, algae such as *Chlorella vulgaris*, or archaea such as *Sulfolobus solfataricus*, or others species of organism can serve as heterologous expression hosts for this novel crtW gene, for the production the enzyme which it encodes and for the production of the carotenoid products through the action of this enzyme.

The heterologous expression of this enzyme and the synthetic operon disclosed herein have been shown in *Escherichia coli, Bacillus subtilis* B-14200, *Bacillus* B-356, *Rhodopseudomonas palustris, Rhodobacter sphaeroides* and *Cuprividus necator* initially using a broad host range expression plasmid. In all cases, the heterologous expression of the novel OB307-crtW gene was observed via production of canthaxanthin in the transformed bacteria (versus no production of canthaxanthin in the wild type organism). This transformation was achieved using the same plasmid as was used in *C. necator*. The promoter disclosed herein is active in all of these strains. The *E. coli* cells were transformed using electroporation of the plasmid, as described above. The other strains were transformed using conjugation with *E. coli* strain S17-1 according to standard methods (see, e.g, Phornphisutthimas et al., 2007; Gruber et al., 2015). The conjugated cells were first plated on LB agar, then resuspended in sterile liquid medium with serial dilutions and plated on the following agar plates: (1) for *E. coli*, LB plus 50 μg/ml kanamycin or 10 μg/ml tetracycline; (2) for *Bacillus*, MR2 medium plus 2% fructose and 50 μg/ml kanamycin; and (3) for *C. necator* and the PNS bacteria, MR2 medium plus 2% fructose and 500 μg/ml kanamycin. Surviving transconjugant colonies were then picked and restreaked on fresh plates until pure single colonies were obtained. Growth in liquid cultures was performed by inoculating cells of a given variant into LB plus antibiotic (for all of the strains) or MR2 plus antibiotic (for the H2-oxidizing PNS bacteria and *C. necator*).

A fusion gene which comprised of crtZ and crtW was created by constructing a piece of synthetic DNA in which crtZ and crtW were joined by a linker sequence, and incorporating this fusion sequence into the synthetic operon in place of the original crtW gene in the expression plasmid. This heterologous expression vector was then transformed into *Escherichia coli* and *Cupriavidus necator*. Production of astaxanthin and canthaxanthin was observed in both cases. An allelic exchange system (using NaCl-free agar medium with 6% sucrose (w/v) for the sacB levansucrase counterselection) and suicide vector were also used to insert this synthetic operon into the *C. necator* genome and the production of carotenoids was again observed.

*C. necator* strain H16 has been used as an expression host, as have other *C. necator* strains, and strains of other hydrogen-oxidizing bacteria. The carotenoid products can thus be produced by gas fermentation of the transformed bacterium, using inexpensive feedstocks (e.g., waste $CO_2$, $H_2$, $O_2$ and mineral salts) to improve the economic efficiency of the process.

Additional genera and species of hydrogen-oxidizing bacteria that can be transformed with the vectors and DNA constructs described herein for heterologous expression in the carotenoid pathway while growing on $H_2$—$CO_2$—$O_2$ include, for example, *Rhodobacter capsulatus* and other *Rhodobacter* species, *Paracoccus, Rhodococcus, Hydrogenophaga, Rhodospirillum, Rhodopseudomonas*, and the like.

The novel strain of *Brevundimonas OB*307 was isolated as a red-orange contaminant colony from an agar plate in the laboratory. Its 16S rRNA genes were sequenced (forward and reverse), and compared using Clustal W to the 16S sequences of other *Brevundimonas* species. This analysis revealed that OB307 has a 99.7-99.8% identity with the 16S sequences from *B. vesicularis* and *B. nasdae*. Genomic DNA was extracted from approximately 100 mg of wet cell paste, the entire genome was sequenced using 60× Illumina paired end sequencing (150 base pair reads), and the sequence contigs were assembled and annotated by SNPsaurus, Inc. (Eugene, Oreg.). From this sequence, a BLAST search identified multiple genes with high similarity to other published carotenoid biosynthetic genes.

One of the complete open reading frame sequences was initially identified by the annotating software as a "fatty acid desaturase." Fatty acid desaturases are known to have a similar structure to carotenoid ketolases, and further analysis revealed that this sequence has high similarity to CrtW-type carotenoid ketolases, and our subsequent expression cloning confirmed its activity. The gene sequence is therefore designated herein as OB307-crtW (SEQ ID NO: 1). As can be seen from the translated amino acid sequence of OB307-CrtW, it contains the eight-histidine motif (highlighted in yellow) and the Asp-118 (highlighted in blue) that define the di-iron binding site for this type of ketolase (SEQ ID NO: 2). TABLE 1 shows a Clustal W 2.1 amino acid sequence alignment between OB307-CrtW and the CrtW from *Brevundimonas* strain DC263 (GenBank accession number ABC50116.1). Both proteins contain 241 amino acids, and there are 11 amino acid differences between them (about 95.5% identity). More recently, a putative crtW gene from *Brevundimonas* strain SgAir0440 was published as part of the genome sequence of an air-contaminating bacterium (GenBank accession number QCR00114). The gene has 99.6% similarity to the amino acid sequence of OB307-crtW, however, it was not reported to have been cloned and expressed, nor was the function of the enzyme analyzed to confirm that it was indeed a beta-carotene ketolase.

TABLE 1

Clustal W 2.1 amino acid sequence alignment between OB 3G7-CrtW and the CrtW from *Brevundimonas* strain DC263

| | |
|---|---|
| OB307-crtW | MSAVTPMSRVVPNQALIGLTLAGLIATAWLSLHIYGVYFHRWTMWSILTVPLIVAFQTWL |
| DC263-crtW | MSAVTPMSRVVPNQALIGLTLAGLIAAAWLTLHIYGVYFHRWTIWSILTVPLIVAGQTWL |
| | |
| OB307-crtW | SVGLFIVAHDAMHGSLAPGRPRLNTAIGSLALGLYAGFRFAPLKTAHHAHHAAPGTADDP |
| DC263-crtW | SVGLFIVAHDAMHGSLAPARPRLNTAIGSLALALYAGFRFTPLKTAHHAHHAAPGTADDP |
| | |
| OB307-crtW | DFHADAPRAFLPQFYGFFRTYPGWRELAVLTVLVAVAVLILGARMPNLLVWFAAPALLSA |
| DC263-crtW | DFHADAPRAFLPQFYGFFRTYPGWRELAVLTVLVAVAVLILGARMPNLLVWFAAPALLSA |

TABLE 1-continued

Clustal W 2.1 amino acid sequence alignment between OB 3G7-CrtW and the CrtW from *Brevundimonas* strain DC263

```
OB307-crtW  LQLFTFGTWLPHRHTDDAFPDHHNARTSPFGPILSLLTCFHFGRHHEHHLTPWKPWWRLF
DC263-crtW  LQLFTFGTWLPHRHTDDAFPDHHNARTSPFGPVLSLLTCFHFGRHHEHHLTPWKPWWRLF

OB307-crtW  S
DC263-crtW  S
```

The native OB307-crtW sequence was converted into a new sequence that is codon optimized for expression in *C. necator*. This new sequence was included as part of a codon-optimized synthetic operon comprising crtE, crtY, crtI, crtB, and crtW, which makes canthaxanthin (FIG. 3). Constructs designed to make astaxanthin also included the complete crtZ sequence (FIG. 2). The other gene sequences in the pathway were sourced from various other bacteria, with the GenBank accession numbers as follows: the genes crtE, crtY, crtI, and crtB were synthesized from the sequence of the *Pantoea agglomerans/Erwinia herbicola* pAC-BETA plasmid, M8720/M99707; crtZ was synthesized from the sequence of *Pantoea ananatis* Strain AJ13355, NC_017533; and crtW was synthesized from the sequence of OB307-crtW described herein.

Synthesis of the operon benefits from a specialized procedure (e.g., as available from Aster Bioscience, Inc.; Livermore, Calif.) due to the very high G+C content (ca. 61%-70%). A constitutive promoter that is highly active in *C. necator* was placed upstream of the carotenoid genes to direct mRNA synthesis in the cell. Other suitable promoters are well known in the art and contemplated herein. Inducible promoters, which can be used to control the timing of the onset of gene transcription by applying an external inducer molecule (e.g., IPTG for the lac or tac promoters) or an environmental stimulus (e.g., nitrogen deprivation for the phaC1 promoter) can also be used, if they are compatible with the metabolism and transport system of the host. Ribosome binding sites (RBSs) optimized for *C. necator* were placed upstream of each gene sequence. Spacer sequences were added between the promoter and the RBS of the crtE gene, as well as between the RBS and the start codon of each individual gene, in order to optimize the overall expression. A termination sequence (*E. coli* rrnB) was placed at the end of the operon to prevent unwanted translation of any downstream elements.

The synthetic operons (SEQ ID NO: 5, 6 and 7) were first tested for activity by cloning them into the broad host range plasmid pBBR1MCS-2 (e.g., kanamycin as a selection), using NdeI and AseI as the flanking restriction sites. The ligated DNA products were transformed into *E. coli* by electroporation using a Bio-Rad GenePulser II with a Capacitance Extender Plus Pulse Controller II unit (Bio-Rad Inc., Hercules, Calif.). *E. coli* cells were made electrocompetent using three washes with cold 10% glycerol according to the methods described in the online protocol of Belcher and Knight (https://openwetware.org/wiki/Belcher/Knight_Electrocompetent_Cells). 50 μl of electrocompetent cells were added to a chilled 1 mm gap sterile cuvette and mixed with 1 μl of DNA (approximately 1-50 ng). The electroporator settings were as follows: 1.2 kV, 25 μF, 200Ω. The time constant was typically 3-5 msec. After pulsing, the cells were then transferred to pre-warmed SOB medium in a small sterile tube and allowed to recover at 37° C. for 1 hour with shaking. Aliquots were then plated on LB agar with 50 μg/ml kanamycin for antibiotic selection. After incubation at 30° C., colonies were picked and individually grown up in LB broth. Plasmid DNA was isolated from the various clones by standard methods. The DNA was cut with the appropriate restriction enzymes and analyzed by agarose gel electrophoresis to identify the positive clones. Plasmid DNA from one correct clone was transformed into *E. coli* conjugation strain S17-1. The process described above was then repeated to find correct S17-1 clones. An S17-1 clone containing the synthetic canthaxanthin or astaxanthin operon in the plasmid pBBR1MCS-2 was then conjugated into the *C. necator* host strain or other host strains by standard methods as described above. After plating on solid MR2-fructose medium (Table 2) containing 500 μg/ml kanamycin, *C. necator* colonies appeared. Colonies that displayed a deep orange or red color were picked and re-streaked on kanamycin plates to confirm their colored phenotype and antibiotic resistance. Selected clones were picked and grown up in liquid medium with antibiotic.

TABLE 2

Composition of MR2 medium

| Name of Chemical | Formula | Mass (g) | Moles (mol) | Molar Mass (g/mol) |
|---|---|---|---|---|
| Sodium Phosphate Dibasic | Na2HPO4 | 4.00E+00 | 2.82E−02 | 141.96 |
| Potassium Phosphate Monobasic | KH2PO4 | 6.67E+00 | 4.90E−02 | 136.09 |
| Ammonium Chloride | NH4Cl | 1.80E+00 | 3.37E−02 | 53.49 |
| Sodium Bicarbonate | NaHCO3 | 2.00E−01 | 2.38E−03 | 84.01 |
| Ammonium Nickel (II) Sulfate Hexahydrate | (NH4)2Ni(SO4)2*6H2O | 1.07E−02 | 3.05E−05 | 349.99 |
| Add after autoclaving: | | | | |
| Iron (II) Sulfate Heptahydrate | FeSO4*7H2O | 1.20E−02 | 4.32E−05 | 278.01 |
| Calcium Chloride Dihydrate | CaCl2*2H2O | 2.00E−02 | 1.36E−04 | 147.01 |

TABLE 2-continued

| Composition of MR2 medium | | | | |
|---|---|---|---|---|
| Name of Chemical | Formula | Mass (g) | Moles (mol) | Molar Mass (g/mol) |
| Magnesium Sulfate Heptahydrate | MgSO4*7H2O | 1.13E+00 | 4.59E−03 | 246.47 |
| Trace Elements | | | | |
| Disodium EDTA | C10H14N2Na2O*2H2O | 1.00E−03 | 2.69E−06 | 372.24 |
| Iron (II) Sulfate Heptahydrate | FeSO4*7H2O | 4.00E−04 | 1.44E−06 | 278.01 |
| Zinc Sulfate Heptahydrate | ZnSO4*7H2O | 2.00E−05 | 6.96E−08 | 287.56 |
| Manganese (II) Chloride Tetrahydrate | MnCl2*4H2O | 6.00E−06 | 3.03E−08 | 197.91 |
| Boric Acid | H3BO3 | 6.00E−05 | 9.70E−07 | 61.83 |
| Cobalt (II) Chloride Hexahydrate | CoCl2*6H2O | 4.00E−05 | 1.68E−07 | 237.93 |
| Copper (II) Chloride Dihydrate | CuCl2*2H2O | 2.00E−06 | 1.17E−08 | 170.48 |
| Nickel (II) Chloride Hexahydrate | NiCl2*6H2O | 4.00E−06 | 1.68E−08 | 237.69 |
| Sodium Molybdate Dihydrate | Na2MoO4*2H2O | 6.00E−06 | 2.48E−08 | 241.95 |

As described above, the processivity of the enzymes at the end of the pathway for the production of astaxanthin can be improved by genetically fusing the genes for crtZ and crtW to encode for a chimeric protein. The fusion protein sequence was created by inserting the DNA sequence for a short linker peptide (encoding amino acid sequence GGGGSGGPGS) between the 3' end of the complete crtZ gene from *Pantoea ananatis* and the 5' end of OB307-crtW gene (without the N-terminal methionine), as shown in the map of FIG. 4, as well as SEQ ID NO: 3, SEQ ID NO: 4 and SEQ ID NO: 7. The crtZ-crtW fusion sequence was codon optimized, synthesized, and used to replace the crtW gene in the original operon construct to create the insert known as System 3 (SEQ ID NO: 7). When the expression plasmid encoding this sequence was transformed into a suitable host as described above, the cells expressed astaxanthin (FIG. 9 and FIG. 10).

In certain embodiments the pathways contemplated herein are improved by genetic modification, in particular by methods of directed evolution, for example via random mutagenesis and library screening to identify improved variants. Strain engineering of the host genome can also be used to improve expression of the recombinant pathway genes.

In certain embodiments the operon is inserted into the genome semi-randomly and then screened for production levels. In the case of carotenoid production, this screening can be done by looking for intense color production in colonies from plated libraries of transformants. Accordingly, a custom suicide vector was constructed (based on the non-replicating, allelic exchange plasmid of Hmelo et al. (2015)) so that the operon could be inserted between the mosaic ends (inverted 19-bp inside and outside end sequences) of the phage Tn5 transposon by restriction cloning with NdeI and NsiI. A Tn5 transposase sequence was also inserted into the plasmid (using Gateway cloning), along with a tetracycline resistance cassette to act as an antibiotic marker (see, e.g., FIG. 5, FIG. 6 and SEQ ID NO: 8). The transposon suicide vector was assembled, transformed into *E. coli* strain S17-1, and then conjugated into *C. necator* strain H16 as described above. Transconjugants were plated on MR2 agar plus 2% fructose and 10 µg/ml tetracycline as described above, followed by a second plating on LB agar plus 50 µg/ml kanamycin or MR2 agar plus 2% fructose and 50 µg/ml kanamycin to remove the *E. coli* donor. Orange and red colored colonies were picked for further characterization of their carotenoids as described above. A variety of pale and intensely colored colonies are observed, indicating that the operon has been inserted into a different genome location in each of the clones that expresses carotenoid.

To rapidly confirm initial expression of the pathway and production of the carotenoid products, *C. necator* clones with the pBBRMCS-2 expression plasmid were inoculated into 50 ml of sterile liquid minimal medium (MR2 at pH 6.8) at 30° C. in shake flasks with 20 g/L fructose added as a carbon source. After approximately 48 hours of growth, the cultures achieved an A620 (optical density measured at 620 nm) of approximately 1.4, and they exhibited a deep orange or red color due to production of carotenoids. Other expression hosts transformed with the expression plasmid, such as *Bacillus subtilis* strain NRRL B-14200, *Bacillus subtilis* strain NRRL B-354, *Rhodopseudomonas palustris* strain NRRL B4276, and *Rhodobacter sphaeroides* strain NRRL B1727, have also been cultivated in this way. NRRL strains were obtained from the USDA-ARS Culture Collection (Peoria, Ill.).

To evaluate production of carotenoid on gas, cells containing the genomically integrated operon were inoculated into 200-500 ml of sterilized MR2 minimal medium at pH 6.8 (with no carbon source) in a capped, stirred flask (magnetic stir bars) equipped with submerged gas inlets and an exit port. The sterilized external gas inlets, outlets and rubber tubing were capped with sterile disk filters (0.2 µm pore size; cellulose acetate syringe filter, VWR) to prevent contamination from the outside atmosphere. A mixture of $H_2$:$CO_2$:$O_2$ with an approximate ratio of 80:10:10 was supplied by commercial gas cylinders (Praxair, Inc.), or by electrolytic hydrogen from a generator (Parker Dominick Hunter Model 40H; Charlotte, N.C.). In some embodiments, the $CO_2$ (often containing other gases, such as $H_2$, CO, $SO_x$, $NO_x$) was collected as waste $CO_2$ from cement manufacturing, fossil fuel combustion, petrochemical hydrocracking operations and the like, and was supplied in pressurized cylinders. The gas mixing and gas flow rates were controlled by small network of gas flow meters and mass flow controllers (Alicat Scientific, Inc., Tucson, Ariz.). The stir plates and flasks were housed in incubators maintained at 30° C. The exit gas was collected and vented to the outside air. Cultures were grown for 72 hours until the cells reached an A620 of approximately 0.4 and turned noticeably red or orange in color. At commercial scale, this type of cultivation is performed in loop bioreactors specially designed for high-volume cultures grown entirely on gas. An example of a loop bioreactor for gas fermentation of methanotrophs (using methane and oxygen as feedstocks) is provided in Petersen et al. (2017, 2020). In another embodiment, the fermentation and cultivation of the host cells expressing the carotenoid genes employs a consortium (i.e., a mixture of different species) so as to improve the growth rate of the carotenoid-containing biomass or improve the overall characteristics of the biomass.

Production using cell free systems. It is contemplated that the enzymes and constructs provided in the present disclosure are used to express the pathway enzymes and generate the carotenoid products using cell-free expression systems (Schneider et al., 2010; Gregorio et al., 2019; Khambati et al., 2019). Such a system can, for example, be fed with the simple precursors of the carotenoid pathway, such as IPP and DMAP and FPP, and convert these compounds into the more valuable ketocarotenoid products. Cell free expression refers to an agent that, when combined with a polynucleotide, permits in vitro translation of the polypeptide or protein encoded by the polynucleotide. These systems are known in the art and exist for both eukaryotic and prokaryotic applications. Exemplary cell free expression systems that can be used in connection with the present disclosure include, for example, commercial kits for various species such as extracts available from Invitrogen Ambion, Qiagen and Roche Molecular Diagnostics, cellular extracts made from hydrogen oxidizing bacteria, including a strain selected from *Cupriavidus, Rhodobacter, Rhodococcus, Rhodopseudomas, Rhodospirillium, Paracoccus* or *Hydrogenophaga*, in addition to *E. coli* and other strains.

Cells were harvested by centrifugation at 6,000×g for 10 minutes. After resuspending in phosphate buffered saline, the cells were centrifuged again. An aliquot of the washed cell pellet was extracted with n-hexane/methanol (1:1 v/v) in a 1.5 ml microcentrifuge tube. The solvent extract was separated from the cell debris by centrifugation at 14,000×g for 5 minutes. Carotenoids can also be efficiently isolated and purified from biomass using supercritical CO2 extraction (Valderrama et al., 2003; Di Sanzo et al., 2018).

Carotenoid analysis. For identifying and assaying the production of carotenoids, 50 μl of solvent-extracted sample was loaded via syringe onto a Symmetry C18 5 μm (4.6×250 mm) HPLC (high-performance liquid chromatography) column, which was pre-equilibrated with a solution containing methanol/water 90:10 (v/v). The running solution was composed of a gradient of water, ethyl acetate, and water. The HPLC instrument was a Beckman System Gold equipped with a 168NM diode array detector. The running conditions were as follows: Flow rate: 1 mL/min; Temperature: 30° C. Peaks were identified by comparing their retention times with solutions of known carotenoid standards dissolved in n-hexane. Canthaxanthin standard was obtained from Honeywell Research, Inc.; astaxanthin was from Abcam (Cambridge, Mass.). Eluted components can also be identified, where possible, by their characteristic absorbance spectra. Sample chromatograms of canthaxanthin (FIG. 7) and astaxanthin (FIG. 9), as well as their corresponding UV-Vis absorption spectra (FIGS. 8 and 10), produced using the expression system of the present disclosure are shown. These experiments confirm that the OB307-crtW gene does encode a beta-carotene ketolase, and that the constructs expressing the new OB307-crtW gene do indeed produce canthaxanthin and astaxanthin.

This crtW sequence sometimes requires codon optimization when the gene is heterologously expressed in various expression hosts, in order to produce sufficient amounts of active enzyme to catalyze the transformation of beta-carotene to canthaxanthin. This is also true for the synthetic operon and for constructs where the gene sequences are arranged to produce fusion proteins, such as crtZ-crtW fusion proteins. In some embodiments of the present disclosure, the expression host is a plant. In some embodiments the expression host is a fungus, such as *Saccharomyces cerevisiae*. In some embodiments, the expression host is an alga, such as *Chlorella vulgaris*. In some embodiments, the expression host is a bacterium, such as a methylotroph (e.g., *Methylobacterium extorquens*), a methanotroph, (e.g., *Methylococcus capsulatus*), an acetogen (e.g., *Clostridium autoethanogenum*), a hydrogen-oxidizing bacterium (e.g., *Cupriavidus necator*), or a purple non-sulfur bacterium, such as *Rhodospirillum rubrum, Rhodobacter sphearoides, Rhodobacter capsulatus*, or *Rhodopseudomonas palustris*. Other potentially suitable bacterial hosts include *Rhodococcus opacus*, a *Paracoccus* species, such as *Paracoccus zeaxanthinifaciens*, or *Escherichia coli.*

In the foregoing specification, the invention is described with reference to specific embodiments thereof, but those skilled in the art will recognize that the invention is not limited thereto. Various features and aspects of the above-described invention may be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

REFERENCES

Di Sanzo, G et al. (2018) Supercritical Carbon Dioxide Extraction of Astaxanthin, Lutein, and Fatty Acids from *Haematococcus pluvialis* Microalgae. *Mar Drugs* 16:334.

Ernst, H (2002) Recent Advances in Industrial Carotenoid Synthesis. *Cheminform* 74:2213-2226.

Gregorio, N E et al. (2019) A User's Guide to Cell-Free Protein Synthesis. *Methods Protoc.* 2:24.

Gruber, S et al. (2015) Versatile plasmid-based expression systems for Gram-negative bacteria—General essentials exemplified with the bacterium *Ralstonia eutropha* H16. *New Biotechnol* 32:552-8.

Hmelo, L R, Borlee, B R, Almblad, H, et al. (2015) Precision-engineering the *Pseudomonas aeruginosa* genome with two-step allelic exchange. *Nat Protoc* 10:1820-1841.

Khambhati, K et al. (2019) Exploring the Potential of Cell-Free Protein Synthesis for Extending the Abilities of Biological Systems. *Front Bioen Biotechnol* 7:248.

Petersen, L A H et al. (2017) Mixing and mass transfer in a pilot scale U-loop bioreactor. *Biotechnol Bioeng.* 114:344-354.

Petersen, L A H et al. (2020) Modeling and system identification of an unconventional bioreactor used for single cell protein production. *Chem Eng J* 390:124438.

Phornphisutthimas, S et al. (2007) Conjugation in *Escherichia coli*—A laboratory exercise. *Biochem Mol Biol Educ* 35:440-5.

Schneider, B et al. (2010) Membrane Protein Expression in Cell-Free Systems. In: *Heterologous Expression of Membrane Proteins, Methods in Molecular Biology*, vol. 601 (I. Mus-Veteau, ed.), Humana Press, Springer Nature, Switzerland.

Valderrama, J O et al. (2003) Extraction of Astaxantine and Phycocyanine from Microalgae with Supercritical Carbon Dioxide *J Chem Eng Data* 48:827-830.

SEQUENCE LISTING
SEQ ID NO: 1 [OB307-crtW beta-carotene ketolase]

213: Unknown

220:

221: Gene (crtW)

222: Derived from *Brevundimonas* strain OB307

223: Bacterium of the genus *Brevundimonas*
ATGTCCGCCGTCACGCCAATGTCACGGGTCGTCCCGAACCAGGCCCTGATCGGTCTGACG

CTGGCTGGCCTGATCGCGACGGCCTGGCTGAGCCTGCATATCTACGGCGTCTATTTTCAT

CGCTGGACGATGTGGAGCATCCTGACCGTTCCGCTAATCGTCGCTTTCCAGACCTGGCTG

TCCGTCGGCCTGTTCATCGTCGCCCACGACGCCATGCACGGCTCTCTGGCTCCGGGACGC

CCTCGGCTGAACACGGCGATCGGCAGCCTGGCGCTGGGCCTCTACGCCGGTTTTCGTTTT

GCGCCGTTGAAGACGGCGCACCACGCTCATCATGCCGCGCCCGGCACGGCGGACGACCCC

GACTTTCACGCCGACGCCCCGCGCGCCTTCCTGCCCTGGTTCTACGGCTTTTTCCGTACC

TATTTCGGTTGGCGCGAGTTGGCCGTTCTGACGGTGCTCGTGGCCGTCGCAGTGCTGATC

CTTGGCGCCCGCATGCCCAATCTTCTGGTCTTCTGGGCCGCGCCCGCCCTGCTCTCGGCG

CTACAGCTTTTCACATTCGGCACCTGGCTGCCTCACAGGCATACCGACGACGCCTTCCCC

GACCACCACAACGCCCGCACCAGCCCCTTCGGCCCGATCCTGTCGTTGCTGACCTGCTTC

CACTTCGGCCGCCACCACGAACACCACCTGACCCCCTGGAAGCCCTGGTGGCGTCTTTTC

AGCTAG

SEQ ID NO: 2 [OB307-CrtW amino acid sequence]
213: Unknown

220:

221: Amino acid sequence

222: Derived from *Brevundimonas* strain OB307 crtW

223: Bacterium of the genus *Brevundimonas*
MetSerAlaValThrProMetSerArgValValProAsnGlnAlaLeu IleGlyLeuThrLeuAlaGlyLeuIleAlaThrAlaTrpLeuSerLeu HisIleTyrGlyValTyrPheHisArgTrpThrMetTrpSerIleLeu ThrValProLeuIleValAlaPheGlnThrTrpLeuSerValGlyLeu PheIleValAlaHisAspAlaMetHisGlySerLeuAlaProGlyArg ProArgLeuAsnThrAlaIleGlySerLeuAlaLeuGlyLeuTyrAla GlyPheArgPheAlaProLeuLysThrAlaHisHisAlaHisHisAla AlaProGlyThrAlaAspAspProAspPheHisAlaAspAlaProArg AlaPheLeuProTrpPheTyrGlyPhePheArgThrTyrPheGlyTrp ArgGluLeuAlaValLeuThrValLeuValAlaValAlaValLeuIle LeuGlyAlaArgMetProAsnLeuLeuValPheTrpAlaAlaProAla LeuLeuSerAlaLeuGlnLeuPheThrPheGlyThrTrpLeuProHis -continued ArgHisThrAspAspAlaPheProAspHisHisAsnAlaArgThrSer ProPheGlyProIleLeuSerLeuLeuThrCysPheHisPheGlyArg HisHisGluHisHisLeuThrProTrpLysProTrpTrpArgLeuPhe Ser SEQ ID NO: 3 [CrtZ--Linker--OB307-CrtW amino acid sequence]:
213: Unknown

220:

221: Amino acid sequence

222: Derived from the *Pantoea ananatis* crtZ amino acid sequence (1-175), a ten amino acid synthetic linker peptide (176-185), and the *Brevundimonas* strain OB307 crtW sequence without the N-terminal methionine residue (186-425).

223: Bacterium of the genus *Brevundimonas*
MetLeuTrpIleTrpAsnAlaLeuIleValPheValThrValIleGly MetGluValValAlaAlaLeuAlaHisLysTyrIleMetHisGlyTrp GlyTrpGlyTrpHisLeuSerHisHisGluProArgLysGlyAlaPhe GluValAsnAspLeuTyrAlaValValPheAlaAlaLeuSerIleLeu LeuIleTyrLeuGlySerThrGlyMetTrpProLeuGlnTrpIleGly AlaGlyMetThrAlaTyrGlyLeuLeuTyrPheMetValHisAspGly LeuValHisGlnArgTrpProPheArgTyrIleProArgLysGlyTyr LeuLysArgLeuTyrMetAlaHisArgMetHisHisAlaValArgGly LysGluGlyCysValSerPheGlyPheLeuTyrAlaProProLeuSer LysLeuGlnAlaThrLeuArgGluArgHisGlyAlaArgAlaGlyAla AlaArgAspAlaGlnGlyGlyGluAspGluProAlaSerGlyLysGly GlyGlyGlySerGlyGlyProGlySerSerAlaValThrProMetSer ArgValValProAsnGlnAlaLeuIleGlyLeuThrLeuAlaGlyLeu IleAlaThrAlaTrpLeuSerLeuHisIleTyrGlyValTyrPheHis ArgTrpThrMetTrpSerIleLeuThrValProLeuIleValAlaPhe GlnThrTrpLeuSerValGlyLeuPheIleValAlaHisAspAlaMet HisGlySerLeuAlaProGlyArgProArgLeuAsnThrAlaIleGly SerLeuAlaLeuGlyLeuTyrAlaGlyPheArgPheAlaProLeuLys ThrAlaHisHisAlaHisHisAlaAlaProGlyThrAlaAspAspPro AspPheHisAlaAspAlaProArgAlaPheLeuProTrpPheTyrGly PhePheArgThrTyrPheGlyTrpArgGluLeuAlaValLeuThrVal LeuValAlaValAlaValLeuIleLeuGlyAlaArgMetProAsnLeu LeuValPheTrpAlaAlaProAlaLeuLeuSerAlaLeuGlnLeuPhe ThrPheGlyThrTrpLeuProHisArgHisThrAspAspAlaPhePro AspHisHisAsnAlaArgThrSerProPheGlyProIleLeuSerLeu LeuThrCysPheHisPheGlyArgHisHisGluHisHisLeuThrPro TrpLysProTrpTrpArgLeuPheSer -continued SEQ ID NO: 4 [crtZ--Linker--OB307-crtW DNA sequence]:

213: Unknown

220:

221: Nucleic acid sequence

222: Synthetic nucleotide sequence derived from the *Pantoea ananatis* crtZ amino acid sequence (1-525), a synthetic linker sequence(526-555), and the *Brevundimonas* strain OB307 crtW sequence without the N-terminal methionine residue (556-1275).

223: Bacterium of the genus *Brevundimonas*
ATGCTGTGGATCTGGAACGCCCTGATCGTTTTCGTGACCGTGATCGGCATGGAAGTGGTG

GCCGCCCTGGCCCATAAGTACATCATGCACGGCTGGGGCTGGGGCTGGCACCTGTCGCAC

CACGAACCACGCAAAGGCGCATTTGAGGTGAATGACCTGTATGCCGTGGTGTTCGCCGCC

CTGTCGATTCTGCTGATCTATCTGGGCTCGACTGGCATGTGGCCGCTGCAGTGGATTGGC

GCCGGCATGACCGCATACGGCCTGCTGTACTTTATGGTTCATGACGGCCTGGTGCACCAG

CGCTGGCCGTTCCGCTACATCCCGCGCAAAGGCTATCTGAAACGCCTGTACATGGCCCAC

CGCATGCACCATGCAGTGCGCGGCAAGGAGGGCTGTGTGTCATTCGGCTTTCTGTACGCC

CCGCCGCTGTCGAAGCTGCAGGCCACTCTGCGCGAGAGACATGGCGCCCGCGCCGGCGCA

GCCCGCGATGCCCAAGGCGGCGAGGACGAGCCGGCATCGGGCAAAGGCGGGGGCGGGTCC

GGCGGCCCGGGGTCGTCGGCCGTGACCCCGATGTCGAGAGTGGTGCCAAACCAGGCCCTA

ATCGGCCTGACTTTAGCGGGGCTGATAGCCACGGCGTGGCTGAGTCTGCATATTTACGGG

GTGTACTTCCATCGTTGGACAATGTGGTCGATCCTGACGGTGCCGCTGATCGTGGCCTTC

CAGACGTGGCTGTCGGTAGGCCTGTTCATCGTTGCCCACGACGCAATGCACGGCTCCCTA

GCCCCGGGGAGGCCCCGCCTGAACACCGCCATCGGGTCCCTGGCCCTAGGCCTGTACGCT

GGCTTCAGGTTCGCCCCTCTGAAGACCGCCCACCATGCCCACCATGCCGCACCGGGCACA

GCCGACGACCCGGATTTTCACGCGGACGCCCCCCGTGCGTTCCTGCCGTGGTTCTACGGC

TTTTTCCGTACCTACTTCGGCTGGAGGGAGCTGGCCGTGCTGACCGTGTTGGTGGCCGTG

GCTGTTTTAATCCTGGGCGCCCGAATGCCGAACTTACTTGTGTTCTGGGCCGCCCCGGCT

CTATTATCGGCCTTGCAGCTTTTCACCTTCGGCACATGGCTGCCGCACCGACACACCGAC

GACGCCTTCCCGGACCACCACAACGCTCGCACTTCACCCTTTGGCCCCATCCTGTCTCTG

CTGACCTGCTTCCACTTCGGCCGGCACCATGAGCACCACCTGACTCCGTGGAAACCGTGG

TGGAGGCTGTTCTCGTAG

SEQ ID NO: 5 [System 1, insert only, 6449 bp]:
213: Unknown

220:

221: Nucleic acid sequence

222: Synthetic nucleotide sequence derived from the Pj5[E1A1C1C2] promoter (1-327), codon-optimized crtE from *Pantoea agglomerans* M87280/M99707 pAC-BETA plasmid (328-1,251), spacer sequence (1,252-1,291), RBS (1,292-1,305), codon-optimized crtY from *Pantoea agglomerans* M87280/M99707 pAC-BETA plasmid (1,306-2,466), spacer sequence (2,467-2,509), RBS (2,510-2,523), codon-optimized crtI from *Pantoea agglomerans* M87280/M99707 pAC-BETA plasmid (2,524-4,002), spacer sequence (4,003-4,046), RBS (4,047-4,060), codon-optimized crtB from *Pantoea agglomerans* M87280/M99707 pAC-BETA plasmid (4,061-4,990), spacer sequence (4,991-5,031), RBS (5,032-5,045), codon-optimized crtZ from *Pantoea ananatis* Strain AJ13355

-continued

NC_017533 in plasmid pEA-320 (5,046-5,573), spacer sequence (5,574-5,612), RBS (5,613-5,626), codon-optimized crtW from *Brevundimonas* strain OB307 (5,627-6,352), ending spacer sequence (6,353-6,371), *E. coli* rrnB terminator (6,372-6,443), and AseI restriction site (6,444-6,449).

223: Synthesized

AGTCCATTGTTGCCTTGCAACGCACGCGCTGTCAATGCGGGAATCCGCCTCGGCACTGCA

CGCTTCCCGACCTACCGGACGGTATGCAGCGCTCGCATCTGCCGAGGCCCCAGAGCATAG

GCGAGAAGGATGAATTTTTGATGTACATCGTGGCCATTGCTGCAGAGCGGATATAAAAAC

CGTTATTGACACAGGTGGAAATTTAAAATATACTGTTAGTAAACCTAATGGATCGACCTT

GAATTCAAAAGATCTGGGAGACCACAACGGTTTCCCTCTAGAAATAATTTTGGAATTCAA

AAGATCTTTTAAGAAGGAGATATACATATGGTGTCGGGCTCGAAGGCCGGCGTGTCGCCG

CACCGCGAGATCGAGGTGATGCGCCAGTCGATCGACGACCACCTGGCCGGCCTGCTGCCG

GAGACCGACTCGCAGGACATCGTGTCGCTGGCCATGCGCGAGGGCGTGATGGCCCCGGGC

AAGCGCATCCGCCCGCTGCTGATGCTGCTGGCCGCCCGCGACCTGCGCTACCAGGGCTCG

ATGCCGACCCTGCTGGACCTGGCCTGCGCCGTGGAGCTGACCCACACCGCCTCGCTGATG

CTGGACGACATGCCGTGCATGGACAACGCCGAGCTGCGCCGCGGCCAGCCGACCACCCAC

AAGAAGTTCGGCGAGTCGGTGGCCATCCTGGCCTCGGTGGGCCTGCTGTCGAAGGCCTTC

GGCCTGATCGCCGCCACCGGCGACCTGCCGGGCGAGCGCCGCGCCCAGGCCGTGAACGAG

CTGTCGACCGCCGTGGGCGTGCAGGGCCTGGTGCTGGGCCAGTTCCGCGACCTGAACGAC

GCCGCCCTGGACCGCACCCCGGACGCCATCCTGTCGACCAACCACCTGAAGACCGGCATC

CTGTTCTCGGCCATGCTGCAGATCGTGGCCATCGCCTCGGCCTCGTCGCCGTCGACCCGC

GAGACCCTGCACGCCTTCGCCCTGGACTTCGGCCAGGCCTTCCAGCTCCTGGACGACCTG

CGCGACGACCACCCGGAGACCGGCAAGGACCGCAACAAGGACGCCGGCAAGTCGACCCTG

GTGAACCGCCTGGGCGCCGACGCCGCCCGCCAGAAGCTGCGCGAGCACATCGACTCGGCC

GACAAGCACCTGACCTTCGCCTGCCCGCAGGGCGGCGCCATCCGCCAGTTCATGCACCTG

TGGTTCGGCCACCACCTGGCCGACTGGTCGCCGGTGATGAAGATCGCCTGAGTCATAGCT

GTTTCCTGCCCAGTCACGACGTTGTAAAACGCAAAGGAGATATAGGTGCGCGACCTGATC

CTGGTGGGCGGCGGCCTGGCCAACGGCCTGATCGCCTGGCGCCTGCGCCAGCGCTACCCG

CAGCTCAACCTGCTGCTGATCGAGGCCGGCGAGCAGCCGGGCGGCAACCACACCTGGTCG

TTCCACGAGGACGACCTGACCCCGGGCCAGCACGCCTGGCTGGCCCCGCTGGTGGCCCAC

GCCTGGCCGGGCTACGAGGTGCAGTTCCCGGACCTGCGCCGCCGCCTGGCCCGCGGCTAC

TACTCGATCACCTCGGAGCGCTTCGCCGAGGCCCTGCACCAGGCCCTGGGCGAGAACATC

TGGCTGAACTGCTCGGTGTCGGAGGTGCTGCCGAACTCGGTGCGCCTGGCCAACGGCGAG

GCCCTGCTGGCCGGCGCCGTGATCGACGGCCGCGGCGTGACCGCCTCGTCGGCCATGCAG

ACCGGCTACCAGCTCTTCCTGGGCCAGCAGTGGCGCCTGACCCAGCCGCACGGCCTGACC

GTGCCGATCCTGATGGACGCCACCGTGGCCCAGCAGCAGGGCTACCGCTTCGTGTACACC

CTGCCGCTGTCGGCCGACACCCTGCTGATCGAGGACACCCGCTACGCCAACGTGCCGCAG

CGCGACGACAACGCCCTGCGCCAGACCGTGACCGACTACGCCCACTCGAAGGGCTGGCAG

CTCGCCCAGCTCGAACGCGAGGAGACCGGCTGCCTGCCGATCACCCTGGCCGGCGACATC

CAGGCCCTGTGGGCCGACGCCCCGGGCGTGCCGCGCTCGGGCATGCGCGCCGGCCTGTTC

CACCCGACCACCGGCTACTCGCTGCCGCTGGCCGTGGCCCTGGCCGACGCCATCGCCGAC

TCGCCGCGCCTGGGCTCGGTGCCGCTGTACCAGCTCACCCGCCAGTTCGCCGAGCGCCAC

-continued

TGGCGCCGCCAGGGCTTCTTCCGCCTGCTGAACCGCATGCTGTTCCTGGCCGGCCGCGAG

GAGAACCGCTGGCGCGTGATGCAGCGCTTCTACGGCCTGCCGGAGCCGACCGTGGAGCGC

TTCTACGCCGGCCGCCTGTCGCTGTTCGACAAGGCCCGCATCCTGACCGGCAAGCCGCCG

GTGCCGCTGGGCGAGGCCTGCCGCGCCGCCCTGAACCACTTCCCGGACCGCCGCGACAAG

GGCTGACCTGTGTGAAATTGTTATCCGCTTACCCATACGACGTCCCAGACAAAGGAGATA

TAGATGAAGAAGACCGTGGTGATCGGCGCCGGCTTCGGCGGCCTGGCCCTGGCCATCCGC

CTGCAGGCCGCCGGCATCCCGACCGTGCTGCTGGAGCAGCGCGACAAGCCGGGCGGCCGC

GCCTACGTGTGGCACGACCAGGGCTTCACCTTCGACGCCGGCCCGACCGTGATCACCGAC

CCGACCGCCCTGGAGGCCCTGTTCACCCTGGCCGGCCGCCGCATGGAGGACTACGTGCGC

CTGCTGCCGGTGAAGCCGTTCTACCGCCTGTGCTGGGAGTCGGGCAAGACCCTGGACTAC

GCCAACGACTCGGCCGAGCTGGAGGCCCAGATCACCCAGTTCAACCCGCGCGACGTGGAG

GGCTACCGCCGCTTCCTGGCCTACTCGCAGGCCGTGTTCCAGGAGGGCTACCTGCGCCTG

GGCTCGGTGCCGTTCCTGTCGTTCCGCGACATGCTGCGCGCCGGCCCGCAGCTCCTGAAG

CTGCAGGCCTGGCAGTCGGTGTACCAGTCGGTGTCGCGCTTCATCGAGGACGAGCACCTG

CGCCAGGCCTTCTCGTTCCACTCGCTGCTGGTGGGCGGCAACCCGTTCACCACCTCGTCG

ATCTACACCCTGATCCACGCCCTGGAGCGCGAGTGGGGCGTGTGGTTCCCGGAGGGCGGC

ACCGGCGCCCTGGTGAACGGCATGGTGAAGCTGTTCACCGACCTGGGCGGCGAGATCGAG

CTGAACGCCCGCGTGGAGGAGCTGGTGGTGGCCGACAACCGCGTGTCGCAGGTGCGCCTG

GCCGACGGCCGCATCTTCGACACCGACGCCGTGGCCTCGAACGCCGACGTGGTGAACACC

TACAAGAAGCTGCTGGGCCACCACCCGGTGGGCCAGAAGCGCGCCGCCGCCCTGGAGCGC

AAGTCGATGTCGAACTCGCTGTTCGTGCTGTACTTCGGCCTGAACCAGCCGCACTCGCAG

CTCGCCCACCACACCATCTGCTTCGGCCCGCGCTACCGCGAGCTGATCGACGAGATCTTC

ACCGGCTCGGCCCTGGCCGACGACTTCTCGCTGTACCTGCACTCGCCGTGCGTGACCGAC

CCGTCGCTGGCCCCGCCGGGCTGCGCCTCGTTCTACGTGCTGGCCCCGGTGCCGCACCTG

GGCAACGCCCCGCTGGACTGGGCCCAGGAGGGCCCGAAGCTGCGCGACCGCATCTTCGAC

TACCTGGAGGAGCGCTACATGCCGGGCCTGCGCTCGCAGCTCGTGACCCAGCGCATCTTC

ACCCCGGCCGACTTCCACGACACCCTGGACGCCCACCTGGGCTCGGCCTTCTCGATCGAG

CCGCTGCTGACCCAGTCGGCCTGGTTCCGCCCGCACAACCGCGACTCGGACATCGCCAAC

CTGTACCTGGTGGGCGCCGGCACCCACCCGGGCGCCGGCATCCCGGGCGTGGTGGCCTCG

GCCAAGGCCACCGCCTCGCTGATGATCGAGGACCTGCAGTGATCTGGGACGTCGTATGGG

TAAGCTGGACATCACCTCCCACAACGCAAAGGAGATATAGATGTCGCAGCCGCCGCTGCT

GGACCACGCCACCCAGACCATGGCCAACGGCTCGAAGTCGTTCGCCACCGCCGCCAAGCT

GTTCGACCCGGCCACCCGCCGCTCGGTGCTGATGCTGTACACCTGGTGCCGCCACTGCGA

CGACGTGATCGACGACCAGACCCACGGCTTCGCCTCGGAGGCCGCCGCCGAGGAGGAGGC

CACCCAGCGCCTGGCCCGCCTGCGCACCCTGACCCTGGCCGCCTTCGAGGGCGCCGAGAT

GCAGGACCCGGCCTTCGCCGCCTTCCAGGAGGTGGCCCTGACCCACGGCATCACCCCGCG

CATGGCCCTGGACCACCTGGACGGCTTCGCCATGGACGTGGCCCAGACCCGCTACGTGAC

CTTCGAGGACACCCTGCGCTACTGCTACCACGTGGCCGGCGTGGTGGGCCTGATGATGGC

CCGCGTGATGGGCGTGCGCGACGAGCGCGTGCTGGACCGCGCCTGCGACCTGGGCCTGGC

CTTCCAGCTCACCAACATCGCCCGCGACATCATCGACGACGCCGCCATCGACCGCTGCTA

-continued

CCTGCCGGCCGAGTGGCTGCAGGACGCCGGCCTGACCCCGGAGAACTACGCCGCCCGCGA

GAACCGCGCCGCCCTGGCCCGCGTGGCCGAGCGCCTGATCGACGCCGCCGAGCCGTACTA

CATCTCGTCGCAGGCCGGCCTGCACGACCTGCCGCCGCGCTGCGCCTGGGCCATCGCCAC

CGCCCGCTCGGTGTACCGCGAGATCGGCATCAAGGTGAAGGCCGCCGGCGGCTCGGCCTG

GGACCGCCGCCAGCACACCTCGAAGGGCGAGAAGATCGCCATGCTGATGGCCGCCCCGGG

CCAGGTGATCCGCGCCAAGACCACCCGCGTGACCCCGCGCCCGGCCGGCCTGTGGCAGCG

CCCGGTGTGACTGTCCCCCCAGTTCCAGTACCTGGTCATCATCCTGCCTTTCAAAGGAGA

TATAGATGCTGTGGATCTGGAACGCCCTGATCGTGTTCGTGACCGTGATCGGCATGGAGG

TGGTGGCCGCCCTGGCCCACAAGTACATCATGCACGGCTGGGGCTGGGGCTGGCACCTGT

CGCACCACGAGCCGCGCAAGGGCGCCTTCGAGGTGAACGACCTGTACGCCGTGGTGTTCG

CCGCCCTGTCGATCCTGCTGATCTACCTGGGCTCGACCGGCATGTGGCCGCTGCAGTGGA

TCGGCGCCGGCATGACCGCCTACGGCCTGCTGTACTTCATGGTGCACGACGGCCTGGTGC

ACCAGCGCTGGCCGTTCCGCTACATCCCGCGCAAGGGCTACCTGAAGCGCCTGTACATGG

CCCACCGCATGCACCACGCCGTGCGCGGCAAGGAGGGCTGCGTGTCGTTCGGCTTCCTGT

ACGCCCCGCCGCTGTCGAAGCTGCAGGCCACCCTGCGCGAGCGCCACGGCGCCCGCGCCG

GCGCCGCCCGCGACGCCCAGGGCGGCGAGGACGAGCCGGCCTCGGGCAAGTGAGTTATAT

GGAGGGGGCAAACGCTCTAGAACTAGTGGATCCAAAGGAGATATAGATGTCGGCCGTGAC

CCCGATGTCGAGAGTGGTGCCAAACCAGGCCCTAATCGGCCTGACTTTAGCGGGGCTGAT

AGCCACGGCGTGGCTGAGTCTGCATATTTACGGGGTGTACTTCCATCGTTGGACAATGTG

GTCGATCCTGACGGTGCCGCTGATCGTGGCCTTCCAGACGTGGCTGTCGGTAGGCCTGTT

CATCGTTGCCCACGACGCAATGCACGGCTCCCTAGCCCCGGGGAGGCCCCGCCTGAACAC

CGCCATCGGGTCCCTGGCCCTAGGCCTGTACGCTGGCTTCAGGTTCGCCCCTCTGAAGAC

CGCCCACCATGCCCACCATGCCGCACCGGGCACAGCCGACGACCCGGATTTTCACGCGGA

CGCCCCCCGTGCGTTCCTGCCGTGGTTCTACGGCTTTTTCCGTACCTACTTCGGCTGGAG

GGAGCTGGCCGTGCTGACCGTGTTGGTGGCCGTGGCTGTTTTAATCCTGGGCGCCCGAAT

GCCGAACTTACTTGTGTTCTGGGCCGCCCCGGCTCTATTATCGGCCTTGCAGCTTTTCAC

CTTCGGCACATGGCTGCCGCACCGACACACCGACGACGCCTTCCCGGACCACCACAACGC

TCGCACTTCACCCTTTGGCCCCATCCTGTCTCTGCTGACCTGCTTCCACTTCGGCCGGCA

CCATGAGCACCACCTGACTCCGTGGAAACCGTGGTGGAGGCTGTTCTCGTAGCGATACCG

TCGACTTCGAGCAAATAAAACGAAAGGCTCAGTCGAAAGACTGGGCCTTTCGTTTTATCT

GTTGTTTGTCGGTGAACGCTCTCATTAAT

SEQ ID NO: 6 [System 2, insert only, 5868 bp]:
213: Unknown

220:

221: Nucleic acid sequence

222: Synthetic nucleotide sequence derived from the Pj5[E1A1C1C2] promoter (1-327), codon-optimized crtE from *Pantoea agglomerans* M87280/M99707 pAC-BETA plasmid (328-1,251), spacer sequence (1,252-1,291), RBS (1,292-1,305), codon-optimized crtY from *Pantoea agglomerans* M87280/M99707 pAC-BETA plasmid (1,306-2,466), spacer sequence (2,467-2,509), RBS (2,510-2,523), codon-optimized crtI from *Pantoea agglomerans* M87280/M99707 pAC-BETA plasmid (2,524-4,002), spacer sequence (4,003-4,046), RBS (4,047-4,060), codon-optimized crtB from *Pantoea agglomerans* M87280/M99707 pAC-BETA plasmid (4,061-4,990), spacer sequence (4,991-5,037), -continued RBS (5,038-5,051), codon-optimized crtW from *Brevundimonas* strain OB307 (5,052-5,777), ending spacer sequence (5,778-5,796), and *E. coli* rrnB terminator (5,797-5,868).

223: Synthesized

AGTCCATTGTTGCCTTGCAACGCACGCGCTGTCAATGCGGGAATCCGCCTCGGCACTGCA

CGCTTCCCGACCTACCGGACGGTATGCAGCGCTCGCATCTGCCGAGGCCCCAGAGCATAG

GCGAGAAGGATGAATTTTTGATGTACATCGTGGCCATTGCTGCAGAGCGGATATAAAAAC

CGTTATTGACACAGGTGGAAATTTAAAATATACTGTTAGTAAACCTAATGGATCGACCTT

GAATTCAAAAGATCTGGGAGACCACAACGGTTTCCCTCTAGAAATAATTTTGGAATTCAA

AAGATCTTTTAAGAAGGAGATATACATATGGTGTCGGGCTCGAAGGCCGGCGTGTCGCCG

CACCGCGAGATCGAGGTGATGCGCCAGTCGATCGACGACCACCTGGCCGGCCTGCTGCCG

GAGACCGACTCGCAGGACATCGTGTCGCTGGCCATGCGCGAGGGCGTGATGGCCCCGGGC

AAGCGCATCCGCCCGCTGCTGATGCTGCTGGCCGCCCGCGACCTGCGCTACCAGGGCTCG

ATGCCGACCCTGCTGGACCTGGCCTGCGCCGTGGAGCTGACCCACACCGCCTCGCTGATG

CTGGACGACATGCCGTGCATGGACAACGCCGAGCTGCGCCGCGGCCAGCCGACCACCCAC

AAGAAGTTCGGCGAGTCGGTGGCCATCCTGGCCTCGGTGGGCCTGCTGTCGAAGGCCTTC

GGCCTGATCGCCGCCACCGGCGACCTGCCGGGCGAGCGCCGCGCCCAGGCCGTGAACGAG

CTGTCGACCGCCGTGGGCGTGCAGGGCCTGGTGCTGGGCCAGTTCCGCGACCTGAACGAC

GCCGCCCTGGACCGCACCCCGGACGCCATCCTGTCGACCAACCACCTGAAGACCGGCATC

CTGTTCTCGGCCATGCTGCAGATCGTGGCCATCGCCTCGGCCTCGTCGCCGTCGACCCGC

GAGACCCTGCACGCCTTCGCCCTGGACTTCGGCCAGGCCTTCCAGCTCCTGGACGACCTG

CGCGACGACCACCCGGAGACCGGCAAGGACCGCAACAAGGACGCCGGCAAGTCGACCCTG

GTGAACCGCCTGGGCGCCGACGCCGCCCGCCAGAAGCTGCGCGAGCACATCGACTCGGCC

GACAAGCACCTGACCTTCGCCTGCCCGCAGGGCGGCGCCATCCGCCAGTTCATGCACCTG

TGGTTCGGCCACCACCTGGCCGACTGGTCGCCGGTGATGAAGATCGCCTGAGTCATAGCT

GTTTCCTGCCCAGTCACGACGTTGTAAAACGCAAAGGAGATATAGGTGCGCGACCTGATC

CTGGTGGGCGGCGGCCTGGCCAACGGCCTGATCGCCTGGCGCCTGCGCCAGCGCTACCCG

CAGCTCAACCTGCTGCTGATCGAGGCCGGCGAGCAGCCGGGCGGCAACCACACCTGGTCG

TTCCACGAGGACGACCTGACCCCGGGCCAGCACGCCTGGCTGGCCCCGCTGGTGGCCCAC

GCCTGGCCGGGCTACGAGGTGCAGTTCCCGGACCTGCGCCGCCGCCTGGCCCGCGGCTAC

TACTCGATCACCTCGGAGCGCTTCGCCGAGGCCCTGCACCAGGCCCTGGGCGAGAACATC

TGGCTGAACTGCTCGGTGTCGGAGGTGCTGCCGAACTCGGTGCGCCTGGCCAACGGCGAG

GCCCTGCTGGCCGGCGCCGTGATCGACGGCCGCGGCGTGACCGCCTCGTCGGCCATGCAG

ACCGGCTACCAGCTCTTCCTGGGCCAGCAGTGGCGCCTGACCCAGCCGCACGGCCTGACC

GTGCCGATCCTGATGGACGCCACCGTGGCCCAGCAGCAGGGCTACCGCTTCGTGTACACC

CTGCCGCTGTCGGCCGACACCCTGCTGATCGAGGACACCCGCTACGCCAACGTGCCGCAG

CGCGACGACAACGCCCTGCGCCAGACCGTGACCGACTACGCCCACTCGAAGGGCTGGCAG

CTCGCCCAGCTCGAACGCGAGGAGACCGGCTGCCTGCCGATCACCCTGGCCGGCGACATC

CAGGCCCTGTGGGCCGACGCCCCGGGCGTGCCGCGCTCGGGCATGCGCGCCGGCCTGTTC

CACCCGACCACCGGCTACTCGCTGCCGCTGGCCGTGGCCCTGGCCGACGCCATCGCCGAC

TCGCCGCGCCTGGGCTCGGTGCCGCTGTACCAGCTCACCCGCCAGTTCGCCGAGCGCCAC

TGGCGCCGCCAGGGCTTCTTCCGCCTGCTGAACCGCATGCTGTTCCTGGCCGGCCGCGAG

-continued

GAGAACCGCTGGCGCGTGATGCAGCGCTTCTACGGCCTGCCGGAGCCGACCGTGGAGCGC

TTCTACGCCGGCCGCCTGTCGCTGTTCGACAAGGCCCGCATCCTGACCGGCAAGCCGCCG

GTGCCGCTGGGCGAGGCCTGCCGCGCCGCCCTGAACCACTTCCCGGACCGCCGCGACAAG

GGCTGACCTGTGTGAAATTGTTATCCGCTTACCCATACGACGTCCCAGACAAAGGAGATA

TAGATGAAGAAGACCGTGGTGATCGGCGCCGGCTTCGGCGGCCTGGCCCTGGCCATCCGC

CTGCAGGCCGCCGGCATCCCGACCGTGCTGCTGGAGCAGCGCGACAAGCCGGGCGGCCGC

GCCTACGTGTGGCACGACCAGGGCTTCACCTTCGACGCCGGCCCGACCGTGATCACCGAC

CCGACCGCCCTGGAGGCCCTGTTCACCCTGGCCGGCCGCCGCATGGAGGACTACGTGCGC

CTGCTGCCGGTGAAGCCGTTCTACCGCCTGTGCTGGGAGTCGGGCAAGACCCTGGACTAC

GCCAACGACTCGGCCGAGCTGGAGGCCCAGATCACCCAGTTCAACCCGCGCGACGTGGAG

GGCTACCGCCGCTTCCTGGCCTACTCGCAGGCCGTGTTCCAGGAGGGCTACCTGCGCCTG

GGCTCGGTGCCGTTCCTGTCGTTCCGCGACATGCTGCGCGCCGGCCCGCAGCTCCTGAAG

CTGCAGGCCTGGCAGTCGGTGTACCAGTCGGTGTCGCGCTTCATCGAGGACGAGCACCTG

CGCCAGGCCTTCTCGTTCCACTCGCTGCTGGTGGGCGGCAACCCGTTCACCACCTCGTCG

ATCTACACCCTGATCCACGCCCTGGAGCGCGAGTGGGGCGTGTGGTTCCCGGAGGGCGGC

ACCGGCGCCCTGGTGAACGGCATGGTGAAGCTGTTCACCGACCTGGGCGGCGAGATCGAG

CTGAACGCCCGCGTGGAGGAGCTGGTGGTGGCCGACAACCGCGTGTCGCAGGTGCGCCTG

GCCGACGGCCGCATCTTCGACACCGACGCCGTGGCCTCGAACGCCGACGTGGTGAACACC

TACAAGAAGCTGCTGGGCCACCACCCGGTGGGCCAGAAGCGCGCCGCCGCCCTGGAGCGC

AAGTCGATGTCGAACTCGCTGTTCGTGCTGTACTTCGGCCTGAACCAGCCGCACTCGCAG

CTCGCCCACCACACCATCTGCTTCGGCCCGCGCTACCGCGAGCTGATCGACGAGATCTTC

ACCGGCTCGGCCCTGGCCGACGACTTCTCGCTGTACCTGCACTCGCCGTGCGTGACCGAC

CCGTCGCTGGCCCCGCCGGGCTGCGCCTCGTTCTACGTGCTGGCCCCGGTGCCGCACCTG

GGCAACGCCCCGCTGGACTGGGCCCAGGAGGGCCCGAAGCTGCGCGACCGCATCTTCGAC

TACCTGGAGGAGCGCTACATGCCGGGCCTGCGCTCGCAGCTCGTGACCCAGCGCATCTTC

ACCCCGGCCGACTTCCACGACACCCTGGACGCCCACCTGGGCTCGGCCTTCTCGATCGAG

CCGCTGCTGACCCAGTCGGCCTGGTTCCGCCCGCACAACCGCGACTCGGACATCGCCAAC

CTGTACCTGGTGGGCGCCGGCACCCACCCGGGCGCCGGCATCCCGGGCGTGGTGGCCTCG

GCCAAGGCCACCGCCTCGCTGATGATCGAGGACCTGCAGTGATCTGGGACGTCGTATGGG

TAAGCTGGACATCACCTCCCACAACGCAAAGGAGATATAGATGTCGCAGCCGCCGCTGCT

GGACCACGCCACCCAGACCATGGCCAACGGCTCGAAGTCGTTCGCCACCGCCGCCAAGCT

GTTCGACCCGGCCACCCGCCGCTCGGTGCTGATGCTGTACACCTGGTGCCGCCACTGCGA

CGACGTGATCGACGACCAGACCCACGGCTTCGCCTCGGAGGCCGCCGCCGAGGAGGAGGC

CACCCAGCGCCTGGCCCGCCTGCGCACCCTGACCCTGGCCGCCTTCGAGGGCGCCGAGAT

GCAGGACCCGGCCTTCGCCGCCTTCCAGGAGGTGGCCCTGACCCACGGCATCACCCCGCG

CATGGCCCTGGACCACCTGGACGGCTTCGCCATGGACGTGGCCCAGACCCGCTACGTGAC

CTTCGAGGACACCCTGCGCTACTGCTACCACGTGGCCGGCGTGGTGGGCCTGATGATGGC

CCGCGTGATGGGCGTGCGCGACGAGCGCGTGCTGGACCGCGCCTGCGACCTGGGCCTGGC

CTTCCAGCTCACCAACATCGCCCGCGACATCATCGACGACGCCGCCATCGACCGCTGCTA

CCTGCCGGCCGAGTGGCTGCAGGACGCCGGCCTGACCCCGGAGAACTACGCCGCCCGCGA

-continued

GAACCGCGCCGCCCTGGCCCGCGTGGCCGAGCGCCTGATCGACGCCGCCGAGCCGTACTA

CATCTCGTCGCAGGCCGGCCTGCACGACCTGCCGCCGCGCTGCGCCTGGGCCATCGCCAC

CGCCCGCTCGGTGTACCGCGAGATCGGCATCAAGGTGAAGGCCGCCGGCGGCTCGGCCTG

GGACCGCCGCCAGCACACCTCGAAGGGCGAGAAGATCGCCATGCTGATGGCCGCCCCGGG

CCAGGTGATCCGCGCCAAGACCACCCGCGTGACCCCGCGCCCGGCCGGCCTGTGGCAGCG

CCCGGTGTGACTGTCCCCGTTATATGGAGGGGGCAAACGCTCTAGAACTAGTGGATCCAA

AGGAGATATAGATGTCGGCCGTGACCCCGATGTCGAGAGTGGTGCCAAACCAGGCCCTAA

TCGGCCTGACTTTAGCGGGGCTGATAGCCACGGCGTGGCTGAGTCTGCATATTTACGGGG

TGTACTTCCATCGTTGGACAATGTGGTCGATCCTGACGGTGCCGCTGATCGTGGCCTTCC

AGACGTGGCTGTCGGTAGGCCTGTTCATCGTTGCCCACGACGCAATGCACGGCTCCCTAG

CCCCGGGGAGGCCCCGCCTGAACACCGCCATCGGGTCCCTGGCCCTAGGCCTGTACGCTG

GCTTCAGGTTCGCCCCTCTGAAGACCGCCCACCATGCCCACCATGCCGCACCGGGCACAG

CCGACGACCCGGATTTTCACGCGGACGCCCCCCGTGCGTTCCTGCCGTGGTTCTACGGCT

TTTTCCGTACCTACTTCGGCTGGAGGGAGCTGGCCGTGCTGACCGTGTTGGTGGCCGTGG

CTGTTTTAATCCTGGGCGCCCGAATGCCGAACTTACTTGTGTTCTGGGCCGCCCCGGCTC

TATTATCGGCCTTGCAGCTTTTCACCTTCGGCACATGGCTGCCGCACCGACACACCGACG

ACGCCTTCCCGGACCACCACAACGCTCGCACTTCACCCTTTGGCCCCATCCTGTCTCTGC

TGACCTGCTTCCACTTCGGCCGGCACCATGAGCACCACCTGACTCCGTGGAAACCGTGGT

GGAGGCTGTTCTCGTAGCGATACCGTCGACTTCGAGCAAATAAAACGAAAGGCTCAGTCG

AAAGACTGGGCCTTTCGTTTTATCTGTTGTTTGTCGGTGAACGCTCT

SEQ ID NO: 7 [System 3, insert only, 6462 bp]:
213: Unknown

220:

221: Nucleic acid sequence

222: Synthetic nucleotide sequence derived from the Pj5[E1A1C1C2] promoter (1-327), codon-optimized crtE from *Pantoea agglomerans* M87280/M99707 pAC-BETA plasmid (328-1,251), spacer sequence (1,252-1,291), RBS (1,292-1,305), codon-optimized crtY from *Pantoea agglomerans* M87280/M99707 pAC-BETA plasmid (1,306-2,466), spacer sequence (2,467-2,509), RBS (2,510-2,523), codon-optimized crtI from *Pantoea agglomerans* M87280/M99707 pAC-BETA plasmid (2,524-4,002), spacer sequence (4,003-4,046), RBS (4,047-4,060), codon-optimized crtB from *Pantoea agglomerans* M87280/M99707 pAC-BETA plasmid (4,061-4,990), spacer sequence (4,991-5,080), RBS (5,081-5,093), a codon-optimized crtZW fusion containing the crtZ gene from *Pantoea ananatis* Strain AJ13355 NC_017533, a 30-bp sequence encoding a linker peptide, and the crtW gene from *Brevundimonas* strain OB307 without the N-terminal methionine (5,094-6,371), ending spacer sequence (6,372-6,390), and *E. coli* rrnB terminator (6,391-6,462).

223: Synthesized
AGTCCATTGTTGCCTTGCAACGCACGCGCTGTCAATGCGGGAATCCGCCTCGGCACTGCA

CGCTTCCCGACCTACCGGACGGTATGCAGCGCTCGCATCTGCCGAGGCCCCAGAGCATAG

GCGAGAAGGATGAATTTTTGATGTACATCGTGGCCATTGCTGCAGAGCGGATATAAAAAC

CGTTATTGACACAGGTGGAAATTTAAAATATACTGTTAGTAAACCTAATGGATCGACCTT

GAATTCAAAAGATCTGGGAGACCACAACGGTTTCCCTCTAGAAATAATTTTGGAATTCAA

AAGATCTTTTAAGAAGGAGATATACATATGGTGTCGGGCTCGAAGGCCGGCGTGTCGCCG

CACCGCGAGATCGAGGTGATGCGCCAGTCGATCGACGACCACCTGGCCGGCCTGCTGCCG

-continued

GAGACCGACTCGCAGGACATCGTGTCGCTGGCCATGCGCGAGGGCGTGATGGCCCCGGGC

AAGCGCATCCGCCCGCTGCTGATGCTGCTGGCCGCCCGCGACCTGCGCTACCAGGGCTCG

ATGCCGACCCTGCTGGACCTGGCCTGCGCCGTGGAGCTGACCCACACCGCCTCGCTGATG

CTGGACGACATGCCGTGCATGGACAACGCCGAGCTGCGCCGCGGCCAGCCGACCACCCAC

AAGAAGTTCGGCGAGTCGGTGGCCATCCTGGCCTCGGTGGGCCTGCTGTCGAAGGCCTTC

GGCCTGATCGCCGCCACCGGCGACCTGCCGGGCGAGCGCCGCGCCCAGGCCGTGAACGAG

CTGTCGACCGCCGTGGGCGTGCAGGGCCTGGTGCTGGGCCAGTTCCGCGACCTGAACGAC

GCCGCCCTGGACCGCACCCCGGACGCCATCCTGTCGACCAACCACCTGAAGACCGGCATC

CTGTTCTCGGCCATGCTGCAGATCGTGGCCATCGCCTCGGCCTCGTCGCCGTCGACCCGC

GAGACCCTGCACGCCTTCGCCCTGGACTTCGGCCAGGCCTTCCAGCTCCTGGACGACCTG

CGCGACGACCACCCGGAGACCGGCAAGGACCGCAACAAGGACGCCGGCAAGTCGACCCTG

GTGAACCGCCTGGGCGCCGACGCCGCCCGCCAGAAGCTGCGCGAGCACATCGACTCGGCC

GACAAGCACCTGACCTTCGCCTGCCCGCAGGGCGGCGCCATCCGCCAGTTCATGCACCTG

TGGTTCGGCCACCACCTGGCCGACTGGTCGCCGGTGATGAAGATCGCCTGAGTCATAGCT

GTTTCCTGCCCAGTCACGACGTTGTAAAACGCAAAGGAGATATAGGTGCGCGACCTGATC

CTGGTGGGCGGCGGCCTGGCCAACGGCCTGATCGCCTGGCGCCTGCGCCAGCGCTACCCG

CAGCTCAACCTGCTGCTGATCGAGGCCGGCGAGCAGCCGGGCGGCAACCACACCTGGTCG

TTCCACGAGGACGACCTGACCCCGGGCCAGCACGCCTGGCTGGCCCCGCTGGTGGCCCAC

GCCTGGCCGGGCTACGAGGTGCAGTTCCCGGACCTGCGCCGCCGCCTGGCCCGCGGCTAC

TACTCGATCACCTCGGAGCGCTTCGCCGAGGCCCTGCACCAGGCCCTGGGCGAGAACATC

TGGCTGAACTGCTCGGTGTCGGAGGTGCTGCCGAACTCGGTGCGCCTGGCCAACGGCGAG

GCCCTGCTGGCCGGCGCCGTGATCGACGGCCGCGGCGTGACCGCCTCGTCGGCCATGCAG

ACCGGCTACCAGCTCTTCCTGGGCCAGCAGTGGCGCCTGACCCAGCCGCACGGCCTGACC

GTGCCGATCCTGATGGACGCCACCGTGGCCCAGCAGCAGGGCTACCGCTTCGTGTACACC

CTGCCGCTGTCGGCCGACACCCTGCTGATCGAGGACACCCGCTACGCCAACGTGCCGCAG

CGCGACGACAACGCCCTGCGCCAGACCGTGACCGACTACGCCCACTCGAAGGGCTGGCAG

CTCGCCCAGCTCGAACGCGAGGAGACCGGCTGCCTGCCGATCACCCTGGCCGGCGACATC

CAGGCCCTGTGGGCCGACGCCCCGGGCGTGCCGCGCTCGGGCATGCGCGCCGGCCTGTTC

CACCCGACCACCGGCTACTCGCTGCCGCTGGCCGTGGCCCTGGCCGACGCCATCGCCGAC

TCGCCGCGCCTGGGCTCGGTGCCGCTGTACCAGCTCACCCGCCAGTTCGCCGAGCGCCAC

TGGCGCCGCCAGGGCTTCTTCCGCCTGCTGAACCGCATGCTGTTCCTGGCCGGCCGCGAG

GAGAACCGCTGGCGCGTGATGCAGCGCTTCTACGGCCTGCCGGAGCCGACCGTGGAGCGC

TTCTACGCCGGCCGCCTGTCGCTGTTCGACAAGGCCCGCATCCTGACCGGCAAGCCGCCG

GTGCCGCTGGGCGAGGCCTGCCGCGCCGCCCTGAACCACTTCCCGGACCGCCGCGACAAG

GGCTGACCTGTGTGAAATTGTTATCCGCTTACCCATACGACGTCCCAGACAAAGGAGATA

TAGATGAAGAAGACCGTGGTGATCGGCGCCGGCTTCGGCGGCCTGGCCCTGGCCATCCGC

CTGCAGGCCGCCGGCATCCCGACCGTGCTGCTGGAGCAGCGCGACAAGCCGGGCGGCCGC

GCCTACGTGTGGCACGACCAGGGCTTCACCTTCGACGCCGGCCCGACCGTGATCACCGAC

CCGACCGCCCTGGAGGCCCTGTTCACCCTGGCCGGCCGCCGCATGGAGGACTACGTGCGC

CTGCTGCCGGTGAAGCCGTTCTACCGCCTGTGCTGGGAGTCGGGCAAGACCCTGGACTAC

-continued

GCCAACGACTCGGCCGAGCTGGAGGCCCAGATCACCCAGTTCAACCCGCGCGACGTGGAG

GGCTACCGCCGCTTCCTGGCCTACTCGCAGGCCGTGTTCCAGGAGGGCTACCTGCGCCTG

GGCTCGGTGCCGTTCCTGTCGTTCCGCGACATGCTGCGCGCCGGCCCGCAGCTCCTGAAG

CTGCAGGCCTGGCAGTCGGTGTACCAGTCGGTGTCGCGCTTCATCGAGGACGAGCACCTG

CGCCAGGCCTTCTCGTTCCACTCGCTGCTGGTGGGCGGCAACCCGTTCACCACCTCGTCG

ATCTACACCCTGATCCACGCCCTGGAGCGCGAGTGGGGCGTGTGGTTCCCGGAGGGCGGC

ACCGGCGCCCTGGTGAACGGCATGGTGAAGCTGTTCACCGACCTGGGCGGCGAGATCGAG

CTGAACGCCCGCGTGGAGGAGCTGGTGGTGGCCGACAACCGCGTGTCGCAGGTGCGCCTG

GCCGACGGCCGCATCTTCGACACCGACGCCGTGGCCTCGAACGCCGACGTGGTGAACACC

TACAAGAAGCTGCTGGGCCACCACCCGGTGGGCCAGAAGCGCGCCGCCGCCCTGGAGCGC

AAGTCGATGTCGAACTCGCTGTTCGTGCTGTACTTCGGCCTGAACCAGCCGCACTCGCAG

CTCGCCCACCACACCATCTGCTTCGGCCCGCGCTACCGCGAGCTGATCGACGAGATCTTC

ACCGGCTCGGCCCTGGCCGACGACTTCTCGCTGTACCTGCACTCGCCGTGCGTGACCGAC

CCGTCGCTGGCCCCGCCGGGCTGCGCCTCGTTCTACGTGCTGGCCCCGGTGCCGCACCTG

GGCAACGCCCCGCTGGACTGGGCCCAGGAGGGCCCGAAGCTGCGCGACCGCATCTTCGAC

TACCTGGAGGAGCGCTACATGCCGGGCCTGCGCTCGCAGCTCGTGACCCAGCGCATCTTC

ACCCCGGCCGACTTCCACGACACCCTGGACGCCCACCTGGGCTCGGCCTTCTCGATCGAG

CCGCTGCTGACCCAGTCGGCCTGGTTCCGCCCGCACAACCGCGACTCGGACATCGCCAAC

CTGTACCTGGTGGGCGCCGGCACCCACCCGGGCGCCGGCATCCCGGGCGTGGTGGCCTCG

GCCAAGGCCACCGCCTCGCTGATGATCGAGGACCTGCAGTGATCTGGGACGTCGTATGGG

TAAGCTGGACATCACCTCCCACAACGCAAAGGAGATATAGATGTCGCAGCCGCCGCTGCT

GGACCACGCCACCCAGACCATGGCCAACGGCTCGAAGTCGTTCGCCACCGCCGCCAAGCT

GTTCGACCCGGCCACCCGCCGCTCGGTGCTGATGCTGTACACCTGGTGCCGCCACTGCGA

CGACGTGATCGACGACCAGACCCACGGCTTCGCCTCGGAGGCCGCCGCCGAGGAGGAGGC

CACCCAGCGCCTGGCCCGCCTGCGCACCCTGACCCTGGCCGCCTTCGAGGGCGCCGAGAT

GCAGGACCCGGCCTTCGCCGCCTTCCAGGAGGTGGCCCTGACCCACGGCATCACCCCGCG

CATGGCCCTGGACCACCTGGACGGCTTCGCCATGGACGTGGCCCAGACCCGCTACGTGAC

CTTCGAGGACACCCTGCGCTACTGCTACCACGTGGCCGGCGTGGTGGGCCTGATGATGGC

CCGCGTGATGGGCGTGCGCGACGAGCGCGTGCTGGACCGCGCCTGCGACCTGGGCCTGGC

CTTCCAGCTCACCAACATCGCCCGCGACATCATCGACGACGCCGCCATCGACCGCTGCTA

CCTGCCGGCCGAGTGGCTGCAGGACGCCGGCCTGACCCCGGAGAACTACGCCGCCCGCGA

GAACCGCGCCGCCCTGGCCCGCGTGGCCGAGCGCCTGATCGACGCCGCCGAGCCGTACTA

CATCTCGTCGCAGGCCGGCCTGCACGACCTGCCGCCGCGCTGCGCCTGGGCCATCGCCAC

CGCCCGCTCGGTGTACCGCGAGATCGGCATCAAGGTGAAGGCCGCCGGCGGCTCGGCCTG

GGACCGCCGCCAGCACACCTCGAAGGGCGAGAAGATCGCCATGCTGATGGCCGCCCCGGG

CCAGGTGATCCGCGCCAAGACCACCCGCGTGACCCCGCGCCCGGCCGGCCTGTGGCAGCG

CCCGGTGTGACTGTCCCCGTTATATGGAGGGGGCAAACGCTCTAGAACTAGTGGATCCCT

GTCCCCCCAGTTCCAGTACCTGGTCATCATCCTGCCTTTCAAAGGAGATATAGATGCTGT

GGATCTGGAACGCCCTGATCGTTTTCGTGACCGTGATCGGCATGGAAGTGGTGGCCGCCC

TGGCCCATAAGTACATCATGCACGGCTGGGGCTGGGGCTGGCACCTGTCGCACCACGAAC

CACGCAAAGGCGCATTTGAGGTGAATGACCTGTATGCCGTGGTGTTCGCCGCCCTGTCGA

-continued

TTCTGCTGATCTATCTGGGCTCGACTGGCATGTGGCCGCTGCAGTGGATTGGCGCCGGCA

TGACCGCATACGGCCTGCTGTACTTTATGGTTCATGACGGCCTGGTGCACCAGCGCTGGC

CGTTCCGCTACATCCCGCGCAAAGGCTATCTGAAACGCCTGTACATGGCCCACCGCATGC

ACCATGCAGTGCGCGGCAAGGAGGGCTGTGTGTCATTCGGCTTTCTGTACGCCCCGCCGC

TGTCGAAGCTGCAGGCCACTCTGCGCGAGAGACATGGCGCCCGCGCCGGCGCAGCCCGCG

ATGCCCAAGGCGGCGAGGACGAGCCGGCATCGGGCAAAGGCGGGGGCGGGTCCGGCGGCC

CGGGGTCGTCGGCCGTGACCCCGATGTCGAGAGTGGTGCCAAACCAGGCCCTAATCGGCC

TGACTTTAGCGGGGCTGATAGCCACGGCGTGGCTGAGTCTGCATATTTACGGGGTGTACT

TCCATCGTTGGACAATGTGGTCGATCCTGACGGTGCCGCTGATCGTGGCCTTCCAGACGT

GGCTGTCGGTAGGCCTGTTCATCGTTGCCCACGACGCAATGCACGGCTCCCTAGCCCCGG

GGAGGCCCCGCCTGAACACCGCCATCGGGTCCCTGGCCCTAGGCCTGTACGCTGGCTTCA

GGTTCGCCCCTCTGAAGACCGCCCACCATGCCCACCATGCCGCACCGGGCACAGCCGACG

ACCCGGATTTTCACGCGGACGCCCCCCGTGCGTTCCTGCCGTGGTTCTACGGCTTTTTCC

GTACCTACTTCGGCTGGAGGGAGCTGGCCGTGCTGACCGTGTTGGTGGCCGTGGCTGTTT

TAATCCTGGGCGCCCGAATGCCGAACTTACTTGTGTTCTGGGCCGCCCCGGCTCTATTAT

CGGCCTTGCAGCTTTTCACCTTCGGCACATGGCTGCCGCACCGACACACCGACGACGCCT

TCCCGGACCACCACAACGCTCGCACTTCACCCTTTGGCCCCATCCTGTCTCTGCTGACCT

GCTTCCACTTCGGCCGGCACCATGAGCACCACCTGACTCCGTGGAAACCGTGGTGGAGGC

TGTTCTCGTAGCGATACCGTCGACTTCGAGCAAATAAAACGAAAGGCTCAGTCGAAAGAC

TGGGCCTTTCGTTTTATCTGTTGTTTGTCGGTGAACGCTCTC

SEQ ID NO: 8 [pDONRPEX18TC-Tn5 Insert with OB307-crtW (from attL1 to attL2), 8,861 bp]:

213: Unknown

220:

221: Nucleic acid sequence

222: Synthetic nucleotide sequence derived from the attL1 sequence (1-100), a spacer sequence (101-112), a Tn5 Mosaic End sequence (113-131), spacer sequence (132-236), the Pj5[E1A1C1C2] promoter (237-563), codon-optimized crtE from *Pantoea agglomerans* M87280/M99707 pAC-BETA plasmid (564-1,487), spacer sequence (1,488-1,525), RBS (1,526-1,541), codon-optimized crtY from *Pantoea agglomerans* M87280/M99707 pAC-BETA plasmid (1,542-2,702), spacer sequence (2,703-2,745), RBS (2,746-2,759), codon-optimized crtI from *Pantoea agglomerans* M87280/M99707 pAC-BETA plasmid (2,760-4,238), spacer sequence (4,239-4,282), RBS (4,283-4,296), codon-optimized crtB from *Pantoea agglomerans* M87280/M99707 pAC-BETA plasmid (4,297-5,226), spacer sequence (5,227-5,267), RBS (5,268-5,281), codon-optimized crtZ from *Pantoea ananatis* Strain AJ13355 NC_017533 in plasmid pEA-320 (5,282-5,809), spacer sequence (5,810-5,848), RBS (5,849-5,862), codon-optimized crtW from *Brevundimonas* strain OB307 (5,863-6,588), spacer sequence (6,589-6,607), *E. coli* rrnB terminator (6,608-6,679), and AseI restriction site (6,680-6,685), spacer sequence (6,686-7,093), a Tn5 Mosaic End sequence (7,094-7,112), a SpeI restriction site sequence (7,113-7,118), T0 terminator (7,119-7,221), spacer and promoter sequence (7,222-7,321), Tn5 transposase sequence (7,322-8,752), spacer sequence (8,753-8,761), and an attL2 sequence (8,762-8,861).

-continued

223: Synthesized
CAAATAATGATTTTATTTTGACTGATAGTGACCTGTTCGTTGCAACAMATTGATGAGCAA

TGCTTTTTTATAATGCCAACTTTGTACAAAAAAGCAGGCTTCAGGCCGAGGCCTGTCTCT

TATACACATCTTTGTGTCTCAGGCCGCCTAGGCCGCGGCCGCGCGAATTCGAGCTCGGTA

CCCGGGGATCCTCTAGAGTCGACCTGCAGGCATGCAAGCTTACCGGTTTATTATTAAGTC

CATTGTTGCCTTGCAACGCACGCGCTGTCAATGCGGGAATCCGCCTCGGCACTGCACGCT

TCCCGACCTACCGGACGGTATGCAGCGCTCGCATCTGCCGAGGCCCCAGAGCATAGGCGA

GAAGGATGAATTTTTGATGTACATCGTGGCCATTGCTGCAGAGCGGATATAAAAACCGTT

ATTGACACAGGTGGAAATTTAAAATATACTGTTAGTAAACCTAATGGATCGACCTTGAAT

TCAAAAGATCTGGGAGACCACAACGGTTTCCCTCTAGAAATAATTTTGGAATTCAAAAGA

TCTTTTAAGAAGGAGATATACATATGGTGTCGGGCTCGAAGGCCGGCGTGTCGCCGCACC

GCGAGATCGAGGTGATGCGCCAGTCGATCGACGACCACCTGGCCGGCCTGCTGCCGGAGA

CCGACTCGCAGGACATCGTGTCGCTGGCCATGCGCGAGGGCGTGATGGCCCCGGGCAAGC

GCATCCGCCCGCTGCTGATGCTGCTGGCCGCCCGCGACCTGCGCTACCAGGGCTCGATGC

CGACCCTGCTGGACCTGGCCTGCGCCGTGGAGCTGACCCACACCGCCTCGCTGATGCTGG

ACGACATGCCGTGCATGGACAACGCCGAGCTGCGCCGCGGCCAGCCGACCACCCACAAGA

AGTTCGGCGAGTCGGTGGCCATCCTGGCCTCGGTGGGCCTGCTGTCGAAGGCCTTCGGCC

TGATCGCCGCCACCGGCGACCTGCCGGGCGAGCGCCGCGCCCAGGCCGTGAACGAGCTGT

CGACCGCCGTGGGCGTGCAGGGCCTGGTGCTGGGCCAGTTCCGCGACCTGAACGACGCCG

CCCTGGACCGCACCCCGGACGCCATCCTGTCGACCAACCACCTGAAGACCGGCATCCTGT

TCTCGGCCATGCTGCAGATCGTGGCCATCGCCTCGGCCTCGTCGCCGTCGACCCGCGAGA

CCCTGCACGCCTTCGCCCTGGACTTCGGCCAGGCCTTCCAGCTCCTGGACGACCTGCGCG

ACGACCACCCGGAGACCGGCAAGGACCGCAACAAGGACGCCGGCAAGTCGACCCTGGTGA

ACCGCCTGGGCGCCGACGCCGCCCGCCAGAAGCTGCGCGAGCACATCGACTCGGCCGACA

AGCACCTGACCTTCGCCTGCCCGCAGGGCGGCGCCATCCGCCAGTTCATGCACCTGTGGT

TCGGCCACCACCTGGCCGACTGGTCGCCGGTGATGAAGATCGCCTGAGTCATAGCTGTTT

CCTGCCCAGTCACGACGTTGTAAAACGCAAAGGAGATATAGGTGCGCGACCTGATCCTGG

TGGGCGGCGGCCTGGCCAACGGCCTGATCGCCTGGCGCCTGCGCCAGCGCTACCCGCAGC

TCAACCTGCTGCTGATCGAGGCCGGCGAGCAGCCGGGCGGCAACCACACCTGGTCGTTCC

ACGAGGACGACCTGACCCCGGGCCAGCACGCCTGGCTGGCCCCGCTGGTGGCCCACGCCT

GGCCGGGCTACGAGGTGCAGTTCCCGGACCTGCGCCGCCGCCTGGCCCGCGGCTACTACT

CGATCACCTCGGAGCGCTTCGCCGAGGCCCTGCACCAGGCCCTGGGCGAGAACATCTGGC

TGAACTGCTCGGTGTCGGAGGTGCTGCCGAACTCGGTGCGCCTGGCCAACGGCGAGGCCC

TGCTGGCCGGCGCCGTGATCGACGGCCGCGGCGTGACCGCCTCGTCGGCCATGCAGACCG

GCTACCAGCTCTTCCTGGGCCAGCAGTGGCGCCTGACCCAGCCGCACGGCCTGACCGTGC

CGATCCTGATGGACGCCACCGTGGCCCAGCAGCAGGGCTACCGCTTCGTGTACACCCTGC

CGCTGTCGGCCGACACCCTGCTGATCGAGGACACCCGCTACGCCAACGTGCCGCAGCGCG

ACGACAACGCCCTGCGCCAGACCGTGACCGACTACGCCCACTCGAAGGGCTGGCAGCTCG

CCCAGCTCGAACGCGAGGAGACCGGCTGCCTGCCGATCACCCTGGCCGGCGACATCCAGG

CCCTGTGGGCCGACGCCCCGGGCGTGCCGCGCTCGGGCATGCGCGCCGGCCTGTTCCACC

CGACCACCGGCTACTCGCTGCCGCTGGCCGTGGCCCTGGCCGACGCCATCGCCGACTCGC

-continued

CGCGCCTGGGCTCGGTGCCGCTGTACCAGCTCACCCGCCAGTTCGCCGAGCGCCACTGGC

GCCGCCAGGGCTTCTTCCGCCTGCTGAACCGCATGCTGTTCCTGGCCGGCCGCGAGGAGA

ACCGCTGGCGCGTGATGCAGCGCTTCTACGGCCTGCCGGAGCCGACCGTGGAGCGCTTCT

ACGCCGGCCGCCTGTCGCTGTTCGACAAGGCCCGCATCCTGACCGGCAAGCCGCCGGTGC

CGCTGGGCGAGGCCTGCCGCGCCGCCCTGAACCACTTCCCGGACCGCCGCGACAAGGGCT

GACCTGTGTGAAATTGTTATCCGCTTACCCATACGACGTCCCAGACAAAGGAGATATAGA

TGAAGAAGACCGTGGTGATCGGCGCCGGCTTCGGCGGCCTGGCCCTGGCCATCCGCCTGC

AGGCCGCCGGCATCCCGACCGTGCTGCTGGAGCAGCGCGACAAGCCGGGCGGCCGCGCCT

ACGTGTGGCACGACCAGGGCTTCACCTTCGACGCCGGCCCGACCGTGATCACCGACCCGA

CCGCCCTGGAGGCCCTGTTCACCCTGGCCGGCCGCCGCATGGAGGACTACGTGCGCCTGC

TGCCGGTGAAGCCGTTCTACCGCCTGTGCTGGGAGTCGGGCAAGACCCTGGACTACGCCA

ACGACTCGGCCGAGCTGGAGGCCCAGATCACCCAGTTCAACCCGCGCGACGTGGAGGGCT

ACCGCCGCTTCCTGGCCTACTCGCAGGCCGTGTTCCAGGAGGGCTACCTGCGCCTGGGCT

CGGTGCCGTTCCTGTCGTTCCGCGACATGCTGCGCGCCGGCCCGCAGCTCCTGAAGCTGC

AGGCCTGGCAGTCGGTGTACCAGTCGGTGTCGCGCTTCATCGAGGACGAGCACCTGCGCC

AGGCCTTCTCGTTCCACTCGCTGCTGGTGGGCGGCAACCCGTTCACCACCTCGTCGATCT

ACACCCTGATCCACGCCCTGGAGCGCGAGTGGGGCGTGTGGTTCCCGGAGGGCGGCACCG

GCGCCCTGGTGAACGGCATGGTGAAGCTGTTCACCGACCTGGGCGGCGAGATCGAGCTGA

ACGCCCGCGTGGAGGAGCTGGTGGTGGCCGACAACCGCGTGTCGCAGGTGCGCCTGGCCG

ACGGCCGCATCTTCGACACCGACGCCGTGGCCTCGAACGCCGACGTGGTGAACACCTACA

AGAAGCTGCTGGGCCACCACCCGGTGGGCCAGAAGCGCGCCGCCGCCCTGGAGCGCAAGT

CGATGTCGAACTCGCTGTTCGTGCTGTACTTCGGCCTGAACCAGCCGCACTCGCAGCTCG

CCCACCACACCATCTGCTTCGGCCCGCGCTACCGCGAGCTGATCGACGAGATCTTCACCG

GCTCGGCCCTGGCCGACGACTTCTCGCTGTACCTGCACTCGCCGTGCGTGACCGACCCGT

CGCTGGCCCCGCCGGGCTGCGCCTCGTTCTACGTGCTGGCCCCGGTGCCGCACCTGGGCA

ACGCCCCGCTGGACTGGGCCCAGGAGGGCCCGAAGCTGCGCGACCGCATCTTCGACTACC

TGGAGGAGCGCTACATGCCGGGCCTGCGCTCGCAGCTCGTGACCCAGCGCATCTTCACCC

CGGCCGACTTCCACGACACCCTGGACGCCCACCTGGGCTCGGCCTTCTCGATCGAGCCGC

TGCTGACCCAGTCGGCCTGGTTCCGCCCGCACAACCGCGACTCGGACATCGCCAACCTGT

ACCTGGTGGGCGCCGGCACCCACCCGGGCGCCGGCATCCCGGGCGTGGTGGCCTCGGCCA

AGGCCACCGCCTCGCTGATGATCGAGGACCTGCAGTGATCTGGGACGTCGTATGGGTAAG

CTGGACATCACCTCCCACAACGCAAAGGAGATATAGATGTCGCAGCCGCCGCTGCTGGAC

CACGCCACCCAGACCATGGCCAACGGCTCGAAGTCGTTCGCCACCGCCGCCAAGCTGTTC

GACCCGGCCACCCGCCGCTCGGTGCTGATGCTGTACACCTGGTGCCGCCACTGCGACGAC

GTGATCGACGACCAGACCCACGGCTTCGCCTCGGAGGCCGCCGCCGAGGAGGAGGCCACC

CAGCGCCTGGCCCGCCTGCGCACCCTGACCCTGGCCGCCTTCGAGGGCGCCGAGATGCAG

GACCCGGCCTTCGCCGCCTTCCAGGAGGTGGCCCTGACCCACGGCATCACCCCGCGCATG

GCCCTGGACCACCTGGACGGCTTCGCCATGGACGTGGCCCAGACCCGCTACGTGACCTTC

GAGGACACCCTGCGCTACTGCTACCACGTGGCCGGCGTGGTGGGCCTGATGATGGCCCGC

GTGATGGGCGTGCGCGACGAGCGCGTGCTGGACCGCGCCTGCGACCTGGGCCTGGCCTTC

-continued

CAGCTCACCAACATCGCCCGCGACATCATCGACGACGCCGCCATCGACCGCTGCTACCTG

CCGGCCGAGTGGCTGCAGGACGCCGGCCTGACCCCGGAGAACTACGCCGCCCGCGAGAAC

CGCGCCGCCCTGGCCCGCGTGGCCGAGCGCCTGATCGACGCCGCCGAGCCGTACTACATC

TCGTCGCAGGCCGGCCTGCACGACCTGCCGCCGCGCTGCGCCTGGGCCATCGCCACCGCC

CGCTCGGTGTACCGCGAGATCGGCATCAAGGTGAAGGCCGCCGGCGGCTCGGCCTGGGAC

CGCCGCCAGCACACCTCGAAGGGCGAGAAGATCGCCATGCTGATGGCCGCCCCGGGCCAG

GTGATCCGCGCCAAGACCACCCGCGTGACCCCGCGCCCGGCCGGCCTGTGGCAGCGCCCG

GTGTGACTGTCCCCCCAGTTCCAGTACCTGGTCATCATCCTGCCTTTCAAAGGAGATATA

GATGCTGTGGATCTGGAACGCCCTGATCGTGTTCGTGACCGTGATCGGCATGGAGGTGGT

GGCCGCCCTGGCCCACAAGTACATCATGCACGGCTGGGGCTGGGGCTGGCACCTGTCGCA

CCACGAGCCGCGCAAGGGCGCCTTCGAGGTGAACGACCTGTACGCCGTGGTGTTCGCCGC

CCTGTCGATCCTGCTGATCTACCTGGGCTCGACCGGCATGTGGCCGCTGCAGTGGATCGG

CGCCGGCATGACCGCCTACGGCCTGCTGTACTTCATGGTGCACGACGGCCTGGTGCACCA

GCGCTGGCCGTTCCGCTACATCCCGCGCAAGGGCTACCTGAAGCGCCTGTACATGGCCCA

CCGCATGCACCACGCCGTGCGCGGCAAGGAGGGCTGCGTGTCGTTCGGCTTCCTGTACGC

CCCGCCGCTGTCGAAGCTGCAGGCCACCCTGCGCGAGCGCCACGGCGCCCGCGCCGGCGC

CGCCCGCGACGCCCAGGGCGGCGAGGACGAGCCGGCCTCGGGCAAGTGAGTTATATGGAG

GGGGCAAACGCTCTAGAACTAGTGGATCCAAAGGAGATATAGATGTCGGCCGTGACCCCG

ATGTCGAGAGTGGTGCCAAACCAGGCCCTAATCGGCCTGACTTTAGCGGGGCTGATAGCC

ACGGCGTGGCTGAGTCTGCATATTTACGGGGTGTACTTCCATCGTTGGACAATGTGGTCG

ATCCTGACGGTGCCGCTGATCGTGGCCTTCCAGACGTGGCTGTCGGTAGGCCTGTTCATC

GTTGCCCACGACGCAATGCACGGCTCCCTAGCCCCGGGGAGGCCCCGCCTGAACACCGCC

ATCGGGTCCCTGGCCCTAGGCCTGTACGCTGGCTTCAGGTTCGCCCCTCTGAAGACCGCC

CACCATGCCCACCATGCCGCACCGGGCACAGCCGACGACCCGGATTTTCACGCGGACGCC

CCCCGTGCGTTCCTGCCGTGGTTCTACGGCTTTTTCCGTACCTACTTCGGCTGGAGGGAG

CTGGCCGTGCTGACCGTGTTGGTGGCCGTGGCTGTTTTAATCCTGGGCGCCCGAATGCCG

AACTTACTTGTGTTCTGGGCCGCCCCGGCTCTATTATCGGCCTTGCAGCTTTTCACCTTC

GGCACATGGCTGCCGCACCGACACACCGACGACGCCTTCCCGGACCACCACAACGCTCGC

ACTTCACCCTTTGGCCCCATCCTGTCTCTGCTGACCTGCTTCCACTTCGGCCGGCACCAT

GAGCACCACCTGACTCCGTGGAAACCGTGGTGGAGGCTGTTCTCGTAGCGATACCGTCGA

CTTCGAGCAAATAAAACGAAAGGCTCAGTCGAAAGACTGGGCCTTTCGTTTTATCTGTTG

TTTGTCGGTGAACGCTCTCATTAATGAATCGGCCAACGCGCGGGGAGAGGCGGTTTGCGT

ATTGGGCGCATGCATAAACTGCTGCCGTTTAGCCCGGATAGCGTGGTGACCCACGGCGAT

TTTAGCCTGGATAACCTGATTTTCGATGAAGGCAAACTGATTGGCTGCATTGATGTGGGC

CGTGTGGGCATTGCGGATCGTTATCAGGATCTGGCCATTCTGTGGAACTGCCTGGGCGAA

TTTAGCCCGAGCCTGCAAAAACGTCTGTTTCAGAAATATGGCATTGATAATCCGGATATG

AACAAACTGCAATTTCATCTGATGCTGGATGAATTTTTCTAAGACCCTTGTCTAATCAAT

GCGGACCCTAGAGGTCCCCTTTTTTATTTTAAAAATTTTTTCACAAAACGGTTTACAAGC

ATAAAATCTCTGAAGATGTGTATAAGAGACAGACTAGTCTTGGACTCCTGTTGATAGATC

CAGTAATGACCTCAGAACTCCATCTGGATTTGTTCAGAACGCTCGGTTGCCGCCGGGCGT

TTTTTATTGGTGAGAATCCAGGGGTCCCCTGGTTTAAACTACACAAGTAGCGTCCTGAAC

-continued

GGAACCTTTCCCGTTTTCCAGAATCTGATGTTCCATGTGACCTCCTAACATGGTAACGTT

CATGATTACCAGTGCACTGCATCGTGCGGCGGATTGGGCGAAAAGCGTGTTTTCTAGTGC

TGCGCTGGGTGATCCGCGTCGTACCGCGCGTCTGGTGAATGTTGCGGCGCAACTGGCCAA

ATATAGCGGCAAAAGCATTACCATTAGCAGCGAAGGCAGCAAAGCCATGCAGGAAGGCGC

GTATCGTTTTATTCGTAATCCGAACGTGAGCGCGGAAGCGATTCGTAAAGCGGGTGCCAT

GCAGACCGTGAAACTGGCCCAGGAATTTCCGGAACTGCTGGCAATTGAAGATACCACCTC

TCTGAGCTATCGTCATCAGGTGGCGGAAGAACTGGGCAAACTGGGTAGCATTCAGGATAA

AAGCCGTGGTTGGTGGGTGCATAGCGTGCTGCTGCTGGAAGCGACCACCTTTCGTACCGT

GGGCCTGCTGCATCAAGAATGGTGGATGCGTCCGGATGATCCGGCGGATGCGGATGAAAA

AGAAAGCGGCAAATGGCTGGCCGCTGCTGCAACTTCGCGTCTGAGAATGGGCAGCATGAT

GAGCAACGTGATTGCGGTGTGCGATCGTGAAGCGGATATTCATGCGTATCTGCAAGATAA

ACTGGCCCATAACGAACGTTTTGTGGTGCGTAGCAAACATCCGCGTAAAGATGTGGAAAG

CGGCCTGTATCTGTATGATCACCTGAAAAACCAGCCGGAACTGGGCGGCTATCAGATTAG

CATTCCGCAGAAAGGCGTGGTGGATAAACGTGGCAAACGTAAAAACCGTCCGGCGCGTAA

AGCGAGCCTGAGCCTGCGTAGCGGCCGTATTACCCTGAAACAGGGCAACATTACCCTGAA

CGCGGTGCTGGCCGAAGAAATCAATCCGCCGAAAGGCGAAACCCCGCTGAAATGGCTGCT

GCTGACCAGCGAGCCGGTGGAAAGTCTGGCCCAAGCGCTGCGTGTGATTGATATTTATAC

CCATCGTTGGCGCATTGAAGAATTTCACAAAGCGTGGAAAACGGGTGCGGGTGCGGAACG

TCAGCGTATGGAAGAACCGGATAACCTGGAACGTATGGTGAGCATTCTGAGCTTTGTGGC

GGTGCGTCTGCTGCAACTGCGTGAATCTTTTACTCCGCCGCAAGCACTGCGTGCGCAGGG

CCTGCTGAAAGAAGCGGAACACGTTGAAAGCCAGAGCGCGGAAACCGTGCTGACCCCGGA

TGAATGCCAACTGCTGGGCTATCTGGATAAAGGCAAACGCAAACGCAAAGAAAAAGCGGG

CAGCCTGCAATGGGCGTATATGGCGATTGCGCGTCTGGGCGGCTTTATGGATAGCAAACG

TACCGGCATTGCGAGCTGGGGTGCGCTGTGGGAAGGTTGGGAAGCGCTGCAAAGCAAACT

GGATGGCTTTCTGGCCGCGAAAGACCTGATGGCGCAGGGCATTAAAATCTAATGGAATCG

AACCCAGCTTTCTTGTACAAAGTTGGCATTATAAGAAAGCATTGCTTATCAATTTGTTGC

AACGAACAGGTCACTATCAGTCAAAATAAAATCATTATTTG

---

What is claimed:

1. An expression construct comprising:

a nucleic acid sequence for a crtW carotenoid ketolase gene from *Brevundimonas* strain OB307 that encodes the amino acid sequence of SEQ ID NO: 2, the expression construct adapted to produce carotenoids in a heterologous biological host cell.

2. The expression construct of claim 1, wherein the expression construct is a plasmid.

3. The expression construct of claim 1, wherein the expression construct is integrated into a genome of the biological host cell.

4. A method of producing a nucleic acid sequence encoding a crtZ-crtW carotenoid hydroxylase-ketolase fusion protein of SEQ ID NO: 3, the method comprising:

obtaining a crtW gene from a species of *Brevundimonas,* adding a sequence encoding a ten amino acid linker peptide of SEQ ID NO: 3 and 4 to the 3'-end of the crtW sequence;

adding a sequence encoding a crtZ gene lacking the N-terminal methionine codon and containing a 3' stop codon to the 3'-end of the linker peptide sequence; and inserting the entire DNA construct into an expression vector.

5. The method of claim 4, wherein the nucleic acid sequence is part of an expression construct adapted to produce carotenoids when functionally integrated into a biological host cell.

6. The method of claim 4, wherein the fusion protein is further expressed in a biological host cell capable of using $CO_2$ and $H_2$ to satisfy at least part of its carbon and energy requirements.

7. The method of claim 4, wherein the crtW sequence is a ketolase gene from *Brevundimonas* strain OB307 that encodes the amino acid sequence of SEQ ID NO: 2.

8. The method of claim 4, wherein the nucleic acid sequence is adapted to produce carotenoids when functionally integrated in a biological host cell.

9. An expression construct encoding a crtZ-crtW carotenoid hydroxylase-ketolase fusion protein of SEQ ID NO: 3, wherein (a) the crtW portion of the fusion is a ketolase gene from *Brevundimonas* strain OB307 that encodes the amino acid sequence of SEQ ID NO: 2, and (b) the nucleic acid sequence is adapted to produce carotenoids when functionally integrated in a biological host cell.

* * * * *